(12) United States Patent
Unciti-Broceta et al.

(10) Patent No.: US 8,759,104 B2
(45) Date of Patent: Jun. 24, 2014

(54) CATIONIC LIPIDS

(75) Inventors: Asier Unciti-Broceta, Edinburgh (GB);
Aleksandra Liberska, Poznan (PL);
Mark Bradley, Edinburgh (GB)

(73) Assignee: The University Court of the University of Edinburgh, Edinburgh (GB)

( * ) Notice: Subject to any disclaimer, the term of this patent is extended or adjusted under 35 U.S.C. 154(b) by 0 days.

(21) Appl. No.: 13/698,804

(22) PCT Filed: May 17, 2011

(86) PCT No.: PCT/GB2011/000749
§ 371 (c)(1),
(2), (4) Date: Nov. 19, 2012

(87) PCT Pub. No.: WO2011/144892
PCT Pub. Date: Nov. 24, 2011

(65) Prior Publication Data
US 2013/0065308 A1    Mar. 14, 2013

(30) Foreign Application Priority Data
May 18, 2010 (GB) .................................. 1008267.5

(51) Int. Cl.
| | | |
|---|---|---|
| *C07C 251/02* | (2006.01) | |
| *C07K 5/093* | (2006.01) | |
| *C07K 7/06* | (2006.01) | |
| *A61K 31/713* | (2006.01) | |
| *A61K 47/48* | (2006.01) | |
| *C12N 15/88* | (2006.01) | |

(52) U.S. Cl.
CPC ............ *C07C 251/02* (2013.01); *A61K 31/713* (2013.01); *A61K 47/48046* (2013.01); *C12N 15/88* (2013.01); *A61K 47/48323* (2013.01); *C07K 5/0819* (2013.01)
USPC ...... 435/458; 514/21.9; 514/21.91; 514/44 A; 514/44 R; 514/616; 530/331; 554/53

(58) Field of Classification Search
None
See application file for complete search history.

(56) References Cited
U.S. PATENT DOCUMENTS

| | | | |
|---|---|---|---|
| 5,589,466 A | 12/1996 | Carson et al. | |
| 5,650,096 A | 7/1997 | Harris et al. | |
| 6,458,381 B1 | 10/2002 | Sourovoi et al. | |
| 6,890,554 B2 | 5/2005 | Jessee | |
| 2004/0253225 A1* | 12/2004 | Cappelleti et al. | 424/94.63 |
| 2009/0012306 A1 | 1/2009 | Takeoka et al. | |

FOREIGN PATENT DOCUMENTS

| | | |
|---|---|---|
| EP | 2116599 | 11/2009 |
| WO | WO 00/30444 | 6/2000 |
| WO | WO 2010/054102 | 5/2010 |
| WO | WO 2010054102 A2 * | 5/2010 |

OTHER PUBLICATIONS

Furuhata M et al: "Design, synthesis and gene delivery efficiency of novel oligo-arginine-linked PEG-lipids: Effect of oligo-arginine length", International Journal of Pharmaceutics, vol. 316, No. 1-2, Jun. 19, 2006, pp. 109-116.*
Bhattacharya, S., et al., "Advances in gene delivery through molecular design of cationic lipids", *Chem. Commun.*, pp. 4632-4656, (2009).
Furuhata, M., et al., "Design, synthesis and gene delivery efficiency of novel oligo-arginine-linked PEG-lipids: Effect of oligo-arginine length", *International Journal of Pharmaceutics*, vol. 316, pp. 106-116, (2006).
Heinze, M., et al., "Novel cationic lipids based on malonic acid amides backbone: transfection efficacy and cell toxicity properties", *Bioconjugate Chemistry*, vol. 21, No. 4, pp. 696-708, (2010).
Heyes, J., et al., "Synthesis of novel cationic lipids: Effect of structural modification on the efficiency of gene transfer", *Journal of Medicinal Chemistry*, vol. 45, No. 1, (2002).
Kirby, A., et al., "Gemini surfactants: New synthetic vectors for gene transfection", *Angew. Chem. Int. Ed.*, vol. 42, pp. 1448-1457, (2003).
Martin, B., et al., "The design of cationic lipids for gene delivery", *Current Pharmaceutical Design*, vol. 11, pp. 375-394, (2005).
Mintzer, M., et al., "Nonviral vectors for gene delivery", *Chem. Rev.*, vol. 109, pp. 259-302, (2009).
Obata, Y., et al., "Evaluation of cationic assemblies constructed with amino acid based lipids for plasmid DNA delivery", *Bioconjugate Chemistry*, vol. 19, No. 5, pp. 1055-1063, (2008).
Obata, Y., et al., "Plasmid DNA-encapsulating liposomes: Effect of a spacer between the cationic head group and hydrophobic moieties of the lipids on gene expression efficiency", *Biochimica et Biophysica Acta*, vol. 1788, No. 5, pp. 1148-1158, (2009).
Notification of Transmittal of the International Search Report and the Written Opinion of the International Searching Authority, or the Declaration for International Application No. PCT/GB2011/000749 mailed Sep. 14, 2012.
Search Report under Section 17(5) for GB Application No. 1008267.5 dated Dec. 3, 2010.
Farhood et al., *Biochim. Biophys. ACTA*, vol. 1235, pp. 289-295 (1995).
Ellens et al., *Biochemistry*, vol. 25, pp. 4141-4147 (1986).
Koltover et al., *Science*, vol. 281, pp. 78-81 (1998).
Unciti-Broceta et al., *J. Med. Chem.*, vol. 51, pp. 4076-4084 (2008).

(Continued)

*Primary Examiner* — Janet Epps-Smith
(74) *Attorney, Agent, or Firm* — Hoxie & Associates, LLC

(57) ABSTRACT

The invention provides a cationic lipid comprising:
(i) one head group, comprising one or more amino acids, in which at least one amino acid has a side chain that comprises a cationic moiety or a cationic precursor;
(ii) a linking moiety of formula (5):

—(HNR$^5$)$_2$NC(O)R$^3$C(O)—     (5), wherein:
each R$^5$ is independently an optionally substituted C$_{1-4}$ alkylene moiety; and
R$^3$ is an optionally substituted alkylene or alkenylene moiety; and
(iii) two lipophilic moieties,
wherein the head group and each of the lipophilic moieties are connected to the linking moiety through amide linkages.

20 Claims, 1 Drawing Sheet

(56) References Cited

OTHER PUBLICATIONS

Bloomfield, *Curr. Opin. Struct. Biol.*, vol. 6, pp. 334-341 (1996).
Unciti-Broceta et al., *Bioorg. Med. Chem.*, vol. 17, pp. 959-966 (2009).
Goeddel, "Gene Expression Technology: Methods in Enzymology", *Academic Press*, vol. 185, pp. 3-7, (1990).
Seed, *Nature*, vol. 329, p. 840 (1987).
Kaufman et al., *EMBO J.*, vol. 6, pp. 187-195 (1987).
Edgington, *Biotechnology*, vol. 10, pp. 256-262 (1992).
Paolella et al., *Embo J.*, pp. 1913-1919 (1992).
EWERTet al., *J. Med. Chem.*, 45:5023-5029 (2002).

* cited by examiner

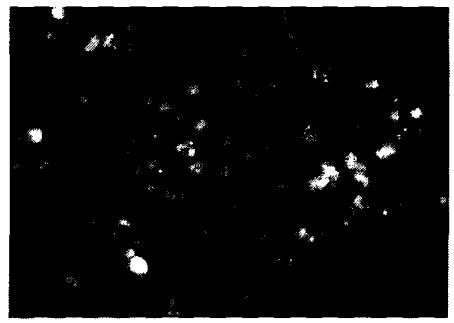 
FIG. 1A    FIG. 1B
FIG. 2

CATIONIC LIPIDS

CROSS REFERENCE TO RELATED APPLICATIONS

This application is a United States Application under 35 U.S.C. 371 claiming benefit of PCT Application No. PCT/GB2011/000749, filed on May 17, 2011, which claims the benefit of GB 1008267.5, filed on May 18, 2010, the contents of each of which are incorporated herein by reference.

FIELD

This invention relates to cationic lipids. More particularly the invention relates to biocompatible cationic lipids having one headgroup comprising one or more amino acids, one or more of which have side chains that serve to provide a cationic moiety, and two lipophilic tail groups. The lipids are of utility in various applications, and in particular in permitting delivery of DNA and RNA into cells. As such the lipids have specific utility in the fields of biology and medicine.

BACKGROUND

Viral gene delivery, as a molecular biology tool or as a potential approach to gene-based therapies, is without doubt the most efficient method of DNA delivery, or transfection, found to date. Although viral vectors are generally more efficient than non-viral vectors, several disadvantages of viral vectors (e.g. antigenicity, production cost, limited size of cargo, etc) mean that non-viral chemical based delivery systems represent a very attractive alternative, especially because of their relatively low cost and procedural simplicity. Despite numerous improvements, however, the in vivo efficacy of non-viral vectors still needs to be increased for both clinical and research purposes, which have been most widely studied to date.

Among the many non-viral vectors (for a review see M A Mintzer and E E Simanek (*Chem. Rev.*, 2009, 109, 259-302)), cationic lipids are perhaps the class of compounds that have been most widely studied to date. For detailed reviews see B Martin et al., (*Curr. Pharm. Design*, 2005, 11, 375-394) and S Bhattacharya and A Bajaj (*Chem. Commun.*, 2009, 4632-4656).

As is well-known and well-understood in the art cationic lipids typically comprise three main parts: a lipophilic component attached through a linking moiety to a positively charged, polar head group. The positively charged, polar head group is typically the result of protonation of one or more amino groups, or may arise by the provision of quaternary amines, which bears a permanent positive charge.

When cationic lipids are mixed with DNA or RNA, or other molecules, in an aqueous solution, electrostatic and hydrophobic interactions are known to lead to organization via a multi-step mechanism into a liposome-like complex known as a lipoplex (see B Martin et al., infra). At the end of this multi-step process, the DNA or RNA is condensed, generally the cationic lipids totally envelop the plasmid (providing shielding from nucleases in the surrounding environment) (see B Martin et al., infra). Use of an excess of cationic lipid provides an overall a positive charge which is postulated to mediate cellular uptake (via non-specific endocytosis) following an interaction with negatively charged cell surface structures such as phospholipids, or heparin sulphates or other proteoglycans.

The first reported cationic lipid used for DNA delivery DOTMA, (N-(1-(2,3-dioleyloxy)propyl)-N,N,N-trimethyl-ammonium chloride), was reported in 1987. Now, an enormous range of cationic lipids have been synthesized (see B Martin et al. and S Bhattacharya and A Bajaj, infra) and several are commercially available. These include Lipofectamine™ 2000 (Invitrogen) and Effectene® Transfection Reagent (Qiagen).

Lipoplex formulation is often assisted by the addition of a neutral surfactant, such as dioleyl phosphatidyl ethanolamine (DOPE), which is believed to improve the transfection abilities of the mixture (H Farhood et al., *Biochim. Biophys. Acta,* 1995, 1235, 289-295). Due to its fusogenic properties (H Farhood et al., (infra); H Ellens, et al. (*Biochemistry,* 1986, 25, 4141-7); and I Koltover. et al. (*Science,* 1998, 281, 78-81)) this so-called "co-lipid", or helper lipid, appears to drive lipoplex assembly (possibly promoting a transition from lamellar to hexagonal phase) by increasing the release of counterions, although DOPE itself is not required for lipoplex assembly. The presence of DOPE is thought to loosen the binding of the cationic lipid to the DNA and enhance endosomal escape of the lipoplexes in to the cytoplasm, a step which is probably the most important in the entire transfection process.

Typically, the head groups found in cationic lipids are nitrogen-based motifs which are protonated (quaternary amines) or will become protonated at physiological pH. The resultant positive charge assists in the binding and packing of the phosphate diester backbone of DNA and RNA. For example, M Furuhata et al. (*Int. J. Pharm.,* 2006, 316, 109-116) describe the design, synthesis and evaluation of in vitro gene delivery efficacy of a series of cationic lipids constituted by using 3,5-bis(dodecyloxy)benzamide as the lipid component, the amide group of which is connected to the C-termini of four different oligo-arginines through poly(ethylene glycol) (PEG) spacers.

Generally the lipophilic component is composed of two long chain fatty acids or a cholesterol-based derivative. Other than with cholesterol-based cationic lipids, the hydrophobic moiety of cationic lipids generally contains unsaturated or saturated alkyl or acyl (alkylcarbonyl) chains, with a chain length of typically about 12-18 carbon atoms. Long saturated tails tend to display relatively strong intermolecular interactions and a low propensity for mixing with neutral helper lipids such as DOPE. The addition of double bonds leads to less compact packing. Hence, hydrocarbon tail length and saturation affect lipoplex intra-dynamics and ultimately the packing efficiency of DNA. Although the majority of cationic lipids have two chains, on-going research has looked at the use of single chain detergents that are capable of dimerisation via oxidation and tripod-like cationic lipids (A Unciti-Broceta et al., *J. Med. Chem.,* 2008, 51, 4076-4084). Cholesterol-based tails are often used as an alternative to aliphatic chains since cholesterol is rigid and biodegradable and can be considered to be a structural mimic of two long fatty acid chains. Cholesterol is also used as an alternative co-lipid to DOPE.

An acknowledged class of cationic lipids is constituted by compounds known as gemini surfactants (for a mini review see A J Kirby et al., *Angew. Chem. Int. Ed.,* 2003, 42, 1448-1457). Unlike most other cationic lipids, gemini surfactants contain two head groups and two aliphatic chains, which are linked by a rigid or flexible spacer. The presence of two head groups (each with an associated aliphatic tail) is described by A J Kirby et al. as having greatly enhanced surfactant properties relative to the corresponding "monovalent" (i.e. single chain, single head group) compounds.

As the packing properties of cationic lipids are important for optimal condensation of DNA (see V A Bloomfield, *Curr. Opin. Struct. Biol.,* 1996, 6, 334-341) the structures of cationic lipids are generally very carefully designed to enable effective DNA-binding and lipoplex formation. Indeed the prior art is replete with reports of studies into the rational design of cationic lipids by way of modification of the three main parts (i.e. the lipophilic component, the linking motif and the head group), which studies have allowed the elucidation of structure-activity relationships. For example it is postulated that the larger the imbalance between the cross-sectional area of the cationic (small) end and the large hydrophobic moiety, the more 'cone-shaped' the cationic lipid, which is believed by some to create greater instability in the resulting lipid assembly. Such instability can lead to improved transfection with DNA or RNA release in to the cytoplasm improved.

Hydrophobic and hydrophilic portions of cationic lipids have generally been joined using amide, ether, ester or carbamate bonds, although there is no optimal bond. Ether-containing cationic lipids are more stable than ester-containing counterparts with carbamate-containing lipids viewed as a good balance between stability and toxicity. The linking bond may be considered to control the cationic amphiphilic lipid's stability, thereby controlling the balance between persistence and toxicity. In terms of linker design there are a great number of reports including the use of photosensitive linkers and the incorporation of environmental sensitive groups, where intracellular hydrolysis leads to controlled DNA delivery at defined stages during intracellular lipoplex trafficking.

Notwithstanding all the prior art, however, there is still a requirement for alternative cationic lipids that offer one or more properties such as reduced cell toxicity, promotion of endosomal escape of molecules, e.g. nucleic acids, and, where the molecule to be transfected is a DNA molecule, folding of that DNA.

Despite the vast amount of work undertaken to date in the field of cationic lipids, therefore, it is desired to develop further cationic lipids capable of ameliorating or obviating one or more of the problems of in vivo efficacy of the transfection process, toxicity, cost and simplicity of design.

BRIEF SUMMARY

We have surprisingly found that cationic lipids that comprise a single head group comprising one or more cationic moieties, or precursors to cationic moieties, which head group is connected via amide bonds to a linking moiety to which is attached two lipophilic domains connected through amide bonds, show excellent transfection efficiencies. Viewed from one aspect therefore the invention provides a cationic lipid comprising:
 (i) one head group, comprising one or more amino acids, in which at least one amino acid has a side chain that comprises a cationic moiety or a cationic precursor;
 (ii) a linking moiety; and
 (iii) two lipophilic moieties,
wherein the head group and each of the lipophilic moieties are connected to the linking moiety through amide linkages.

Viewed from a second aspect the invention provides a composition comprising a cationic lipid according to the first aspect of the invention in combination with an additional lipid.

Viewed from a third aspect the invention provides a composition comprising a cationic lipid according to the first or second aspects of the invention in combination with a biologically active molecule, such as a polynucleotide molecule.

Viewed from a fourth aspect the invention provides a method for transfecting a polynucleotide into a cell comprising contacting a cell with a composition according to the third aspect of this invention.

Viewed from a fifth aspect the invention provides the use of a composition of the invention for use in medicine.

Viewed from a sixth aspect, the invention provides a kit of parts comprising a composition according to this invention and a cell into which the polynucleotide of the composition may be transfected.

BRIEF DESCRIPTION OF THE FIGURES

FIG. 1 shows imaging of HeLa cells transfected with fluorescein-labelled siRNA imaged under FITC (FIG. 1(A)) and DAPI (FIG. 1(B)) excitation filters.

FIG. 2 shows representative luminescence imaging of anaesthetised mice 48 hours after transfection with a luciferase-expressing plasmid, one (transfected to the mouse shown on the left) with a naked plasmid and one (transfected to the mouse shown on the right) additionally with a cationic lipid of the invention.

DETAILED DESCRIPTION

The present invention provides cationic lipids with an architecture that is designed to be susceptible to degradation under physiological conditions. The degradation is facilitated, in particular in the context of transfection into cells, by the presence of the amide moieties that are susceptible to hydrolytic enzymatic activity. This occurs after cytoplasm entry by lipoplexes since amide bonds are susceptible to hydrolysis by intracellular hydrolases such as peptidases and amidohydrolases.

A characteristic feature of the present invention is the provision of one head group that comprises at least one amino acid having a side chain that displays a cationic moiety or cationic precursor. The cationic lipids of the present invention may thus be clearly distinguished from the so-called gemini surfactants discussed above, which have two head groups, i.e. two charged regions separated by a spacer.

The at least one amino acid comprised within the head group that comprises a cationic moiety or cationic precursor need not be particularly limited. Any amino- and carboxylic acid-containing molecule having a side chain that comprises a cationic moiety or cationic precursor may be suitable. Typically in such molecules, the amino and carboxylic acid functionalities are separated by short, optionally substituted (but generally unsubstituted) alkylene chains of from one to four carbon atoms in length.

By alkyl is meant herein a saturated hydrocarbyl moiety, which may be straight-chain, cyclic or branched (typically straight-chain unless the context dictates to the contrary). By alkylene is meant an alkyl group—i.e. a saturated hydrocarbyl moiety, which may be straight-chain, cyclic or branched (typically straight-chain unless the context dictates to the contrary)—from which a hydrogen atom has been formally abstracted. Typically alkyl and alkylene groups will comprise from 1 to 25 carbon atoms, for example 1 to 10 carbon atoms, such as 1 to 6 carbon atoms. Alkyl and alkylene groups may be substituted, for example once, twice, or three times, e.g. once, i.e. formally replacing one or more hydrogen atoms of the group. Examples of such substituents are halo (e.g. fluoro, chloro, bromo and iodo), aryl, heteroaryl, hydroxy, nitro, amino, alkoxy, alkylthio, carboxy, cyano, thio, formyl, ester, acyl, thioacyl, amido, carbamido, sulfonamido and the like.

In many embodiments of the invention, however, the amino acid having a side chain that comprises a cationic moiety or cationic precursor will be an α-amino acid, that is wherein the amino and carboxylic acid functionalities are attached to a common carbon atom, the α-carbon atom, and in which the α-carbon atom is substituted by the side chain that comprises the cationic moiety or cationic precursor.

The side chain that comprises the cationic moiety or cationic precursor may be any convenient linker that connects the chain or atom (e.g. an α-carbon atom) linking the amino and carboxylic acid functionalities of the amino acid with the cationic moiety or cationic precursor. Typically such linkers will comprise from one to six carbon atoms and are optionally substituted (but generally unsubstituted) alkylene chains.

The cationic moieties or cationic precursors may be derived from any convenient functional group. Whilst most cationic precursors are nitrogen-based, as is known in the art (see e.g. B Martin et al. (infra)), other cationic groups such as phosphonium and arsonium moieties may also be used. Whilst the ensuing discussion focuses on nitrogen-based moieties as the cationic species, positively charged (quaternary) amines or amines capable of undergoing protonation at physiological pH, the present invention is not to be considered to be so limited.

It is the susceptibility of nitrogen-based and other groups to protonation that is the reason for the use herein of the term "cationic precursors": by cationic precursors is meant herein functional groups that can provide cationic moieties upon protonation at physiological pH, or by quaternisation. Given that it is the cationic moieties themselves that are useful in most applications, the following discussion focuses primarily upon these.

Counteranions to protonated amino, amidine or guanidine moieties or, where used, quaternary amino cations, are not particularly limited. Appropriate anions include halide anions such as fluoride, iodide, bromide and chloride, acetate, trifluoroacetate, or bisulfate.

Alternatively, the cationic form of the lipids may be generated simply by contacting their unprotonated precursors, if appropriate, with aqueous buffer. The resultant protonation serves to provide the desired cationic lipids.

Typically the cationic moieties are protonated amine, amidine or guanidine groups, these groups being protonated at physiological pH. Guanidine (—NH—C(=NH)NH$_2$) groups are strongly basic and are thus attractive to use as the moieties from which cationic head groups are derived. The guanidine group is found, for example, in the natural amino acid arginine.

Alternatively the cationic moieties may be derived from (e.g. result from protonation of) amines such as primary, secondary or tertiary amines or may be quaternary (i.e. permanently charged) amines. The cationic moieties may thus be constituted by protonated primary amines although, as is known in the art, quaternary amines, or protonated secondary and tertiary amines, may also be used as the cationic head groups. The primary amine group is found for example in the natural amino acids lysine and ornithine. A further example of a cationic moiety is the imidazole ring, found in the natural amino acid histidine.

In many embodiments, the amino acid having a side chain that comprises a cationic moiety or cationic precursor is a naturally occurring α-amino acid. The amino acid may thus be any basic amino acid (i.e. amino acids having a side chain that is protonated at physiological pH). Examples of such amino acids include arginine, lysine, histidine and ornithine. An advantage of using such naturally occurring amino acids as the building blocks from which to form the head groups is the resultant lower toxicity to the cationic lipids: after lipoplex endocytosis and cleavage of the amide bonds, an at least relatively non-toxic amino acid is revealed.

In some embodiments of the invention the cationic head group only comprises one amino acid, which serves to provide desired cationic functionality. In other embodiments the head group may comprise two or more amino acids, e.g. between two and ten amino acids, often between about two and five amino acids such as two, three or four amino acids. According to some embodiments of the invention the head group comprises one, two or three amino acids.

The second and subsequent amino acids in the head group, if present, advantageously may but need not be the same as the mandatory amino acid (i.e. the amino acid that has a side chain that comprises a cationic moiety or precursor thereto). The other amino acids, if present, may also be basic amino acids, e.g. natural basic α-amino acids such as those described above. However, they need not be and may be, for example, other amino acids. Typically, where non-basic amino acids are present in the head group, these are other than acidic amino acids (i.e. having an acidic side chain such as aspartic acid, glutamic acid, cysteine and tyrosine, particularly aspartic and glutamic acids). Typically each of a plurality of amino acids in the head group will be the same, often naturally occurring α-amino acids. In particular embodiments the head group will comprise an arginine amino acid or a plurality (e.g. from two to five or from two to four) arginine molecules.

The head group comprises one or more amino acids, that is to mean that other atoms may be present within the head group that do not derive from the head group's constituent amino acid(s). Typically, however, such additional structural component will be at a minimum. Indeed the head group will generally consist essentially of one or more amino acids, in which at least one (and according to some embodiments each) amino acid has a side chain that comprises a cationic moiety or a cationic precursor. By this is meant that according to these embodiments head groups are excluded which have additional structure that materially affect the fundamental and novel characteristics of these embodiments of the invention. To use alternative words additional structural features may be present only if the characteristics of the resultant head groups are not materially affected by the presence of such architecture.

The head group of the cationic lipids of this invention is connected to the linking moiety through an amide linkage. In many embodiments of the invention this amide linkage will be derived, in part, from either an amino group or a carboxylic acid of the amino acid of the head group or amino acid of the head group that is adjacent to the linking moiety (where there is more than one amino acid in the head group). In many embodiments of the invention the nitrogen atom of the amide bond linking the head group to the linking moiety is derived from an amino group (often an α-amino group) of an or the amino acid of the head group.

Within the head group, where this comprises a plurality of amino acids, the constituent amino acids are typically condensed, whereby to form amide bonds, between adjacent amino acids. Thus, for example, two arginine molecules may be condensed and the resultant dimer attached to the remainder of the molecule by way of the terminal amino group, this group forming part of the amide bond linking the head group to the linking moiety.

Typically, but not necessarily, where adjacent (condensed) amino acids are connected through amide bonds within the head group, these amide bonds are derived from α-carboxylic acids and α-amino groups of adjacent amino acids. However, as the skilled person is aware, where constituent amino acids comprise additional (non-α) amino or carboxylic acid functionality, the possibility exists to form amide bonds from these additional amino and acid functionalities. Thus, for example, it is possible to form oligo (ε-lysine), in which the amide bonds are formed from ε-amino and α-carboxylic functionality from adjacent amino acids. Still further, mixtures of peptide bonds, some derived from α,α-functionality, some derived from α,ε- or other combinations, are possible. Whilst the present invention embraces all such possibilities, amide bonds within the head group (in contradistinction to the amide bond connecting the head group to the linking moiety), will normally be α,α-peptide bonds (i.e. formed from condensation between α-amino and α-carboxylic acid functionalities of adjacent amino acids).

At the terminus of the head group, i.e. at the end of the head group not attached to the remainder of the cationic lipid, the structure of the head group is designed, in many embodiments of the invention, to display a terminal amino group of formula —N(R$^1$), wherein each R$^1$ is independently hydrogen or a C$_{1-5}$, e.g. C$_{1-3}$, alkyl, or a group of the formula —OR$^1$, wherein R$^1$ is as immediately hereinbefore defined. According to particular embodiments of the invention the head group is designed to display a terminal amino group of formula —N(R$^1$). According to further particular embodiments of the invention the head group is designed to display a terminal amino group of formula —NH$_2$.

Where the head group is connected to the linking moiety by way of a nitrogen atom or a constituent amino acid, typically a nitrogen atom attached to the α-carbon atom, the terminus of the head group, whether the head group is made (as is typically the case) from a plurality of condensed amino acids, or is made from a single amino acid, the carboxylic aid of the (terminal) amino acid is typically derivatised to an amide of formula —C(O)(NR$^1$)$_2$ or ester of formula —C(O)OR$^1$, wherein OR$^1$ and N(R$^1$)$_2$ are as hereinbefore defined. This derivatisation may be achieved during synthesis of the cationic lipids; this is discussed in greater detail below.

Alternatively the head group may instead contribute a carbon atom (from the carboxylic acid of the amino acid adjacent to the linking moiety). In this case the amino group of the terminal amino acid may either remain in the cationic lipid as a primary amino group or be derivatised to an amine of formula —N(R$^1$)$_2$, wherein R$^1$ is as hereinbefore defined.

In accordance with the foregoing, therefore, it will be understood that a head group according to particular embodiments of the invention may be represented either by formula (1) or formula (2):

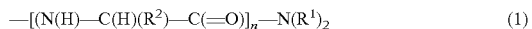

(1)

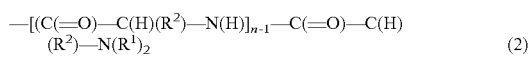

(2)

wherein:
each R$^1$ is independently as hereinbefore defined;
n is from 1 to 10, for example from 1 to 3; and
each R$^2$ is independently the side chain of an α-amino acid, typically a naturally occurring α-amino acid, with the proviso that at least one R$^2$ is the residue of a basic amino acid, for example, arginine, lysine, histidine or ornithine.

In formulae (1) and (2) the N(H) and C(O) groups depicted on the left hand side of each formula constitute a portion of the amide bond that connects the head group to the linking moiety.

According to particular embodiments of the invention the head group is of formula (1). According to these embodiments, and embodiments of the invention wherein the head group is of formula (2), each R$^2$ (if more than one is present) is independently a side chain of a basic amino acid and typically, wherein a plurality of R$^2$ groups are present, each R$^2$ is the same and, according to particular embodiments of the invention, is the side chain of arginine.

The nature of the linking moiety of the cationic lipids of this invention is not of general structural significance, it being understood in the art that the more important regions of cationic lipids are the lipophilic tail(s) and hydrophilic head group(s). That said, the linking moiety does of course separate the lipophilic and hydrophilic regions of cationic lipids and modification of the linking moiety (e.g. its chemical nature and/or length, within the normal skill of those in the art) allows tailoring of the stability and biodegradability of the lipids.

The linking moiety present in the cationic lipids of the invention is derived from, and typically introduced by way of, a polyfunctional molecule with functionality appropriate to react with molecules that serve to introduce the head group and the lipophilic moieties into the cationic lipid. Thus, for example, where the head group is connected to the linking moiety through the amide linkages using an amino group of an amino acid from which the head group is formed, the polyfunctional molecule will typically comprise a carboxylic acid, optionally activated, whereby to allow reaction to generate the desired amide bond. At the other end of the lipids, where the two lipophilic moieties are connected to the linking moiety through amide linkages, then these amide linkages will typically be derived from amino moieties within the polyfunctional molecule and carboxylic acids, optionally activated, present in lipophilic units, such as fatty acids, from which the lipophilic moieties may be derived.

Appropriate polyfunctional molecules from which the linking moiety may be derived, and linking moieties, will thus be evident to those skilled in the art. However, and conveniently, we find that compounds resultant from the conjugation of a dicarboxylic acid, or an activated derivative thereof, and a linear triamine or a protected derivative thereof, are excellent building blocks from which to prepare the cationic lipids of this invention.

As mentioned, the nature of the linking moiety in the cationic lipids of this invention is not of general structural significance. However, the polyfunctional molecules resultant from conjugation of a dicarboxylic acid, or activated derivative thereof (including anhydrides), and a linear triamine, whereby to provide a molecule comprising two amine groups and one carboxylic acid, optionally activated, are particularly useful molecules, in part since the constituent molecules—i.e. the triamines and dicarboxylic acids, which result upon degradation, e.g. in vivo—may be selected so as to minimise toxicity issues.

A dicarboxylic acid used in this way may be any convenient dicarboxylic acid, typically one known to have low toxicity. The diacid may be of the general formula (3):

(3), wherein R$^3$ is an optionally substituted alkylene or alkenylene moiety, for example an optionally substituted C$_{1-10}$ alkylene or C$_{2-10}$ alkenylene moiety.

By alkenylene is meant an unsaturated hydrocarbyl moiety, which may be straight-chain, cyclic or branched (typically straight-chain unless the context dictates to the contrary) from which a hydrogen atom has been formally abstracted. Typically alkenylene groups will comprise from 2 to 25 carbon atoms, for example 2 to 10 carbon atoms, such as 2 to 6 carbon atoms. There may be one or more sites of unsaturation. Like alkyl and alkylene groups, alkenylene groups may be substituted, for example once, twice, or three times, e.g. once, i.e. formally replacing one or more hydrogen atoms of the group. Examples of such substituents are the same as those which may substitute alkyl or alkylene moieties.

In embodiments of the invention the alkylene or alkenylene moiety is unsubstituted. Examples of suitable diacids include the saturated diacids oxalic, malonic, succinic and glutaric; examples of unsaturated diacids include maleic, fumaric, trans-glutaconic and cis-glutaconic.

Linear triamines, suitable for reaction with dicarboxylic acids whereby to form exemplary polyfunctional molecules that serve as precursors to the linking moiety of the cationic lipids are, advantageously, of formula (4):

$$R^4N(H)R^5N(H)R^5N(H)R^4 \quad (4),$$

wherein:
each $R^4$ is independently an amine protecting group; and
each $R^5$ is independently an optionally substituted $C_{1-4}$ alkylene moiety.

The protecting groups $R^4$ may be different but will typically be the same. Any convenient protecting group may be employed. In the example section below, we describe use of the well-known 1-(4,4-dimethyl-2-6-dioxocyclohexylidene)ethyl (Dde) and fluororenylmethoxycarbonyl (Fmoc) groups. However, other appropriate protecting groups will be within the knowledge of those skilled in the art. *Protective groups in Organic Synthesis* (T W Greene and P G M Web, 3$^{rd}$ Ed, John Wiley & Sons, 1999) may be consulted for alternatives. The purpose of the $R^4$ groups is to permit selective reaction of the central secondary amines, e.g. of formula (4) with the dicarboxylic acids in the construction of the cationic lipids, as discussed in more detail below.

The $R^5$ groups may be independently an optionally substituted, but typically unsubstituted, $C_{1-4}$ alkylene group, for example methylene, ethylene, propylene or butylene. Typically, but not necessarily each $R^5$ will be the same. Compounds of formula (4) wherein each $R^5$ is ethylene or propylene, in particular ethylene, are particularly advantageous in a number of respects. Firstly, the unprotected triamines (i.e. absent the $R^4$ groups), diethylenetriamine and norspermidine respectively, are commercially available compounds (e.g. from Sigma-Aldrich and Fischer). Secondly, these compounds are relatively non-toxic. Thirdly, although not wishing to be bound by theory, we believe through modelling studies that the terminal amino groups are at an appropriate distance from one another to allow for advantageous disposition of the two lipophilic moieties, which may be attached to these terminal amines after $R^4$ group removal. This distance influences the hydrophobic interactions between the two lipophilic moieties. Where $R^5$ groups are ethylene and propylene in particular, these hydrophobic interactions advantageously affect the supramolecular properties of cationic lipids, e.g. the ability to complex polynucleotides such as DNA by forming relatively stable lipoplexes and the ability to induce endosomal disruption to promote transfection. Incorporating into cationic lipids the products resultant from reacting the dicarboxylic acids and triamines described above, i.e. as the components from which the linking moiety is made, affords cationic lipids having linking moieties of formula (5)

$$(HNR^5)_2NC(O)R^3C(O) \quad (5),$$

wherein $R^5$ and $R^3$ are as hereinbefore defined.

It is to be understood, analogously to the structural characterisation of formulae (1) and (2) above, that the two NH groups and C(O) depicted at the termini of the triradical defined by formula (5) each comprise part of the three amide groups connecting the linking moiety with the head group and the two lipophilic moieties. Thus, for example, in particular embodiments of the invention a linking moiety of formula (5) may be connected to a head group of formula (1) whereby to define a moiety of formula (6):

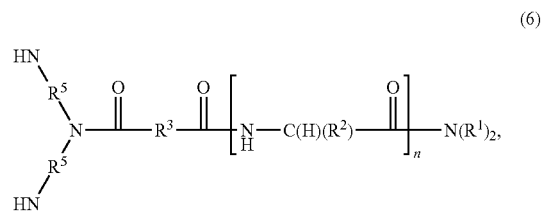

which depicts an amide-connected head group and linking moiety in cationic lipids of particular embodiments of the present invention, and wherein $R^5$, $R^3$, $R^2$, $R^1$ and n are as hereinbefore defined.

It will be understood that formula (6) defines diradicals with the two terminal NH groups depicted on the left-hand side of the formula forming part of the amide groups connecting the linking moiety with the two lipophilic moieties.

Lastly, embodiments of particular lipophilic moieties are discussed. Two lipophilic moieties are attached to the linking moiety of the cationic lipids of the invention through amide linkages.

According to certain embodiments, the two lipophilic moieties are independently of formulae (7) or (8)

$$R^6—N(H) \quad (7)$$

$$R^6—C(O) \quad (8)$$

wherein:
formulae (7) and (8) define radicals with the N(H) of formula (7) and C(O) of formula (8) forming part of the amide group that links the respective lipophilic moiety to the linking moiety; and $R^6$ represents a saturated or unsaturated fatty alkyl chain, optionally comprising fused cyclic regions whereby to form a polycyclic hydrocarbyl moiety.

In particular embodiments, $R^6$ may be decyl, undecyl, dodecyl, tridecyl, tetradecyl, pentadecyl, hexadecyl, octadecyl, 9-octadecenyl (also known as oleyl), eicosyl or tetraeicosyl; or may be generally represented as $CH_3(CH_2)_p$— wherein p is from 5 to 100, more usually 10 to 30, for example 12 to 24, optionally wherein one or more non-adjacent pairs of methylene groups (i.e. $CH_2CH_2$ units) are each replaced with CH=CH units whereby to define unsaturated fatty alkyl chains.

Formula (8) represents a saturated or unsaturated fatty acyl chain. For example, $R^6$—C(O)— may be decanoyl, undecanoyl, dodecanoyl, tridecanoyl, tetradecanoyl, pentadecanoyl, hexadecanoyl, octadecanoyl, 9-octadecenoyl, eicosanoyl or tetraeicosanoyl; or may be represented as $CH_3(CH_2)_qC(=O)$— wherein q is from 5 to 100, more usually 10 to 30, for example 12 to 24, optionally wherein one or more non-adjacent pairs of methylene groups (i.e. $CH_2CH_2$ units) are each replaced with CH=CH units whereby to define unsaturated fatty acyl chains.

An example of a $R^6$ moiety comprising a polycyclic hydrocarbyl moiety is a cholesteryl moiety.

According to particular embodiments of the invention each lipophilic moiety is the same and is of formula (8). This confers a number of advantages. For example, the lipophilic moieties may be derived from relatively non-toxic fatty acids, such as palmitic or oleic acid and afford such materials upon biodegradation.

It will be understood from the foregoing discussion that the N(H) of lipophilic moieties of formula (7) form part of the amide group connecting such lipophilic moieties to linking moieties with a terminal C(O) group and the C(O) group of lipophilic moieties of formula (8) form part of the amide group connecting such lipophilic moieties to linking moieties with a terminal NH group. According to particular embodiments of the latter, cationic lipids of the invention comprise two lipophilic moieties of formula (8) and a linking moiety of formula (5) whereby to provide a moiety of formula (9):

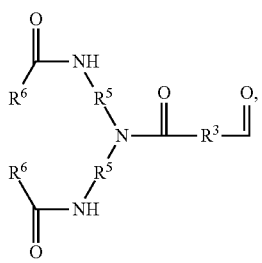

(9)

which depicts amide-connected lipophilic moieties and linking moieties in cationic lipids of particular embodiments of the present invention, and wherein $R^6$, $R^5$ and $R^3$ are as hereinbefore defined.

It will be understood that formula (9) defines a radical with the terminal C(O) group depicted on the right-hand side of the formula forming part of the amide group connecting the linking moiety with the head group.

According to other embodiments of the invention, the cationic lipids comprise two lipophilic moieties of formula (8) and a head group of formula (1) or formula (2), the head group and lipophilic moieties each being connected through amide linkages to the linking moiety. According to particular embodiments of these, the linking moiety is of formula (5) and the head group is of formula (1), whereby to define cationic lipids of the invention of formula (10)

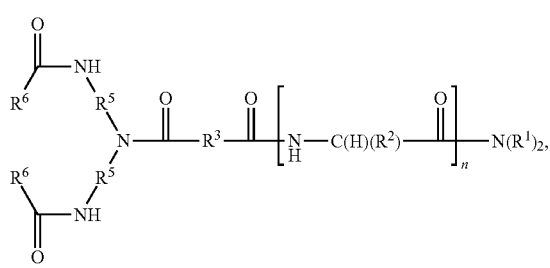

(10)

wherein $R^6$, $R^5$, $R^3$, $R^2$ and $R^1$ are as hereinbefore defined.

Essentially, by definition, and because of the presence of the hydrophobic, also referred to as lipophilic portion, lipids, including the cationic lipids of the present invention, are not considered to be soluble in water. Thus emulsions, rather than solutions, result when the cationic lipids of this invention are contacted with aqueous media. The cationic lipids of this invention are indeed typically supplied or prepared as aqueous emulsions or ethanolic solutions, which allow preparation of lipoplexes or other compositions by aliquoting a desired volume of the formulation.

The ethanolic solution may be absolute ethanol or mixtures of ethanol:water at different proportions (from 1:99 to 99:1, preferably 1:1 to 9:1).

The aqueous media with which the cationic lipids of this invention form emulsions may be water. However it may also be a solution, such as a HCl solution, a saline solution (e.g. comprising 100-200 mM NaCl; or a buffered solution such as phosphate-buffered saline (PBS)) mixed or not with ethanol. PBS typically comprises a mixture of dibasic and monobasic phosphates at a pH of about 7.0 to 7.6 with NaCl at a concentration appropriate to make the resultant solution isotonic with the media, e.g. cell suspension, with which it is to be contacted. Other aqueous media with which it may sometimes be desired to mix the cationic lipids of this invention include any culture medium, typically a serum-free culture medium. Such culture media are known to those skilled in the art and are both easy to prepare and commercially available. They include DMEM (DulbeccoNogt modified Eagle's minimal essential medium) and RPMI (Rosswell Park Memorial Institute medium).

The compounds of this invention are made, in broad terms, by reacting a molecule that provides the linking moiety of the cationic lipid, with other molecules so as to introduce the required lipophilic tail(s) and cationic head groups using solid-phase synthesis. Typically the linking moieties are initially synthesised in solution to introduce appropriate protecting groups (typically Dde or Fmoc). We find the Dde and Fmoc protection groups appropriate although, as discussed above, other groups will be evident to those skilled in the art.

Where synthesis is performed using a solid-phase approach, this typically starts with the attachment of Rink Amide linker (an acid-labile linker—(see Unciti-Broceta et al., Bioorg. Med. Chem., 2009, 17, 959-966) to amino-polystyrene resin. A coupling/deprotection protocol may then be followed (as described in more detail below), typically with initial coupling of the amino acid(s) followed by the linking moiety and finally the lipophilic moieties. The last step of such a synthesis is the acid-mediated cleavage of the resultant resin-bound molecules from the solid support to afford the desired, and pure, cationic lipids in salt form. Suitably the amino acids may be used with protection of the cationic moieties or precursors with acid-labile protecting groups. As such, upon resin cleavage under acid conditions, cationic charges are produced. According to the invention the linking moiety is attached to two lipophilic tails; as described above this may be derived from a saturated or unsaturated fatty acid, typically having from 10-24 carbon atoms, more typically 12 to 18 carbon atoms, and achieved by the reaction with a corresponding activated fatty acid, such as an acyl chloride, or by a DIC/HOBt activated derivative. Other methods of activation will be evident to those skilled in the art.

Examples of fatty acyl chains which may be attached to amino groups of the linking moieties, whereby to form amide linkages, are decanoyl, undecanoyl, dodecanoyl, tridecanoyl, tetradecanoyl, pentadecanoyl, hexadecanoyl, octadecanoyl, 9-octadecenoyl, eicosanoyl, tetraeicosanoyl, or cholesteryloxicarbonyl.

In one particular embodiment of the invention, one of the lipophilic moieties is or both of them are oleoyl (9-octadecenoyl), which is derived from oleic acid. Alternatively the lipophilic moieties may be as defined in accordance with one of the other possibilities described above which may likewise be introduced using chemical methodologies known to those skilled in the art.

As will be appreciated from the foregoing, the cationic lipids of the present invention are of particular use in the transfection of polynucleotides, such as DNA and RNA, and in particular DNA and siRNA, into cells. However, the utility of the cationic lipids of the present invention is not limited to their use in the preparation of lipoplexes for delivery of RNA and DNA into cells. Rather, the cationic lipids of the present invention may be used to envelope other macromolecules, such as proteins or polypeptides, for introduction into cells, or indeed to envelope small chemical compounds such as synthetic pharmaceuticals. Nevertheless, the particular affinity of cationic lipids for anionic compounds, including compounds such as nucleic acids, is the use to which cationic lipids are most suitable, and the utility of the cationic lipids of the invention in the preparation of lipoplexes comprising DNA and RNA is the use focused on herein.

The cationic lipids of the present invention may be used for transfection or other purposes, either in the presence or in the absence of co-helper lipids. They may be supplied either dried, or as aqueous emulsions as hereinbefore described. Such co-helper lipids, as is described hereinbefore, are typically neutral lipids and include DOPE, 1,2-dioleoyl-glycero-3-phosphocholine (DOPC) and cholesterol.

Where present, a co-helper lipid may be present in a wide range of ratios vis-à-vis the cationic lipid of this invention, for example molar ratios of about 1:10 to 10:1 of co-helper lipid: cationic lipid may be used, more usually from about 1:5 to 5:1, e.g. about 3:1 to 1:1. For example we find a 1:1 mixture comprising 1 molar equivalents of DOPE to a cationic lipid of this invention to be a generally useful ratio to use.

Where used for transfection, of RNA (e.g. siRNA) or DNA, the cationic lipid is typically present in excess over the amount of RNA or DNA present. For example the cationic lipid may be present in excesses of about 1.5 to 100:1, vis-à-vis the amount of DNA or RNA, e.g. about 2 to 50:1 or about 1.5 to 25:1, typically between about 1.5 and 6:1. These ratios relate to the ratio of positive charges to negative charges. The positive charges are provided by the cationic moieties present in the cationic lipids of this invention and the negative charges are provided by the ionised phosphate groups or other negative charges present in the polynucleotide, for example DNA or RNA. Thus, for example, if it is desired to form a lipoplex with a DNA comprising 510 phosphate groups, an excess of cationic lipid of this invention, wherein for example there are two cationic head group per molecule, requires more than 255 molar equivalents of such a cationic lipid to provide an excess of the number of cations (2×255). The ratios of the charges provided by the cationic lipids to the charges provided by polynucleotides are referred to herein as N/P ratios. We find useful N/P ratios with which to work, e.g. form lipoplexes, to be those in the range of 2/1 to 60/1, for example 1/1 to 50/1, e.g. 3/1 to 30/1. Useful ratios reported herein are 1.5/1, 3/1, 6/1 and 12/1. The N/P ratios referred to herein may also be used when using the quantities of co-helper lipids described herein, particularly in the immediately preceding paragraph.

The method of the present invention may be applied to in vitro and in vivo transfection of cells, particularly to transfection of eukaryotic cells or tissue such as animal cells, in particular mammalian cells, in particular human cells as well as other cells such as those of insects, plant, birds and fish. In this respect, it is noted for the avoidance of any doubt the references herein to singular forms such as "a" or "an" (e.g. "a cell") include the plural (e.g. "cells") unless the context clearly dictates to the contrary.

The method of the invention can thus be used to generate transfected cells or tissues capable of expressing useful gene products as a result of the DNA or RNA, in particular DNA, transfected, as well as having utility in the field of biotechnology and medical research, gene therapy and other medical applications, either in vivo or ex vivo. Such medical applications include cancer and cystic fibrosis treatment, and diagnostic methods.

The cells which may be transfected include a great variety of cells, including somatic and germ line cells, as well as embryonic, foetal, and adult cells. In one embodiment the cells may be stem cells, such as embryonic, adult or cancer stem cells. If the stem cells are human embryonic stem cells, it is to be appreciated that such cells can be obtained from a variety of sources without having to isolate the cells directly from an embryo. There are, for example, a great many embryonic stem cell lines which are available to the skilled addressee, such as from the NIH Human Embryonic Stem Cell registry.

The compounds of the invention are of particular use in the transfection of RNA and DNA into cells. Whilst the transfection into cells of any polynucleotide may be advantageous, transfection of plasmid DNA, optionally modified to provide antibiotic resistance, and the delivery of siRNA (small interfering RNA) are of particular utility in relation to biotechnological applications (e.g. in vitro gene transfection or gene silencing) and in gene therapy. The compositions described herein can be used to transfect a variety of polynucleotides, such as plasmid DNA, viral DNA, chromosomal fragments, antisense oligonucleotides, antisense phosphorothioate oligonucleotides, RNA molecules and ribozymes, or combinations thereof.

To demonstrate the utility of the cationic lipids of the present invention as in vitro transfection vectors, as is described in greater detail in the experimental section below, we demonstrate transfection into human tumoral HeLa, HEK293 and B16F10 cells of a plasmid DNA encoding for GFP, and a fluorescently-labelled siRNA. Our results demonstrate both effective transfection of the polynucleotides and high cell viability data towards the cell lines transfected.

The transfection methods can be performed in vitro, e.g., wherein the transfection composition is applied to cells in culture. Alternatively, the methods can be performed in vivo by applying the transfection composition to cells in vivo.

As used herein, the various forms of the term "transfect" (e.g., "transfecting", "transfected") are intended to refer to the process of introducing a polynucleotide molecule from an exterior location into the interior of a cell.

As used herein, the term "polynucleotide molecule" is intended to encompass molecules comprised of two or more covalently linked nucleotide bases, including deoxyribonucleic acid (DNA) molecules and ribonucleic acid (RNA) molecules. The nucleotides forming the polynucleotide molecule typically are linked to each other by phosphodiester linkages, although the term "polynucleotide molecule" is also intended to encompass nucleotides linked by other linkages, such as phosphorothioate linkages. Nonlimiting examples of polynucleotide molecules include plasmid DNA, viral DNA, chromosomal fragments, antisense oligonucleotides, antisense phosphorothioate oligonucleotides, RNA molecules (read as siRNA molecules) and ribozymes.

For gene therapy purposes, the polynucleotide(s) typically is an expression vector (described in further detail below) that encodes a protein to be provided for therapeutic benefit. The transfection method preferably is used to transfect eukaryotic cells, more preferably mammalian cells. The transfection method can be carried out in vitro, e.g., by applying the transfection composition to cells in culture. The time period for contacting the transfection composition with the cells in culture can be optimized by standard methods. A nonlimiting example of a transfection time in vitro is 48 hours, followed by washing the cells (e.g., with phosphate buffered saline). Alternatively, the transfection method can be carried out in vivo, by applying the transfection composition to cells in vivo. Typical target tissues for transfection in vivo include, for example, stomach, muscle, lungs, liver, epithelial cells, colon, uterus, breast, intestine, heart, kidney, prostate, skin, eye, brain, penile tissue and nasal tissue.

In certain embodiments the polynucleotide may be in the form of an expression vector encoding a protein(s) of therapeutic benefit. An expression vector comprises a polynucleotide in a form suitable for expression of the polynucleotide in cells to be transfected, which means that the recombinant expression vector includes one or more regulatory sequences, usually selected on the basis of the type of cells to be transfected, which is operatively linked to the polynucleotide to be expressed. Within a recombinant expression vector, "operably linked" is intended to mean that the polynucleotide of interest is linked to the regulatory sequence(s) in a manner which allows for expression of the polynucleotide (e.g., transcription/translation in a host cell when the vector is introduced into the host cell). The term "regulatory sequence" is intended to includes promoters, enhancers and other expression control elements (e.g., polyadenylation signals). Such regulatory sequences are well known in the art and are described, for example, in Goeddel; Gene Expression Technology Methods in Enzymology 185, Academic Press, San Diego, Calif. (1990). Regulatory sequences include those that direct constitutive expression of a polynucleotide in many types of host cell and those which direct expression of the polynucleotide only in certain host cells (e.g. tissue-specific regulatory sequences). It will be appreciated by those skilled in the art that the design of the expression vector may depend on such factors as the choice of the host cell to be transformed, the level of expression of protein desired, etc.

Examples of mammalian expression vectors include pMex-Neol, pCDM8 (Seed, B., (1987) Nature 329:840) and pMT2PC (Kaufman et al., (1987), EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. Alternatively, mammalian expression vectors capable of directing expression of a polynucleotide preferentially in a particular cell type can be used (i.e., an expression vector comprising tissue-specific regulatory elements) and are well known in the art.

The transfection methods of the present invention employing the compounds or compositions (such as those described above) of the present invention or mixtures thereof can be applied to in vitro and in vivo transfection of cells, particularly to transfection of eukaryotic cells or tissues including animal cells, human cells, insect cells, plant cells, avian cells, fish cells, mammalian cells and the like.

The methods of this invention can be used to generate transfected cells or tissues which express useful gene products. The methods of this invention can also be used as a step in the production of transgenic animals. The methods of this invention are useful in any therapeutic method requiring introducing of nucleic acids into cells or tissues. In particular, these methods are useful in cancer treatment, in in vivo and ex vivo gene therapy, and in diagnostic methods. See, for example, U.S. Pat. No. 5,589,466 to Feigner, et al. and U.S. patent application Ser. No. 08/450,555 filed on May 25, 1995 to Jessee, at al. The transfection compounds or compositions of this invention can be employed as research reagents in any transfection of cells or tissues done for research purposes.

Nucleic acids that can be transfected by the methods of this invention include DNA and RNA from any source comprising natural bases or non-natural bases, and include those encoding and capable of expressing therapeutic or otherwise useful proteins in cells or tissues, those which inhibit expression of nucleic acids in cells or tissues, those which inhibit enzymatic activity or activate enzymes, those which catalyze reactions (ribozymes), and those which function in diagnostic assays.

The compounds, compositions and methods provided herein can also be readily adapted in view of the disclosure herein to introduce biologically active macromolecules or substances other than nucleic acids, including, among others, polyamines, polyamine acids, polypeptides, proteins, biotin, and polysaccharides into cells. Other useful materials for example, therapeutic agents, diagnostic materials and research reagents, can be introduced into cells by the methods of this invention. In a preferred aspect, any nucleic acid vector may be delivered to or into a cell by the present invention.

This invention also includes transfection kits which include one or more of the compounds or compositions of the present invention or mixtures thereof. Particularly, the invention provides a kit comprising one or more of the compounds of the present invention and at least one additional component selected from the group consisting of a cell, cells, a cell culture media, a nucleic acid, a transfection enhancer and instructions for transfecting a cell or cells.

The polynucleotide molecules used in the present invention may be either single-stranded or double-stranded, may be linear or circular, e.g., a plasmid, and are either oligo- or polynucleotides. They may comprise as few as 15 bases or base pairs, or may include as many as 20 thousand bases or base pairs (20 kb). Since the transfer moiety is employed on a pro rata basis when added to the nucleic acid composition, practical considerations of physical transport will largely govern the upper limit on the size of nucleic acid compositions which can be utilized.

In addition to these naturally occurring materials, the nucleic acid compositions used in the present invention can also include synthetic compositions, i.e., nucleic acid analogs. These have been found to be particularly useful in antisense methodology, which is the complementary hybridization of relatively short oligonucleotides to single-stranded RNA or single-stranded DNA, such that the normal, essential functions of these intracellular nucleic acids are disrupted. See, e.g., Cohen, *Oligonucleotides: Antisense Inhibitors of Gene Expression*, CRC Press, Inc., Boca Raton, Fla. (1989).

The size, nature and specific sequence of the nucleic acid composition to be transferred to the target cell can be optimized for the particular application for which it is intended, and such optimization is well within the skill of the artisan in this field.

The polynucleotide molecules may serve as: 1) genetic templates for proteins that function as prophylactic and/or therapeutic immunizing agents; 2) replacement copies of defective, missing or non-functioning genes; 3) genetic templates for therapeutic proteins; 4) genetic templates for antisense molecules and as antisense molecules per se; or 5) genetic templates for ribozymes.

In the case of polynucleotide molecules which encode proteins, the polynucleotide molecules preferably comprise the necessary regulatory sequences for transcription and translation in the target cells of the individual animal to which they are delivered.

In the case of polynucleotide molecules which serve as templates for antisense molecules and ribozymes, such nucleic acid molecules may be linked to regulatory elements necessary for production of sufficient copies of the antisense and ribozyme molecules encoded thereby respectively.

The present invention can allow for transfer to target cells of a polynucleotide molecule that comprises a nucleotide sequence that either encodes a desired peptide or protein, or serves as a template for functional nucleic acid molecules. The desired protein or functional nucleic acid molecule may be any product of industrial, commercial or scientific interest, e.g., therapeutic agents including vaccines; foodstuffs and nutritional supplements; compounds of agricultural significance such as herbicides and plant growth regulants, insecticides, miticides, rodenticides, and fungicides; compounds useful in animal health such as parasiticides including nematocides; and so forth. The target cells are typically cultures of host cells comprising micro-organism cells such as bacteria and yeast, but may also include plant and mammalian cells. The cell cultures are maintained in accordance with fermentation techniques well known in the art, which maximize production of the desired protein or functional nucleic acid molecule, and the fermentation products are harvested and purified by known methods.

The present invention further relates to a method for the transfer of a polynucleotide molecule composition to the cells of an individual in an in vivo manner.

The nucleic acid molecule may be administered to the cells of said individual on either an in vivo or ex vivo basis, i.e., the contact with the cells of the individual may take place within the body of the individual in accordance with the procedures which are most typically employed, or the contact with the cells of the individual may take place outside the body of the individual by withdrawing cells which it is desired to treat from the body of the individual by various suitable means, followed by contacting of said cells with said nucleic acid molecule, followed in turn by return of said cells to the body of said individual.

The method of transferring a polynucleotide composition to the cells of an individual provided by the present invention, includes particularly a method of immunizing an individual against a pathogen. In this method, the polynucleotide composition administered to said cells, comprises a nucleotide sequence that encodes a peptide which comprises at least an epitope identical to, or substantially similar to an epitope displayed on said pathogen as antigen, and said nucleotide sequence is operatively linked to regulatory sequences. The nucleic acid molecule must, of course, be capable of being expressed in the cells of the individual.

The method of transferring a polynucleotide composition to the cells of an individual provided by the present invention, further includes methods of immunizing an individual against a hyperproliferative disease or an autoimmune disease. In such methods, the polynucleotide composition which is administered to the cells of the individual comprises a nucleotide sequence that encodes a peptide that comprises at least an epitope identical to or substantially similar to an epitope displayed on a hyperproliferative disease-associated protein or an autoimmune disease-associated protein, respectively, and is operatively linked to regulatory sequences. Here again, the nucleic acid molecule must be capable of being expressed in the cells of the individual.

Other aspects of the present invention relate to gene therapy. This involves compositions and methods for introducing polynucleotide molecules into the cells of an individual which are exogenous copies of genes which either correspond to defective, missing, non-functioning or partially functioning genes in the individual, or which encode therapeutic proteins, i.e., proteins whose presence in the individual will eliminate a deficiency in the individual and/or whose presence will provide a therapeutic effect on the individual. There is thus provided a means of delivering such a protein which is a suitable, and even preferred alternative to direct administration of the protein to the individual.

As used herein the term "desired protein" is intended to refer to peptides and proteins encoded by gene constructs used in the present invention, which either act as target proteins for an immune response, or as a therapeutic or compensating protein in gene therapy regimens.

Using the methods and compositions of the present invention, DNA or RNA that encodes a desired protein is introduced into the cells of an individual where it is expressed, thus producing the desired protein. The nucleic acid composition, e.g., DNA or RNA encoding the desired protein is generally linked to regulatory elements necessary for expression in the cells of the individual. Regulatory elements for DNA expression include a promoter and a polyadenylation signal. In addition, other elements, such as a Kozak region, may also be included in the polynucleotide composition.

Examples of promoters useful with the nucleic acid compositions used in the present invention, especially in the production of a genetic vaccine for humans, include but are not limited to, promoters from simian virus 40 (SV40), mouse mammary tumor Virus (MMTV) promoter, human immunodeficiency Virus (HIV) such as the HIV long terminal repeat (LTR) promoter, moloney virus, ALV, cytomegalovirus (CMV) such as the CMV immediate early promoter, Epstein Barr virus (EBV), Rous sarcoma virus (RSV), as well as promoters from human genes such as human actin, human myosin, human haemoglobin, human muscle creatine and human metalothionein.

Examples of polyadenylation signals useful with the nucleic acid compositions used in the present invention, especially in the production of a genetic vaccine for humans, include but are not limited to, SV40 polyadenylation signals and LTR polyadenylation signals. In particular, the SV40 polyadenylation signal which is in pCEP4 plasmid (Invitrogen, San Diego Calif.), referred to as the SV40 polyadenylation signal, may be used. In addition to the regulatory elements required for nucleic acid molecule expression, other elements may also be included in the DNA molecule. Such additional elements include enhancers. The enhancer may be selected from the group including but not limited to: human actin, human myosin, human haemoglobin, human muscle creatine, and viral enhancers such as those from CMV, RSV and EBV.

Nucleic acid compositions can be provided with mammalian origin of replication in order to maintain the construct extrachromosomally and produce multiple copies of the construct in the cell. Plasmids pCEP4 and pREP4 from Invitrogen (San Diego, Calif.) contain the EBV origin of replication and nuclear antigen EBNA-1 coding region, which produces high copy episomal replication without integration. In aspects of the invention relating to gene therapy, constructs with origins of replication including the necessary antigen for activation are preferred.

Antisense molecules and ribozymes may also be delivered to the cells of an individual by introducing a nucleic acid composition which acts as a template for copies of such active agents. These agents inactivate or otherwise interfere with the expression of genes that encode proteins whose presence is undesirable. Nucleic acid compositions which contain sequences that encode antisense molecules can be used to inhibit or prevent production of proteins within cells. Thus, production of proteins such as oncogene products can be eliminated or reduced. Similarly, ribozymes can disrupt gene expression by selectively destroying messenger RNA before it is translated into protein. In some embodiments, cells are treated according to the invention using nucleic acid compositions that encode antisense or ribozymes as part of a therapeutic regimen which involves administration of other therapeutics and procedures. Polynucleotide compositions encoding antisense molecules and ribozymes use similar vectors as those which are used when protein production is desired except that the coding sequence does not contain a start codon to initiate translation of RNA into protein.

Ribozymes are catalytic RNAs which are capable of self-cleavage or cleavage of another RNA molecule. Several different types of ribozymes, such as hammerhead, hairpin, Tetrahymena group I intron, ahead, and RNase P are known in the art; see S. Edgington, *Biotechnology* (1992) 10, 256-262. Hammerhead ribozymes have a catalytic site which has been mapped to a core of less than 40 nucleotides. Several ribozymes in plant viroids and satellite RNAs share a common secondary structure and certain conserved nucleotides. Although these ribozymes naturally serve as their own substrate, the enzyme domain can be targeted to another RNA substrate through base-pairing with sequences flanking the conserved cleavage site. This ability to custom design ribozymes has allowed them to be used for sequence-specific RNA cleavage; see G. Paolella et al., *EMBO* (1992), 1913-1919.) It will therefore be within the skill of one in the art to use different catalytic sequences from various types of ribozymes, such as the hammerhead catalytic sequence, and design them in the manner disclosed herein. Ribozymes can be designed against a variety of targets including pathogen nucleotide sequences and oncogenic sequences. Preferred embodiments include sufficient complementarity to specifically target the abl-bcr fusion transcript while maintaining efficiency of the cleavage reaction.

The present invention also provides pharmaceutical kits which comprise a container comprising a polynucleotide composition, and a container comprising a transfection agent of the present invention. Optionally, there is included in such kits excipients, carriers, preservatives and vehicles suitable for use in pharmaceutical compositions and known to those skilled in the art. The term pharmaceutical kit is also intended to include multiple inoculants used in the methods of the present invention. Such kits include separate containers comprising different inoculants and transfection agents. The pharmaceutical kits in accordance with the present invention are also contemplated to include a set of inoculants used in immunizing methods and/or therapeutic methods, as described above.

The invention is now illustrated by the non-limiting examples that follow below.

1. General Remarks

TLC was performed on silica plates using varying systems as stated. Plates were visualised under an UV lamp at 254 nm or by a ninhydrin test. $^1$H NMR spectra were recorded on a Bruker AC300 spectrometer operating at 250 MHz at 298K. Samples were dissolved in $CDCl_3$ or $CD_3OD$ as stated. Chemical shifts are quoted in parts per million relative to the solvent peak. Abbreviations for multiplicity are s, singlet, d, doublet, t, triplet, q, quadruplet and m, multiplet. All coupling constants were measured in Hz. Electrospray-mass spectroscopy spectra were recorded using an Agilent 1100 series VG platform Quadruple Electrospray Ionisation mass spectrometer model G1946B. Sonication was done using a Hilsonic water bath and flow cytometry using a BD FACS Aria flow cytometer. Organic solvents were supplied by Fisher Scientific and laboratory reagents by Sigma-Aldrich.

2. Synthesis of Linking Moieties 3, 4, 7 and 8

2.1. Synthesis of 3 and 4

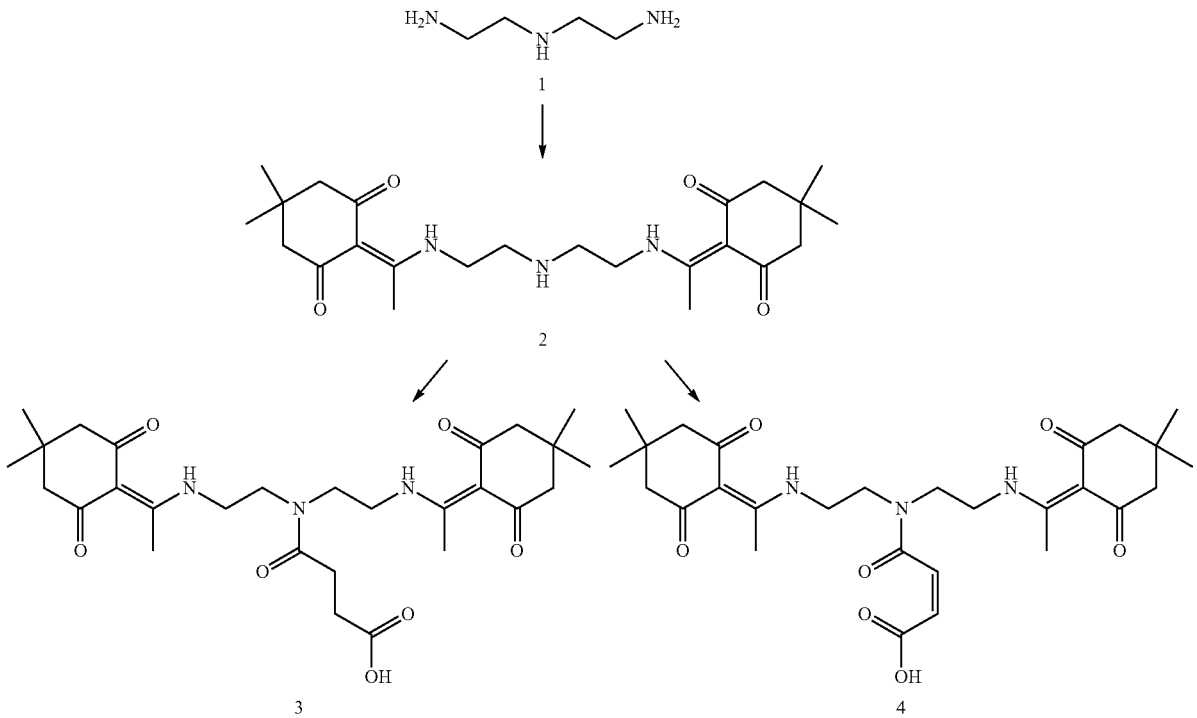

A solution of DdeOH (5 g, 27 mmol, 2 eq.) in DCM (5 mL) was added dropwise to a stirred solution of diethylenetriamine (1.41 g, 13.7 mmol, 1 eq.) and DCM (10 mL). The reaction mixture was stirred for 6 h at ambient temperature. The progress of the reaction was monitored by TLC (DCM:

MeOH 9:1). After 6 h the reaction was completed and the solvent was evaporated. The crude product 2 was then dissolved in DCM (5 mL) and either succinic anhydride (0.72 g, 7.2 mmol, 1 eq.) or maleic anhydride (0.7 g, 7.2 mmol, 1 eq.) (ES⁺): m/z (%): 530.2 (100) [M+H]⁺; HRMS (VE DAB) calcd for $C_{28}H_{40}N_3O_7$ 530.2866 ([M+H]⁺), mass found m/z: 530.2867

2.2. Synthesis of 7 and 8

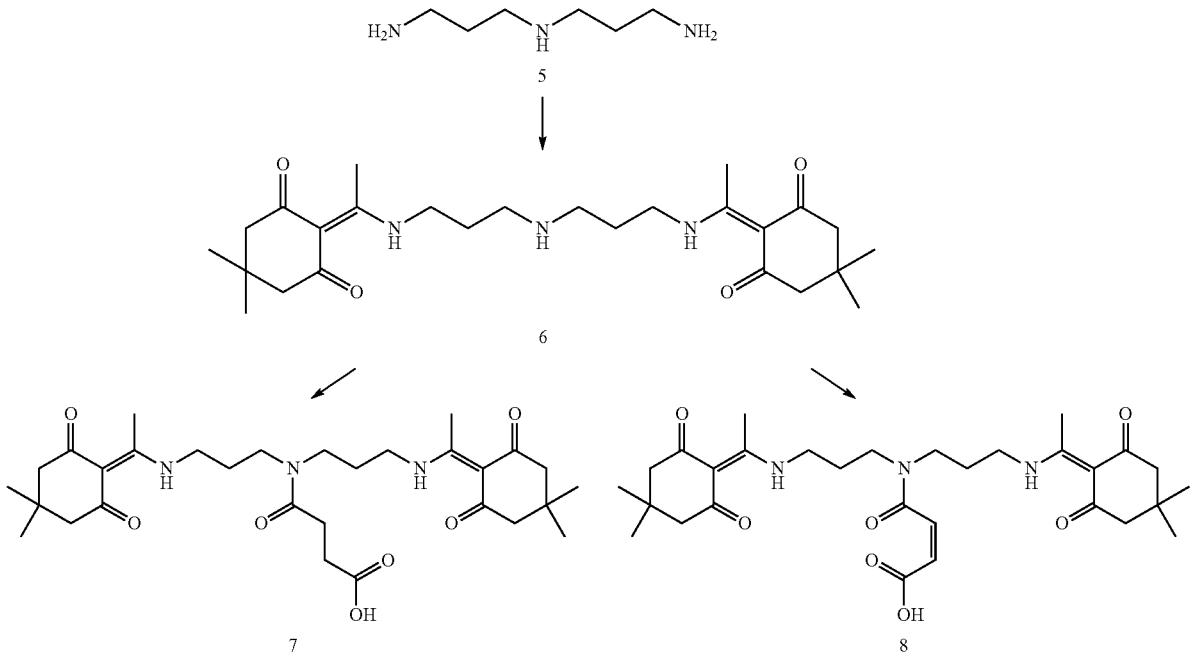

dissolved in DCM (5 mL) was added. The resulting mixture solution was stirred for 8 h at ambient temperature. The solvent was evaporated and crude product was purified by column chromatography, using DCM/MeOH (15:1) as eluting solvents, to afford compound the final compounds 3 (3.3 g, 92%) or 4 (3.4 g, 94%) as yellow solids.

N,N-Bis-(2-[1-(4,4-dimethyl-2,6-dioxo-cyclohexylidene)ethylamino]ethyl)succinamic acid (3)

$R_f$=0.6 (DCM/MeOH 9:1); m.p.=65-68° C.; IR: ν=2929 (O—H), 1725 (C=O), 1634 (C=C) cm⁻¹; NMR¹H (500 MHz, CDCl₃) δ=0.99 (s, 12H; 2×(CH₃)₂C(CH₂)₂), 2.32 (s, 4H; (CH₃)₂C(CH₂)₂), 2.34 (s, 4H; (CH₃)₂C(CH₂)₂), 2.51 (s, 3H; C=CCH₃), 2.54 (s, 3H; C=CCH₃), 2.60-2.63 (m, 2H; NHCH₂CH₂), 2.67-2.70 (m, 2H; NHCH₂CH₂), 3.55-3.58 (m, 2H; NCOCH₂), 3.64-3.68 (m, 6H; 2×NHCH₂CH₂, CH₂COOH); HPLC/ELSD 3.741 min (100%); MS (ES⁺): m/z (%): 532.2 (100) [M+H]⁺; HRMS (VE DAB) calcd for $C_{28}H_{42}N_3O_7$ 532.3022 ([M+]⁺), mass found m/z: 532.3022

N,N-Bis-(2-[1-(4,4-dimethyl-2,6-dioxo-cyclohexylidene)ethylamino]ethyl)maleamic acid (4)

$R_f$=0.76 (DCM/MeOH 4:1); m.p.=78° C.; IR ν=2929 (O—H), 1714 (C=O), 1632 (C=C) cm⁻¹; ¹H NMR (500 MHz, CDCl₃) δ=0.97 (s, 6H; (CH₃)₂C(CH₂)₂), 0.98 (s, 6H; (CH₃)₂C(CH₂)₂), 2.31 (s, 4H; (CH₃)₂C(CH₂)₂), 2.32 (s, 4H; (CH₃)₂C(CH₂)₂), 2.49 (s, 3H; C=CCH₃), 2.53 (s, 3H; C=CCH₃), 3.54-3.60 (m, 2H; NHCH₂CH₂N), 3.62-3.66 (m, 4H; 2×NHCH₂CH₂N), 3.71-3.75 (m, 2H; NHCH₂CH₂N), 6.11 (d, J 12, 1H; COCHCHCOOH), 6.60 (d, J 12, 1H; COCHCHCOOH); HPLC/ELSD 3.653 min (100%); MS A solution of DdeOH (5 g, 27 mmol, 2 eq.) in DCM (5 mL) was added dropwise to a stirred solution of norspermidine 5 (1.8 g, 13.7 mmol, 1 eq.) and DCM (10 mL). The reaction mixture was stirred for 6 h at ambient temperature. The progress of the reaction was monitored by TLC (DCM: MeOH 9:1). After 6 h the reaction was completed and the solvent was evaporated. The crude product 6 was dissolved in DCM (5 mL) and either succinic anhydride (0.7 g, 6.8 mmol, 1 eq.) or maleic anhydride (0.7 g, 6.8 mmol, 1 eq.) dissolved in DCM (5 mL) was added. The resulting mixture solution was stirred for 8 h at ambient temperature. The solvent was evaporated and crude product was purified by column chromatography, using DCM/MeOH (20:1) as eluting solvents, to afford the final compounds 7 (3.6 g, 93%) or 8 (3.5 g, 91%) as yellow solids.

N,N-Bis-(2-[1-(4,4-dimethyl-2,6-dioxo-cyclohexylidene)ethylamino]propyl)maleamic acid (7)

$R_f$=0.45 (DCM/MeOH 9:1); m.p. 68-70° C.; IR ν=2929 (O—H), 1725 (C=O), 1634 (C=C) cm⁻¹; ¹H-NMR (500 MHz, CDCl₃) δ=0.97 (s, 6H; (CH₃)₂C(CH₂)₂), 0.98 (s, 6H; (CH₃)₂C(CH₂)₂), 1.85-2.05 (s, 6H; NHCH₂CH₂CH₂N, 2×NHCH₂CH₂CH₂N), 2.31 (s, 4H; (CH₃)₂C(CH₂)₂), 2.32 (s, 4H; (CH₃)₂C(CH₂)₂), 2.49 (s, 3H; C=CCH₃), 2.53 (s, 3H; C=CCH₃), 2.63-2.67 (m, 2H; NHCH₂CH₂N), 3.34-3.44 (m, 8H; NCOCH₂, CH₂COOH, 2×NHCH₂CH₂CH₂N); HPLC/ELSD 3.932 min (100%); MS (ES⁺): m/z (%): 560.2 (100) [M+H]⁺; HRMS (VE DAB) calcd for $C_{30}H_{46}N_3O_7$ 560.3336 ([M+H]), mass found m/z: 560.3336.

N,N'-Bis-1,1-(4,4-dimethyl-2,6-dioxocyclohexylidene)ethyl-N-5-(1-carboxypropeno-2-yl)-norspermidine (8)

$R_f$=0.4 (DCM/MeOH 4:1); m.p. 48-50° C.; IR ν=2956 (O—H), 1707 (C=O), 1637 (C=C) cm$^{-1}$; $^1$H-NMR (500 MHz, CDCl$_3$) δ=1.00 (s, 6H; (CH$_3$)$_2$C(CH$_2$)$_2$), 1.02 (s, 6H; (CH$_3$)$_2$C(CH$_2$)$_2$), 1.97-2.04 (m, 4H; 2×NHCH$_2$CH$_2$CH$_2$N), 2.34 (d, 4H; (CH$_3$)$_2$C(CH$_2$)$_2$), 2.36 (d, 4H; (CH$_3$)$_2$C(CH$_2$)$_2$), 2.54 (s, 6H; 2×C=CCH$_3$), 3.42-3.46 (m, 2H; NHCH$_2$CH$_2$CH$_2$N), 3.50-3.58 (m, 6H; NHCH$_2$CH$_2$CH$_2$N, 2×NHCH$_2$CH$_2$CH$_2$N), 6.21 (d, J 12, 1 H; COCHCHCOOH), 6.57 (d, J 12, 1H; COCHCHCOOH); HPLC/ELSD 3.897 min (100%); MS (ES$^+$): m/z (%): 558.2 (100) [M+H]$^+$; HRMS (VE DAB) calcd for C$_{30}$H$_{44}$N$_3$O$_7$ 558.3179 ([M+H]$^+$), mass found m/z: 558.3175.

3. Solid-Phase Synthesis of Arginine-Containing Cationic Lipids (26a-j, 27a-j, 28a-j, 29a-j, 30a-j and 31a-j)

3.1. Synthesis of Resin with the Rink Linker

9

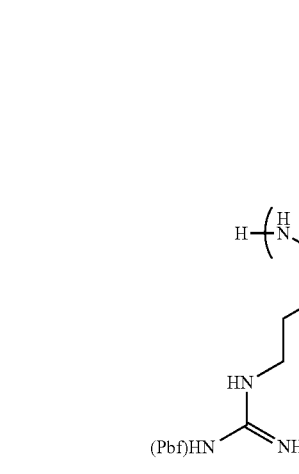

Fmoc-Rink-Amide Linker (3 eq., 0.3 mmol) was dissolved in DCM/DMF (2:1, 1.5 mL). DIC (3 eq., 0.3 mmol) and HOBt (3 eq., 0.3 mmol) were added and the mixture was left to stir for 5 min. This solution was added to aminomethyl polystyrene resin 9 (1.60 mmol/g, 60 mg) and microwave-irradiated at 60° C. for 20 min. The resulting resin was washed with DCM, DMF, MeOH, DMF and DCM (3×2 mL each) and then treated with a solution of 20 piperidine in DMF (2×10 min) to give resin 10, which was subsequently washed with DCM, DMF, MeOH, DMF and DCM (3×2 mL each).

3.2. Synthesis of Arginine Scaffold Resins

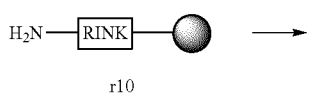

r10

r11 (n = 1)
r12 (n = 2)
r13 (n = 3)

The mono-arginine scaffold resin r11 was synthesized by the coupling of the resin r10 with a solution of Fmoc-L-arginine (Pbf)-OH (3 eq., 0.3 mmol), DIC (3 eq., 0.3 mmol) and HOBt (3 eq., 0.3 mmol) in DMF/DCM (2:1, 1.5 mL). The mixture was microwave-irradiated at 60° C. for 20 min. The resulting Fmoc-protected resin was washed with DCM, DMF, MeOH, DMF and DCM (3×2 mL each) and then treated with a solution of 20% piperidine in DMF (2×10 min). The resulting mono-arginine resin r11 was washed with DCM, DMF, MeOH, DMF and DCM (3×2 mL each). Repetition of this synthetic method once or twice afforded di- and tri-arginine scaffold resin r12 and r13.

3.3. Synthesis of Arginine Scaffold Resins with Linking Moiety

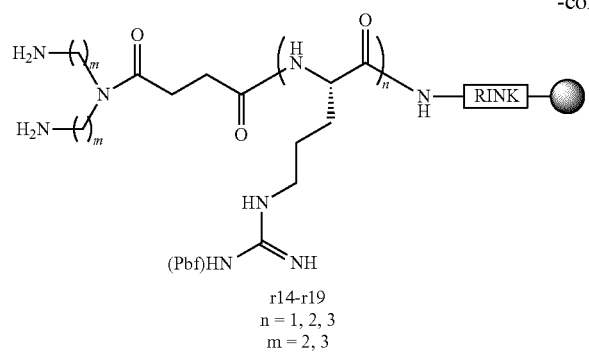

r14-r19
n = 1, 2, 3
m = 2, 3

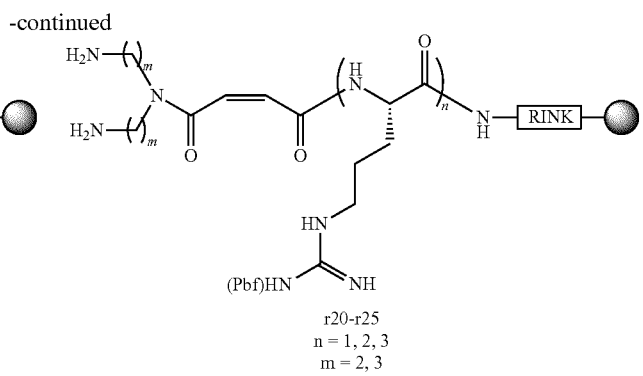

r20-r25
n = 1, 2, 3
m = 2, 3

The arginine scaffold resins r11-r13 were reacted with Dde-protected polyamines spacers 3, 4, 7 or 8 (3 eq., 0.3 mmol) using DIC (3 eq., 0.3 mmol) and HOBt (3 eq., 0.3 mmol) in DMF/DCM (2:1, 1.5 mL). The suspensions were microwave-irradiated at 60° C. for 20 min and washed with DCM, DMF, MeOH, DMF and DCM (3×2 mL each). The resulting resins were treated with a solution of 5% hydrazine (to deprotect) in DMF for 2 hours and washed with DCM, DMF, MeOH, DMF and DCM (3×2 mL each) to give amine free resins r14-r25.

3.4. Synthesis of Resin-Bound Arginine-Containing Cationic Lipids

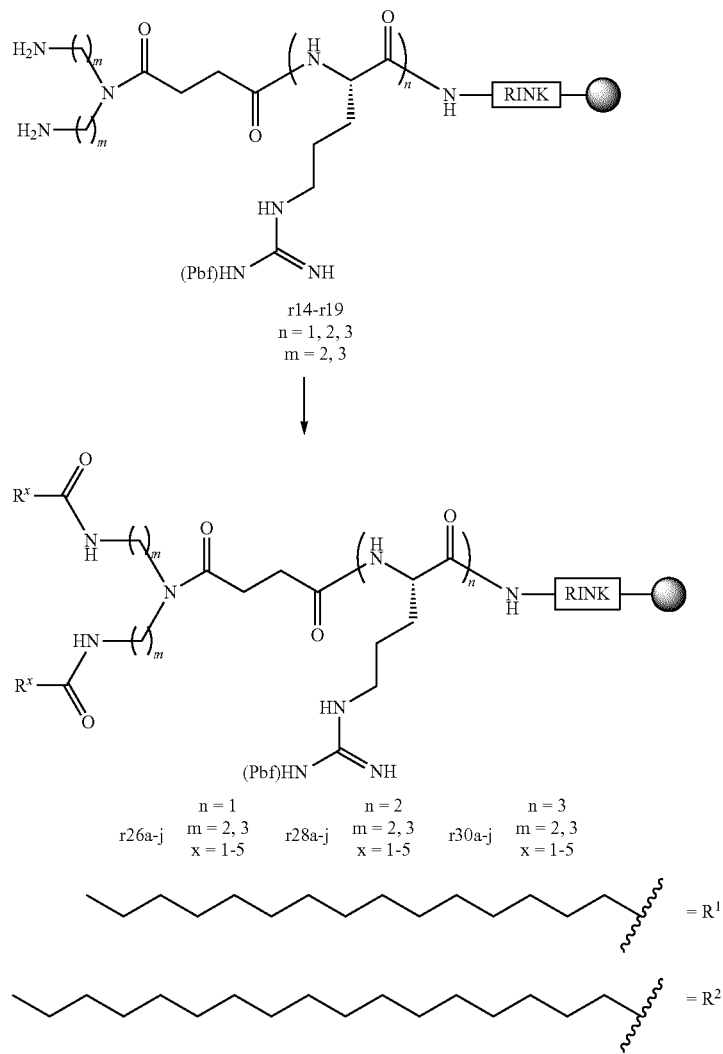

-continued
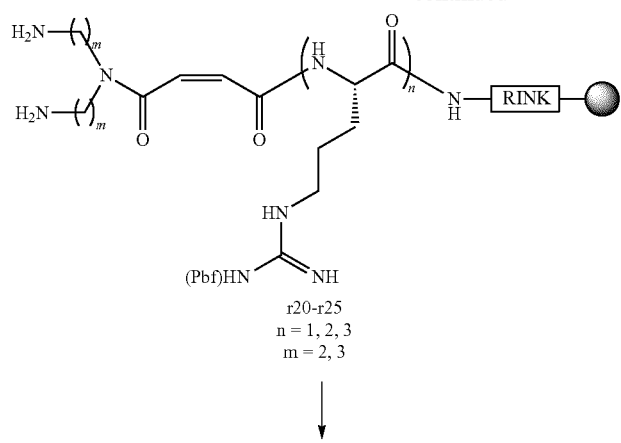
r20-r25
n = 1, 2, 3
m = 2, 3
↓
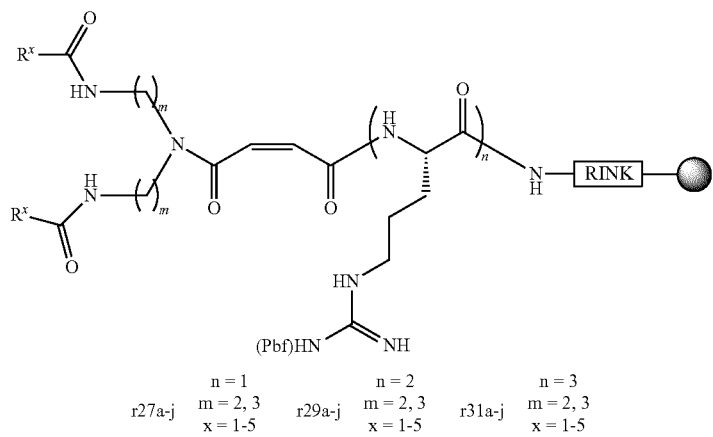
| | n = 1 | | n = 2 | | n = 3 |
|---|---|---|---|---|---|
| r27a-j | m = 2, 3 | r29a-j | m = 2, 3 | r31a-j | m = 2, 3 |
| | x = 1-5 | | x = 1-5 | | x = 1-5 |
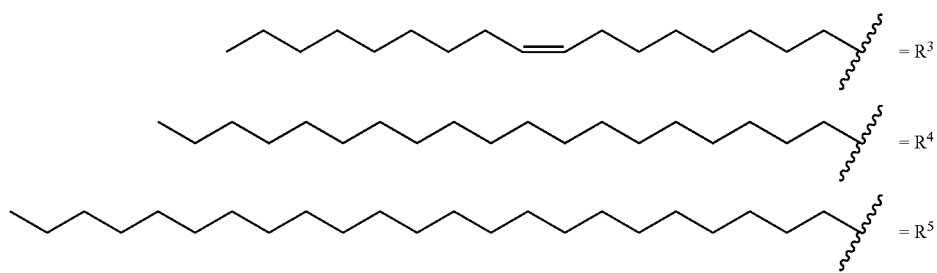

The resins were reacted with the corresponding fatty acid (3 eq, 0.3 mmol) using DIC (3 eq, 0.3 mmol) and HOBt (3 eq, 0.3 mmol) in DMF/DCM (2:1, 1.5 mL). The suspensions were microwave-irradiated at 60° C. for 20 min and the resulting resins were washed with DCM, DMF, MeOH, DMF and DCM (3×2 mL each) and dried under vacuum.
3.5. Cleavage of the Products 26a-j, 27a-j, 28a-j, 29a-j, 30a-j and 31a-j from the Resins.
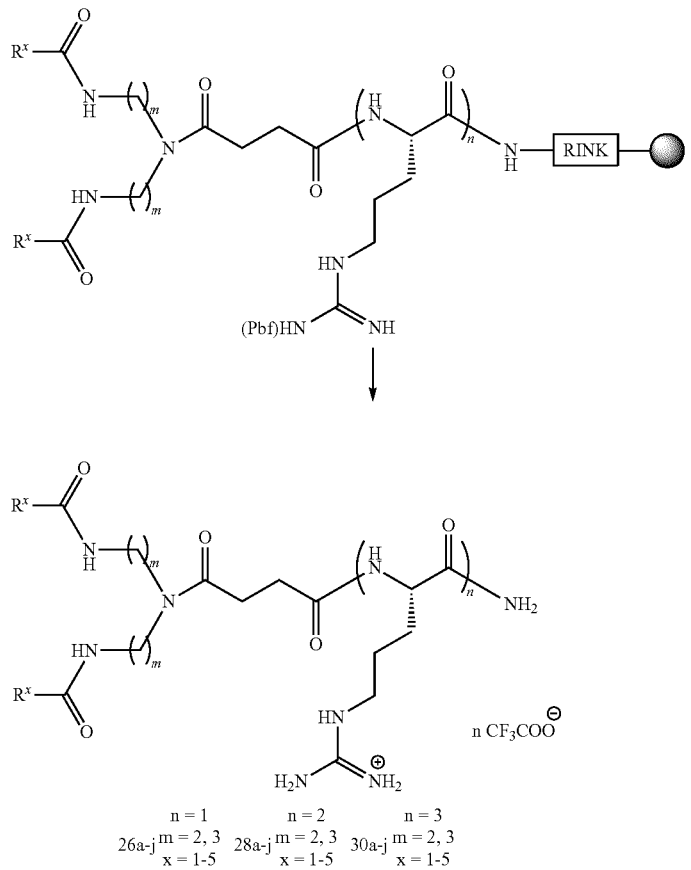
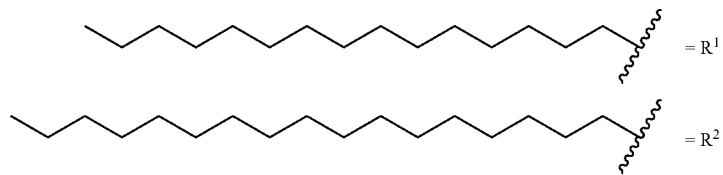
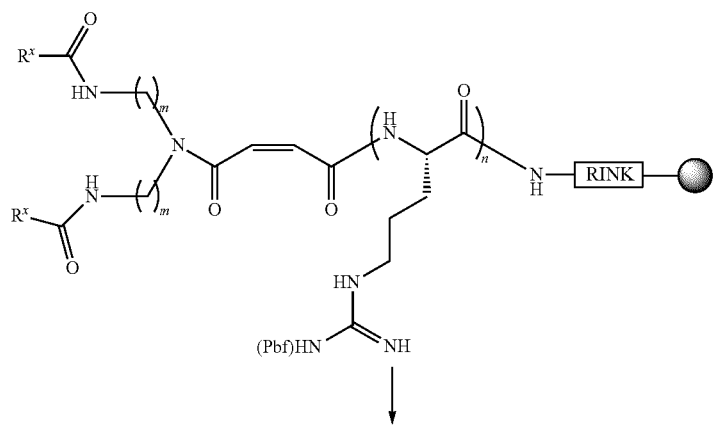

-continued

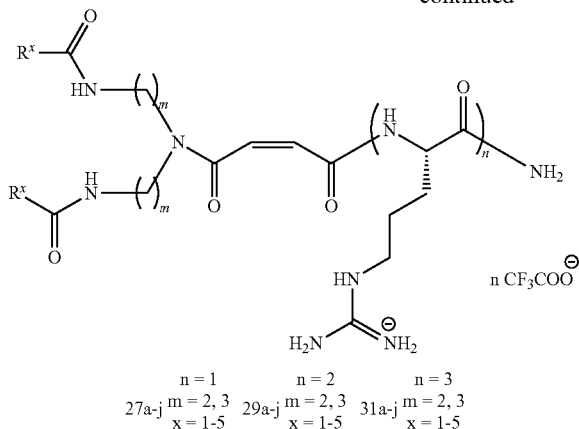

n = 1    n = 2    n = 3
27a-j m = 2, 3   29a-j m = 2, 3   31a-j m = 2, 3
       x = 1-5          x = 1-5          x = 1-5

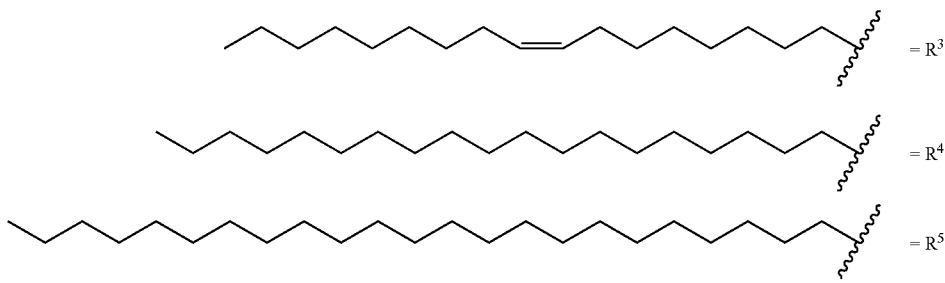

The resins were pre-swollen for 15 min in DCM and filtered. A solution of TFA/TIS/H$_2$O (95:2.5:2.5, 2 mL) was added to the resins and the suspensions were shaken for 2 h. The solvents were removed in vacuo. The resulting products were redissolved in DCM and precipitated with Et$_2$O. The resulting suspensions were centrifuged (8000 rpm for 6 min) and the solvent was removed using a pipette. The desired products were further dried under vacuum for 2 h.

TABLE 1

Cationic lipids generated.

General Formula

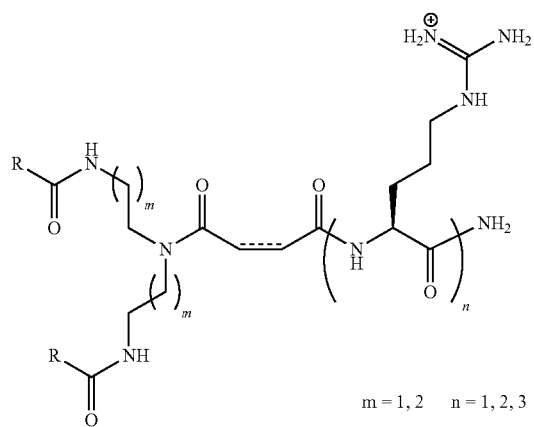

m = 1, 2    n = 1, 2, 3

TABLE 1-continued
Cationic Headgroups
A1
A2
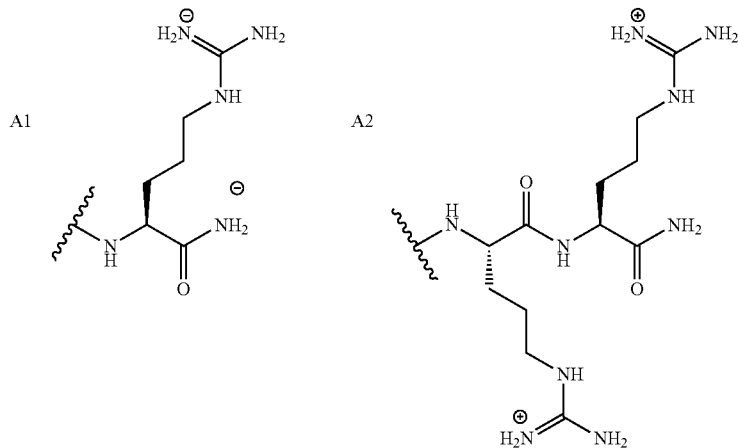
A3
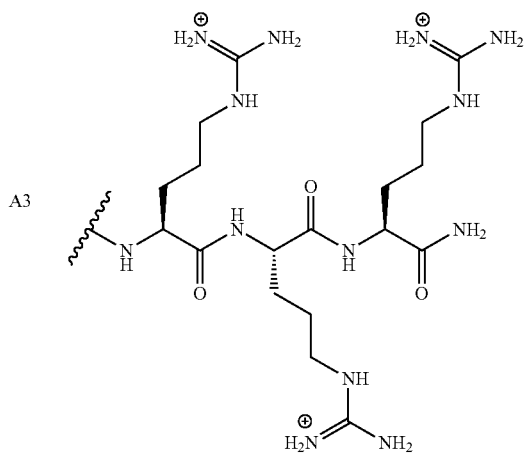
Fatty Tails
P 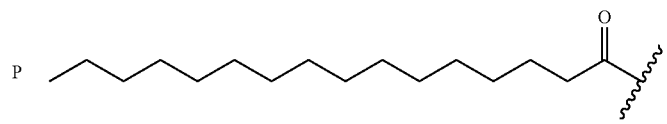
S 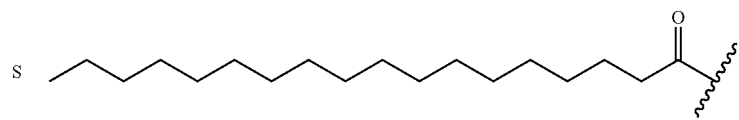
O 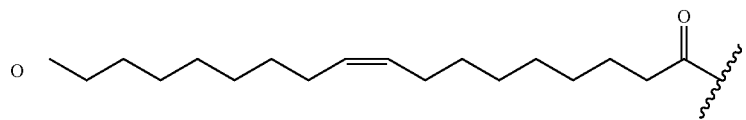

TABLE 1-continued
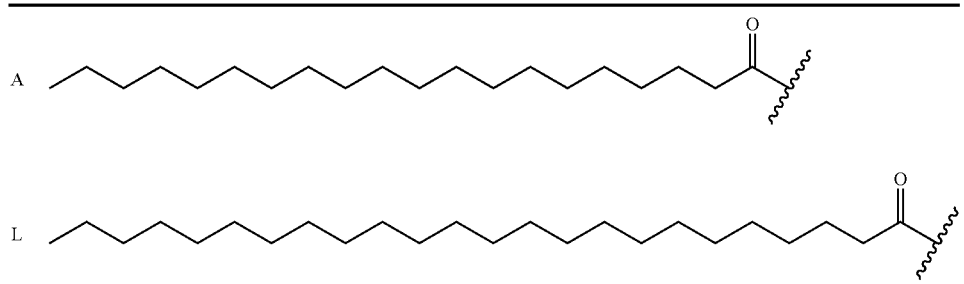
Linking Moieties
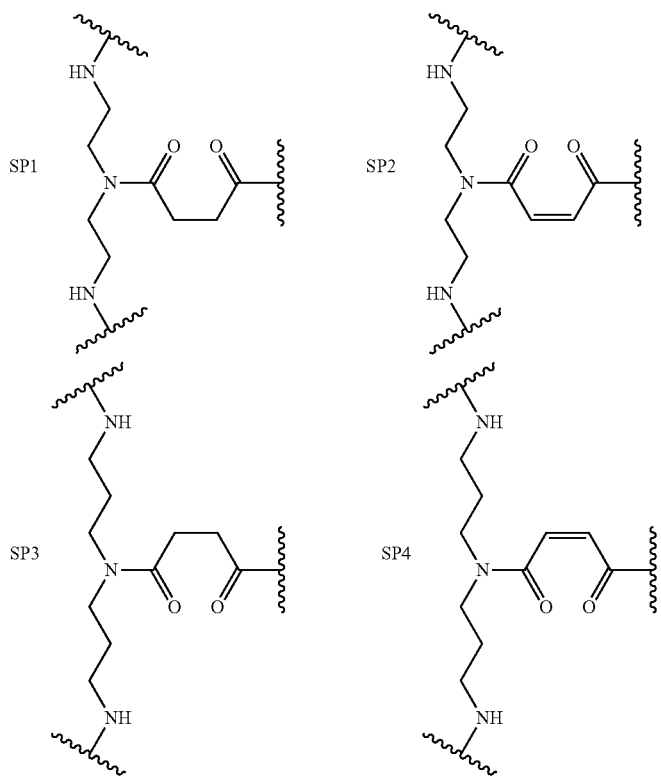
| Compound | Structure Code |
|---|---|
| 26a | A1-Sp1-P |
| 26b | A1-SP1-S |
| 26c | A1-Sp1-O |
| 26d | A1-Sp1-A |
| 26e | A1-Sp1-L |
| 27a | A1-Sp2-P |
| 27b | A1-Sp2-S |
| 27c | A1-Sp2-O |
| 27d | A1-Sp2-A |
| 27e | A1-Sp2-L |
| 26f | A1-Sp3-P |
| 26g | A1-Sp3-S |
| 26h | A1-Sp3-O |
| 26i | A1-Sp3-A |
| 26j | A1-Sp3-L |
| 27f | A1-Sp4-P |
| 27g | A1-Sp4-S |
| 27h | A1-Sp4-O |
| 27i | A1-Sp4-A |
| 27j | A1-Sp4-L |
| 28a | A2-Sp1-P |

TABLE 1-continued

| | |
|---|---|
| 28b | A2-Sp1-S |
| 28c | A2-Sp1-O |
| 28d | A2-Sp1-A |
| 28e | A2-Sp1-L |
| 29a | A2-Sp2-P |
| 29b | A2-Sp2-S |
| 29c | A2-Sp2-O |
| 29d | A2-Sp2-A |
| 29e | A2-Sp2-L |
| 28f | A2-Sp3-P |
| 28g | A2-Sp3-S |
| 28h | A2-Sp3-O |
| 28i | A2-Sp3-A |
| 28j | A2-Sp3-L |
| 29f | A2-Sp4-P |
| 29g | A2-Sp4-S |
| 29h | A2-Sp4-O |
| 29i | A2-Sp4-A |
| 29j | A2-Sp4-L |
| 30a | A3-Sp1-P |
| 30b | A3-Sp1-S |
| 30c | A3-Sp1-O |
| 30d | A3-Sp1-A |
| 30e | A3-Sp1-L |
| 31a | A3-Sp2-P |
| 31b | A3-Sp2-S |
| 31c | A3-Sp2-O |
| 31d | A3-Sp2-A |
| 31e | A3-Sp2-L |
| 30f | A3-Sp3-P |
| 30g | A3-Sp3-S |
| 30h | A3-Sp3-O |
| 30i | A3-Sp3-A |
| 30j | A3-Sp3-L |
| 31f | A3-Sp4-P |
| 31g | A3-Sp4-S |
| 31h | A3-Sp4-O |
| 31i | A3-Sp4-A |
| 31j | A3-Sp4-L |

3.6. Characterization of Compounds (26a-j, 27a-j, 28a-j, 29a-j, 30a-j and 31a-j)

26a (A1SP1P).

IR ν: 3291, 3194 (N—H), 2917 (C—H), 1627 (C=O); δ: 1543 (N—H) cm$^{-1}$. $^1$H NMR (360 MHz, DMSO) δ: 0.82-0.86 (m, 6H; O=CCH$_2$CH$_2$(CH$_2$)$_{12}$CH$_3$×2); 1.20 (s, 48H; O=CCH$_2$CH$_2$(CH$_2$)$_{12}$CH$_3$×2); 1.40-1.60 (m, 6H; O=CCCH$_2$CH$_2$(CH$_2$)$_{12}$CH$_3$×2, CHCH$_2$CH$_2$CH$_2$NH(HN=)CNH$_2$); 1.75 (m, 2H; CHCH$_2$CH$_2$CH$_2$NH(HN=)CNH$_2$); 1.95-2.15 (m, 4H; O=CCCH$_2$CH$_2$(CH$_2$)$_{12}$CH$_3$×2); 2.23-2.45 (m, 6H; NHC=OCH$_2$CH$_2$C=O, NHC=OCH$_2$CH$_2$C=O, CHCH$_2$CH$_2$CH$_2$NH(HN=)CNH$_2$); 3.0-3.8 (m, 8H; N(CH$_2$CH$_2$NHC=O)$_2$, N(CH$_2$CH$_2$NHC=O)$_2$); 4.2 (s, 1H; CHCH$_2$CH$_2$CH$_2$NH(HN=)CNH$_2$); 6.8-8.2 (m, 7H; NH$_2$C=O, NHCOCH$_2$CH$_2$C=O, N(CH$_2$CH$_2$NHC=O)$_2$, CHCH$_2$CH$_2$CH$_2$NH(HN=)CNH$_2$).

MS (ES$^+$): m/z (%): 835.6 MS (ES$^+$): m/z (%): 835.6 (100). HRMS calcd for C46H90N8O5 835.71069 ([M+H]$^+$), mass found m/z: 835.70830.

26b (A1SP1S).

IR ν: 3293, 3195 (N—H), 2916 (C—H), 1639 (C=O); δ: 1549 (N—H) cm$^{-1}$. $^1$H NMR (360 MHz, DMSO) δ: 0.84-0.94 (m, 6H; O=CCCH$_2$CH$_2$(CH$_2$)$_{14}$CH$_3$×2); 1.22 (br s, 56H; O=CCCH$_2$CH$_2$(CH$_2$)$_{14}$CH$_3$×2); 1.42-1.58 (m, 6H; O=CCCH$_2$CH$_2$(CH$_2$)$_{14}$CH$_3$×2, CHCH$_2$CH$_2$CH$_2$NH(HN=)CNH$_2$); 1.72-1.80 (m, 2H; CHCH$_2$CH$_2$CH$_2$NH(HN=)CNH$_2$); 1.98-2.13 (m, 4H; O=CCH$_2$CH$_2$(CH$_2$)$_{14}$CH$_3$×2) 2.22-2.46 (m, 6H; NHC=OCH$_2$CH$_2$C=O, NHC=OCH$_2$CH$_2$C=O, CHCH$_2$CH$_2$CH$_2$NH(HN=)CNH$_2$);); 3.1-3.4 (m, 8H; N(CH$_2$CH$_2$NHC=O)$_2$, N(CH$_2$CH$_2$NHC=O)$_2$); 4.1-5.0 (br s, 1H; CHCH$_2$CH$_2$CH$_2$NH(HN=)CNH$_2$); 6.6-8.2 (m, 7H; NH$_2$C=O, NHCOCH$_2$CH$_2$C=O, N(CH$_2$CH$_2$NHC=O)$_2$, CHCH$_2$CH$_2$CH$_2$NH(HN=)CNH$_2$).

MS (ES$^+$): m/z (%): 891.7 (100) [M+H]$^+$. HRMS calcd for C50H98N8O5 891.77329 ([M+H]$^+$), mass found m/z: 891.77160

26c (A1SP1O).

IR ν: 3342, 3209 (N—H), 2928 (C—H), 1627 (C=O); δ: 1551 (N—H) cm$^{-1}$. $^1$H NMR (360 MHz, CDCl$_3$) δ: 0.64-0.87 (m, 6H; (CH$_2$)$_6$CH$_3$×2); 0.91-1.70 (m, 46H; (CH$_2$)$_6$CH$_3$×2, O=CCH$_2$CH$_2$(CH$_2$)$_4$×2, O=CCH$_2$CH$_2$(CH$_2$)$_4$×2, CHCH$_2$CH$_2$CH$_2$NH(HN=)CNH$_2$); 1.79-2.23 (m, 14H; CHCH$_2$CH$_2$CH$_2$NH(HN=)CNH$_2$, H$_2$CHC=CHCH$_2$×2, O=CCH$_2$CH$_2$(CH$_2$)$_4$×2); 2.36-2.68 (m, 4H; NHC=OCH$_2$CH$_2$C=O, NHC=OCH$_2$CH$_2$C=O); 2.98-3.64 (m, 6H; CHCH$_2$CH$_2$CH$_2$NH(HN=)CNH$_2$, N(CH$_2$CH$_2$NHC=O)$_2$); 4.11-4.31 (m, 4H; N(CH$_2$CH$_2$NHC=O)$_2$); 4.89-4.98 (m, 1H; CHCH$_2$CH$_2$CH$_2$NH(HN=)CNH$_2$); 5.19-5.33 (m, 4H; H$_2$CHC=CHCH$_2$×2); 6.26-8.08; (m, 5H; NH$_2$C=O, NHCOCH$_2$CH$_2$C=O, N(CH$_2$CH$_2$NHC=O)$_2$); 9.20-9.59 (br s, 2H; CHCH$_2$CH$_2$CH$_2$NH(HN=)CNH$_2$).

MS (ES$^+$): m/z (%): 443.2 (100) [M+2H]$^{2+}$.

26d (A1SP1A).

IR ν: 3294, 3198 (N—H), 2916 (C—H), 1638 (C=O); δ: 1555 (N—H) cm$^{-1}$. $^1$H NMR (360 MHz, CDCl$_3$) δ 0.92 (t, J=7, 6H; O=CCH$_2$CH$_2$(CH$_2$)$_{16}$CH$_3$×2); 1.26 (br s, 64H; O=CCCH$_2$CH$_2$(CH$_2$)$_{16}$CH$_3$×2); 1.46-1.97 (m, 8H; O=CCCH$_2$CH$_2$(CH$_2$)$_{16}$CH$_3$, CHCH$_2$CH$_2$CH$_2$NH(HN=)CNH$_2$, CHCH$_2$CH$_2$CH$_2$NH(HN=)CNH$_2$); 2.10-2.45 (m,

6H;); 2.48-2.85 (m, 4H; O=CCCH$_2$CH$_2$(CH$_2$)$_{16}$CH$_3$×2, NHC=OCH$_2$CH$_2$C=O); 3.10-3.78 (m, 8H; N(CH$_2$CH$_2$NHC=O)$_2$, N(CH$_2$CH$_2$NHC=O)$_2$); 4.25-4.45 (br s, 1H; CHCH$_2$CH$_2$CH$_2$NH(HN=)CNH$_2$); 7.40-8.18 (m, 7H; NH$_2$C=O, NHCOCH$_2$CH$_2$C=O, N(CH$_2$CH$_2$NHC=O)$_2$, CHCH$_2$CH$_2$CH$_2$NH(HN=)CNH$_2$).

MS (ES$^+$): m/z (%): 947.8 (80) [M+H]$^+$. HRMS calcd for C$_{54}$H$_{106}$N$_8$O$_5$ 947.8358 ([M+H]+), mass found m/z: 947.8340

26e (A1SP1L).

IR ν: 3294, 3204 (N—H), 2916 (C—H), 1640 (C=O); δ: 1550 (N—H) cm$^{-1}$. $^1$H NMR (500 MHz, DMSO) δ: 0.94-1.02 (m, 6H; O=CCCH$_2$CH$_2$(CH$_2$)$_{20}$CH$_3$×2); 1.07-1.76 (m, 86H; O=CCCH$_2$CH$_2$(CH$_2$)$_{20}$CH$_3$×2, O=CCH$_2$CH$_2$(CH$_2$)$_{20}$CH$_3$×2, CHCH$_2$CH$_2$CH$_2$NH(HN=)CNH$_2$); 1.99-2.15 (m, 2H; CHCH$_2$CH$_2$CH$_2$NH(HN=)CNH$_2$); 3.01-3.16 (m, 4H; O=CCCH$_2$CH$_2$(CH$_2$)$_{20}$CH$_3$×2); 3.34-3.27 (m, 2H; NHC=OCH$_2$CH$_2$C=O); 3.41-3.52 (m, 2H; NHC=OCH$_2$CH$_2$C=O); (m, 2H; CHCH$_2$CH$_2$CH$_2$NH(HN=)CNH$_2$); 3.66-3.78 (m, 4H; N(CH$_2$CH$_2$NHC=O)$_2$); 3.84-3.97 (m, 4H; N(CH$_2$CH$_2$NHC=O)$_2$); 4.38-4.87 (m, 1H; CHCH$_2$CH$_2$CH$_2$NH(HN=)CNH$_2$); 6.73-8.58 (m, 7H; NH$_2$C=O, NHCOCH$_2$CH$_2$C=O, N(CH$_2$CH$_2$NHC=O)$_2$, CHCH$_2$CH$_2$CH$_2$NH(HN=)CNH$_2$).

MS (ES$^+$): m/z (%): 1059.9 (100) [M+H]$^+$. HRMS calcd for C$_{62}$H$_{122}$N$_8$O$_5$ 529.98027 ([M+H]+), mass found m/z: 529.98136

27a (A1-Sp2-P).

IR ν: 3292, 3191 (N—H), 2917 (C—H), 1633 (C=O); δ: 1547 (N—H) cm$^{-1}$. $^1$H NMR (360 MHz, DMSO) δ: 0.88 (t, J=7, 6H; O=CCH$_2$CH$_2$(CH$_2$)$_{12}$CH$_3$×2); 1.26 (br s, 48H; O=CCH$_2$CH$_2$(CH$_2$)$_{12}$CH$_3$×2); 1.36-1.63 (m, 6H; O=CCH$_2$CH$_2$(CH$_2$)$_{12}$CH$_3$, CHCH$_2$CH$_2$CH$_2$NH(HN=)CNH$_2$); 1.64-1.87 (m, 2H; CHCH$_2$CH$_2$CH$_2$NH(HN=)CNH$_2$); 1.98-2.10 (m, 1H; CHCH$_2$CH$_2$CH$_2$NH(HN=)CNH$_2$) 3.04-3.17 (m, 6H; O=CCCH$_2$CH$_2$(CH$_2$)$_{12}$CH$_3$×2, CHCH$_2$CH$_2$CH$_2$NH(HN=)CNH$_2$); 3.16-3.39 (m, 4H; N(CH$_2$CH$_2$NHC=O)$_2$); 3.84-3.97 (m, 4H; N(CH$_2$CH$_2$NHC=O)$_2$); 4.88-5.02 (m, 1H; CHCH$_2$CH$_2$CH$_2$NH(HN=)CNH$_2$); 6.40-8.49 (m, 9H; HNCOHC=CHCO, HNCOHC=CHCO, NH$_2$CO, N(CH$_2$CH$_2$NHC=O)$_2$, HNCOHC=CHCO, CHCH$_2$CH$_2$CH$_2$NH(HN=)CNH$_2$).

MS (ES$^+$): m/z (%): 883.7 (100) [M+H]$^+$. HRMS calcd for C$_{46}$H$_{88}$N$_8$O$_5$ 416.84725 ([M+2H]$^{2+}$), mass found m/z: 416.84602

27b (A1-Sp2-S).

IR ν: 3284, 3195 (N—H), 2918 (C—H), 1635 (C=O); δ: 1548 (N—H) cm$^{-1}$. $^1$H NMR (360 MHz, DMSO) δ: 0.88 (t, J=7, 6H; O=CCH$_2$CH$_2$(CH$_2$)$_{14}$CH$_3$×2); 1.26 (br s, 56H; O=CCCH$_2$CH$_2$(CH$_2$)$_{14}$CH$_3$×2); 1.37-1.59 (m, 6H; O=CCH$_2$CH$_2$(CH$_2$)$_{14}$CH$_3$, CHCH$_2$CH$_2$CH$_2$NH(HN=)CNH$_2$); 1.64-1.84 (m, 2H; CHCH$_2$CH$_2$CH$_2$NH(HN=)CNH$_2$); 1.96-2.00 (m, 1H; CHCH$_2$CH$_2$CH$_2$NH(HN=)CNH$_2$) 2.13 (m, 4H; O=CCH$_2$CH$_2$(CH$_2$)$_{14}$CH$_3$×2); 2.65-2.77 (m, 2H; CHCH$_2$CH$_2$CH$_2$NH(HN=)CNH$_2$); 3.00-3.33 (m, 4H; N(CH$_2$CH$_2$NHC=O)$_2$); 4.09-4.26 (m, 4H; N(CH$_2$CH$_2$NHC=O)$_2$); 4.75-5.39 (m, 1H; CHCH$_2$CH$_2$CH$_2$NH(HN=)CNH$_2$); 6.56-8.4 (m, 9H; HNCOHC=CHCO, HNCOHC=CHCO, NH$_2$CO, N(CH$_2$CH$_2$NHC=O)$_2$, HNCOHC=CHCO, CHCH$_2$CH$_2$CH$_2$NH(HN=)CNH$_2$).

MS (ES$^+$): m/z (%): 889.6 (100) [M+H]$^+$. HRMS calcd for C$_{50}$H$_{96}$N$_8$O$_5$ 444.87855 ([M+2H]$^{2+}$), mass found m/z: 444.87965

27c (A1-Sp2-O).

IR ν: 3284, 3194 (N—H), 2924 (C—H), 1633 (C=O); δ; 155048 (N—H) cm$^{-1}$. $^1$H NMR (360 MHz, CDCl$_3$) δ: 0.60-0.99 (m, 6H; (CH$_2$)$_6$CH$_3$×2); 0.95-1.82 (m, 48H; (CH$_2$)$_6$CH$_3$×2, O=CCH$_2$CH$_2$(CH$_2$)$_4$×2, O=CCH$_2$CH$_2$(CH$_2$)$_4$×2, CHCH$_2$CH$_2$CH$_2$NH(HN=)CNH$_2$, CHCH$_2$CH$_2$CH$_2$NH(HN=)CNH$_2$); 1.90-2.44 (m, 12H; H$_2$CHC=CHCH$_2$×2, O=CCH$_2$CH$_2$(CH$_2$)$_4$×2); 3.47-3.91 (m, 10H; CHCH$_2$CH$_2$CH$_2$NH(HN=)CNH$_2$, N(CH$_2$CH$_2$NHC=O)$_2$); 4.65-4.80 (m, 1H; CHCH$_2$CH$_2$CH$_2$NH(HN=)CNH$_2$); 5.29-5.44 (m, 4H; H$_2$CHC=CHCH$_2$×2); 6.07-7.69 (m, 7H; HNCOHC=CHCO, HNCOHC=CHCO, NH$_2$C=O, NHCOCH$_2$CH$_2$C=O, N(CH$_2$CH$_2$NHC=O)$_2$).

MS (ES$^+$): m/z (%): 444.2 (100) [M+2H]$^{2+}$.

27d (A1-Sp2-A).

IR ν: 3339, 3197 (N—H), 2917 (C—H), 1638 (C=O); δ: 1548 (N—H) cm$^{-1}$. $^1$H NMR (360 MHz, DMSO) δ: 0.84-0.92 (m, 6H; O=CCH$_2$CH$_2$(CH$_2$)$_{16}$CH$_3$×2); 1.26 (br s, 64H; O=CCCH$_2$CH$_2$(CH$_2$)$_{16}$CH$_3$×2); 1.37-1.85 (m, 8H; O=CCCH$_2$CH$_2$(CH$_2$)$_{16}$CH$_3$, CHCH$_2$CH$_2$CH$_2$NH(HN=)CNH$_2$, CHCH$_2$CH$_2$CH$_2$NH(HN=)CNH$_2$); 1.96-2.2 (m, 5H; CHCH$_2$CH$_2$CH$_2$NH(HN=)CNH$_2$, O=CCCH$_2$CH$_2$(CH$_2$)$_{16}$CH$_3$×2); 3.04-3.21 (m, 6H; CHCH$_2$CH$_2$CH$_2$NH(HN=)CNH$_2$, N(CH$_2$CH$_2$NHC=O)$_2$); 3.42-3.71 (m, 5H; N(CH$_2$CH$_2$NHC=O)$_2$, CHCH$_2$CH$_2$CH$_2$NH(HN=)CNH$_2$); 6.37-8.42 (m, 9H; HNCOHC=CHCO, HNCOHC=CHCO, NH$_2$CO, N(CH$_2$CH$_2$NHC=O, CHCH$_2$CH$_2$CH$_2$NH(HN=)CNH$_2$).

MS (ES$^+$): m/z (%): 945.7 (100) [M+H]$^+$.

27e (A1-Sp2-L).

IR ν: 3292, 3194 (N—H), 2916 (C—H), 1635 (C=O); δ: 1548 (N—H) cm$^{-1}$. $^1$H NMR (360 MHz, DMSO) δ: 0.84-0.92 (m, 6H; O=CCH$_2$CH$_2$(CH$_2$)$_{20}$CH$_3$×2); 1.26 (br s, 80H; O=CCCH$_2$CH$_2$(CH$_2$)$_{20}$CH$_3$×2); 1.37-1.62 (m, 6H; O=CCCH$_2$CH$_2$(CH$_2$)$_{20}$CH$_3$, CHCH$_2$CH$_2$CH$_2$NH(HN=)CNH$_2$); 1.64-1.80 (m, 2H; CHCH$_2$CH$_2$CH$_2$NH(HN=)CNH$_2$); 2.03-2.11 (m, 5H; CHCH$_2$CH$_2$CH$_2$NH(HN=)CNH$_2$, O=CCCH$_2$CH$_2$(CH$_2$)$_{20}$CH$_3$×2); 3.06-3.18 (m, 2H; CHCH$_2$CH$_2$CH$_2$NH(HN=)CNH$_2$); 3.79-4.74 (m, 9H; N(CH$_2$CH$_2$NHC=O)$_2$, N(CH$_2$CH$_2$NHC=O)$_2$, CHCH$_2$CH$_2$CH$_2$NH(HN=)CNH$_2$); 6.51-8.68 (m, 9H; HNCOHC=CHCO, HNCOHC=CHCO, NH$_2$CO, N(CH$_2$CH$_2$NHC=O)$_2$, HNCOHC=CHCO, CHCH$_2$CH$_2$CH$_2$NH(HN=)CNH$_2$).

MS (ES$^+$): m/z (%): 1057.8 (100) [M+H]$^+$.

26f (A1-Sp3-P).

IR ν: 3310, 3219 (N—H), 2916 (C—H), 1637 (C=O); δ: 1551 (N—H) cm$^{-1}$. $^1$H NMR (360 MHz, DMSO) δ: 0.84-0.92 (m, 6H; O=CCH$_2$CH$_2$(CH$_2$)$_{12}$CH$_3$×2); 1.17-1.35 (m, 48H; O=CCCH$_2$CH$_2$(CH$_2$)$_{12}$CH$_3$×2); 1.40-1.61 (m, 6H; O=CCCH$_2$CH$_2$(CH$_2$)$_{12}$CH$_3$×2, CHCH$_2$CH$_2$CH$_2$NH(HN=)CNH$_2$); 1.62-1.80 (m, 2H; CHCH$_2$CH$_2$CH$_2$NH(HN=)CNH$_2$); 1.97-2.16 (m, 9H; N(CH$_2$CH$_2$CH$_2$NHC=O)$_2$, CHCH$_2$CH$_2$CH$_2$NH(HN=)CNH$_2$, O=CCH$_2$CH$_2$(CH$_2$)$_{12}$CH$_3$×2); 2.75-2.78 (m, 2H; NHC=OCH$_2$CH$_2$C=O); 2.90-2.94 (m, 2H; NHC=OCH$_2$CH$_2$C=O); 2.96-3.04 (m, 2H; CHCH$_2$CH$_2$CH$_2$NH(HN=)CNH$_2$); 3.06-3.17 (m, 4H; CH$_2$CH$_2$CH$_2$NHC=O)$_2$); 3.18-3.33 (m, 4H; CH$_2$CH$_2$CH$_2$NHC=O)$_2$); 4.11-4.26 (m, 1H; CHCH$_2$CH$_2$CH$_2$NH(HN=)CNH$_2$); 6.88-8.32 (m, 7H; NH$_2$C=O, NHCOCH$_2$CH$_2$C=O, N(CH$_2$CH$_2$NHC=O)$_2$, CHCH$_2$CH$_2$CH$_2$NH(HN=)CNH$_2$).

MS (ES⁺): m/z (%): 863.7 (100) [M+H]⁺. HRMS calcd for C48H94N8O5 863.74199 ([M+H]⁺), mass found m/z: 863.74270

26g (A1-Sp3-S).

IR ν: 3309, 3196 (N—H), 2916 (C—H), 1637 (C=O); δ: 1550 (N—H) cm⁻¹. ¹H NMR (500 MHz, DMSO) δ: 0.84-0.91 (m, 6H; O=CCCH$_2$CH$_2$(CH$_2$)$_{14}$CH$_3$×2); 1.16-1.34 (m, 56H; O=CCCH$_2$CH$_2$(CH$_2$)$_{14}$CH$_3$×2); 1.43-1.60 (m, 4H; O=CCCH$_2$CH$_2$(CH$_2$)$_{14}$CH$_3$×2); 1.62-1.81 (m, 4H; CHCH$_2$CH$_2$CH$_2$NH(HN=)CNH$_2$, CHCH$_2$CH$_2$CH$_2$NH(HN=)CNH$_2$); 1.99-2.11 (m, 5H; N(CH$_2$CH$_2$CH$_2$NHC=O)$_2$, CHCH$_2$CH$_2$CH$_2$NH(HN=)CNH$_2$) 2.29-2.44 (m, 4H; O=CCCH$_2$CH$_2$(CH$_2$)$_{14}$CH$_3$×2); 2.59-2.72 (m, 2H; NHC=OCH$_2$CH$_2$C=O); 2.89-2.92 (m, 2H; NHC=OCH$_2$CH$_2$C=O); 2.95-3.01 (m, 2H; CHCH$_2$CH$_2$CH$_2$NH(HN=)CNH$_2$); 3.17-3.29 (m, 4H; CH$_2$CH$_2$CH$_2$NHC=O)$_2$); 3.73-5.08 (m, 5H; CH$_2$CH$_2$CH$_2$NHC=O)$_2$, CHCH$_2$CH$_2$CH$_2$NH(HN=)CNH$_2$); 6.91-8.25 (m, 7H; NH$_2$C=O, NHCOCH$_2$CH$_2$C=O, N(CH$_2$CH$_2$CH$_2$NHC=O)$_2$, CHCH$_2$CH$_2$CH$_2$NH(HN=)CNH$_2$).

MS (ES⁺): m/z (%): 919.7 (100) [M+H]⁺. HRMS calcd for C52H102N8O5 919.80459 ([M+H]⁺), mass found m/z: 919.8011.

26h (A1-Sp3-O).

IR ν: 3343, 3202 (N—H), 2926 (C—H), 1623 (C=O); δ: 1549 (N—H) cm⁻¹. ¹H NMR (360 MHz, DMSO) δ 64-0.86 (m, 6H; (CH$_2$)$_6$CH$_3$×2); 0.87-1.84 (m, 52H; (CH$_2$)$_6$CH$_3$×2, O=CCH$_2$CH$_2$(CH$_2$)$_4$×2, O=CCH$_2$CH$_2$(CH$_2$)$_4$×2, CHCH$_2$CH$_2$CH$_2$NH(HN=)CNH$_2$, CHCH$_2$CH$_2$CH$_2$NH(HN=)CNH$_2$, N(CH$_2$CH$_2$CH$_2$NHC=O)$_2$); 1.94-2.20 (m, 12H; H$_2$CHC=CHCH$_2$×2, O=CCH$_2$CH$_2$(CH$_2$)$_4$×2); 2.37-2.69 (m, 6H; NHC=OCH$_2$CH$_2$C=O, NHC=OCH$_2$CH$_2$C=O, CHCH$_2$CH$_2$CH$_2$NH(HN=)CNH); 2.75-3.43 (m, 4H; CH$_2$CH$_2$CH$_2$NHC=O)$_2$); 4.13-4.32 (m, 4H; CH$_2$CH$_2$CH$_2$NHC=O)$_2$); 4.88-5.01 (m, 1H; CHCH$_2$CH$_2$CH$_2$NH(HN=)CNH$_2$); 5.20-5.29 (m, 4H; H$_2$CHC=CHCH$_2$×2); 6.02-8.10 (m, 5H; NH$_2$C=O, NHCOCH$_2$CH$_2$C=O, N(CH$_2$CH$_2$NHC=O)$_2$); 8.91-9.40 (br s, 2H; CHCH$_2$CH$_2$CH$_2$NH(HN=)CNH$_2$). MS (ES⁺): m/z (%): 915.8 (100) [M+H]⁺.

HRMS calcd for C52H98N8O5 915.77329 ([M+H]⁺), mass found m/z: 915.7731

26i (A1-Sp3-A).

IR ν: 3308, 3206 (N—H), 2917 (C—H), 1637 (C=O); δ: 1551 (N—H) cm⁻¹. ¹H NMR (360 MHz, DMSO) δ: 0.87-0.95 (m, 6H; O=CCCH$_2$CH$_2$(CH$_2$)$_{16}$CH$_3$×2); 1.20-1.37 (m, 64H; O=CCCH$_2$CH$_2$(CH$_2$)$_{16}$CH$_3$×2); 1.49-1.53 (m, 6H; O=CCCH$_2$CH$_2$(CH$_2$)$_{16}$CH$_3$×2, CHCH$_2$CH$_2$CH$_2$NH(HN=)CNH$_2$); 1.58-1.68 (m, 2H; CHCH$_2$CH$_2$CH$_2$NH(HN=)CNH$_2$); 2.17-2.19 (m, 8H; N(CH$_2$CH$_2$CH$_2$NHC=O)$_2$, O=CCCH$_2$CH$_2$(CH$_2$)$_{16}$CH$_3$×2); 2.17-2.19 (m, 2H; NHC=OCH$_2$CH$_2$C=O); 2.23-2.24 (m, 2H; NHC=OCH$_2$CH$_2$C=O); 3.00-3.03 (m, 2H; CHCH$_2$CH$_2$CH$_2$NH(HN=)CNH$_2$); 3.09-3.12 (m, 4H; CH$_2$CH$_2$CH$_2$NHC=O)$_2$); 3.17-3.51 (m, 4H; CH$_2$CH$_2$CH$_2$NHC=O)$_2$); 4.32-4.45 (m, 1H; CHCH$_2$CH$_2$CH$_2$NH(HN=)CNH$_2$); 8.14-8.15 (m, 2H; CHCH$_2$CH$_2$CH$_2$NH(HN=)CNH$_2$).

MS (ES⁺): m/z (%): 975.7 (100) [M+H]⁺. HRMS calcd for C56H110N8O5 975.86719 ([M+H]⁺), mass found m/z: 975.8655

26j (A1-Sp3-L).

IR ν: 3309, 3204 (N—H), 2916 (C—H), 1637 (C=O); δ: 1557 (N—H) cm⁻¹. ¹H NMR (360 MHz, DMSO) δ: 0.87-0.95 (m, 6H; O=CCCH$_2$CH$_2$(CH$_2$)$_{16}$CH$_3$×2); 1.20-1.37 (m, 64H; O=CCCH$_2$CH$_2$(CH$_2$)$_{16}$CH$_3$×2); 1.49-1.53 (m, 6H; O=CCCH$_2$CH$_2$(CH$_2$)$_{16}$CH$_3$×2, CHCH$_2$CH$_2$CH$_2$NH(HN=)CNH$_2$); 1.58-1.68 (m, 2H; CHCH$_2$CH$_2$CH$_2$NH(HN=)CNH$_2$); 2.17-2.19 (m, 8H; N(CH$_2$CH$_2$CH$_2$NHC=O)$_2$, O=CCCH$_2$CH$_2$(CH$_2$)$_{16}$CH$_3$×2); 2.17-2.19 (m, 2H; NHC=OCH$_2$CH$_2$C=O); 2.23-2.24 (m, 2H; NHC=OCH$_2$CH$_2$C=O); 3.00-3.03 (m, 2H; CHCH$_2$CH$_2$CH$_2$NH(HN=)CNH$_2$); 3.09-3.12 (m, 4H; CH$_2$CH$_2$CH$_2$NHC=O)$_2$); 3.17-3.51 (m, 4H; CH$_2$CH$_2$CH$_2$NHC=O)$_2$); 4.32-4.45 (m, 1H; CHCH$_2$CH$_2$CH$_2$NH(HN=)CNH$_2$); 8.14-8.15 (m, 2H; CHCH$_2$CH$_2$CH$_2$NH(HN=)CNH$_2$).

MS (ES⁺): m/z (%): 1087.9 (100) [M+H]⁺. HRMS calcd for C64H126N8O5 362.66377 ([M+3H]³⁺), mass found m/z: 362.66429

27f (A1-Sp4-P).

IR ν 3309, 3203 (N—H), 2917 (C—H), 1638 (C=O); δ: 1553 (N—H) cm⁻¹. ¹H NMR (360 MHz, CDCl$_3$) δ: 0.79 (t, J=7, 6H; O=CCCH$_2$CH$_2$(CH$_2$)$_{12}$CH$_3$×2); 1.07-1.24 (m, 48H; O=CCCH$_2$CH$_2$(CH$_2$)$_{12}$CH$_3$×2); 1.41-1.54 (m, 8H; O=CCCH$_2$CH$_2$(CH$_2$)$_{12}$CH$_3$, CHCH$_2$CH$_2$CH$_2$NH(HN=)CNH$_2$); 1.95-2.32 (m, 2H; CHCH$_2$CH$_2$CH$_2$NH(HN=)CNH$_2$); 2.79-2.83 (m, 12H; N(CH$_2$CH$_2$CH$_2$NHC=O)$_2$, CHCH$_2$CH$_2$CH$_2$NH(HN=)CNH$_2$, O=CCH$_2$CH$_2$(CH$_2$)$_{12}$CH$_3$×2); 2.85-2.88 (m, 2H; CHCH$_2$CH$_2$CH$_2$NH(HN=)CNH$_2$); 2.92-3.29 (m, 4H; N(CH$_2$CH$_2$CH$_2$NHC=O)$_2$); 4.16-4.38 (m, 5H; N(CH$_2$CH$_2$CH$_2$NHC=O)$_2$, CHCH$_2$CH$_2$CH$_2$NH(HN=)CNH$_2$); 7.03-7.20 (m, 4H; HNCOHC=CHCO, HNCOHC=CHCO, NH$_2$CO); 7.95-8.0 (m, 3H; HNCOHC=CHCO, N(CH$_2$CH$_2$NHC=O)$_2$); 8.99-9.38 (m, 2H; CHCH$_2$CH$_2$CH$_2$NH(HN=)CNH$_2$).

MS (ES⁺): m/z (%): 861.7 (100) [M+H]⁺. HRMS calcd for C48H92N8O5 861.72634 ([M+H]⁺), mass found m/z: 861.72490

27g (A1-Sp4-S).

IR ν: 3309, 3199 (N—H), 2917 (C—H), 1636 (C=O); δ: 1550 (N—H) cm⁻¹. ¹H NMR (360 MHz, CDCl$_3$) δ: 0.93 (t, J=7, 6H; O=CCCH$_2$CH$_2$(CH$_2$)$_{14}$CH$_3$×2); 1.07-1.41 (m, 56H; O=CCCH$_2$CH$_2$(CH$_2$)$_{14}$CH$_3$×2); 1.45-1.53 (m, 4H; O=CCH$_2$CH$_2$(CH$_2$)$_{14}$CH$_3$); 1.54-1.68 (m, 8H; CHCH$_2$CH$_2$CH$_2$NH(HN=)CNH$_2$, CHCH$_2$CH$_2$CH$_2$NH(HN=)CNH$_2$, N(CH$_2$CH$_2$CH$_2$NHC=O)$_2$); 2.06-2.36 (m, 4H; O=CCCH$_2$CH$_2$(CH$_2$)$_{14}$CH$_3$×2); 2.92-2.97 (m, 2H; CHCH$_2$CH$_2$CH$_2$NH(HN=)CNH$_2$); 3.00-3.48 (m, 4H; N(CH$_2$CH$_2$CH$_2$NHC=O)$_2$); 4.35-4.48 (m, 5H; N(CH$_2$CH$_2$CH$_2$NHC=O)$_2$, CHCH$_2$CH$_2$CH$_2$NH(HN=)CNH$_2$); 6.32-9.23 (m, 9H; HNCOHC=CHCO, HNCOHC=CHCO, NH$_2$CO, HNCOHC=CHCO, N(CH$_2$CH$_2$NHC=O)$_2$, CHCH$_2$CH$_2$CH$_2$NH(HN=)CNH$_2$).

MS (ES⁺): m/z (%): 917.7 (100) [M+H]⁺. HRMS calcd for C52H100N8O5 917.78894 ([M+H]⁺), mass found m/z: 917.7874

27h (A1-Sp4-O).

IR ν: 3293, 3208 (N—H), 2925 (C—H), 1625 (C=O); δ: 1553 (N—H) cm⁻¹. ¹H NMR (360 MHz, CDCl$_3$) δ: 0.79-0.97; (m, 6H; O=CCCH$_2$CH$_2$(CH$_2$)$_{12}$CH$_3$×2); 0.99-1.84 (m, 52H; (CH$_2$)$_6$CH$_3$×2, O=CCH$_2$CH$_2$(CH$_2$)$_4$×2, O=CCH$_2$CH$_2$(CH$_2$)$_{12}$CH$_3$, CHCH$_2$CH$_2$CH$_2$NH(HN=)CNH$_2$, CHCH$_2$CH$_2$CH$_2$NH(HN=)CNH$_2$, N(CH$_2$CH$_2$CH$_2$NHC=O)$_2$); 1.91-2.35 (m, 12H; H$_2$CHC=CHCH$_2$×2, O=CCH$_2$CH$_2$(CH$_2$)$_4$×2); 2.85-3.48 (m, 10H; CHCH$_2$CH$_2$CH$_2$NH(HN=)CNH$_2$, N(CH$_2$CH$_2$CH$_2$NHC=O)$_2$, N(CH$_2$CH$_2$CH$_2$NHC=O)$_2$); 4.31-4.45 (m, 1H; CHCH$_2$CH$_2$CH$_2$NH(HN=)CNH$_2$); 5.31-5.43 (m, 4H; H$_2$CHC=CHCH$_2$×2); 6.39-8.19 (m, 6H; HNCOHC=CHCO, NH$_2$CO, HNCOHC=CHCO,

N(CH$_2$CH$_2$NHC=O)$_2$); 8.89-9.31 (br s, 2H; CHCH$_2$CH$_2$CH$_2$NH(HN=)CNH$_2$).

MS (ES$^+$): m/z (%): 457.5 (100) [M+2H]$^{2+}$.

27i (A1-Sp4-A).

IR ν: 3307, 3201 (N—H), 2916 (C—H), 1638 (C=O); δ: 1551 (N—H) cm$^{-1}$. $^1$H NMR (360 MHz, CDCl$_3$) δ 0.92 (t, J=7, 6H; O=CCCH$_2$CH$_2$(CH$_2$)$_{16}$CH$_3$×2); 1.19-1.39 (m, 64H; O=CCCH$_2$CH$_2$(CH$_2$)$_{16}$CH$_3$×2); 1.55-1.68 (m, 4H; O=CCH$_2$CH$_2$(CH$_2$)$_{16}$CH$_3$); 1.55 (m, 2H; CHCH$_2$CH$_2$CH$_2$NH(HN=)CNH$_2$); 1.70-1.92 (m, 2H; CHCH$_2$CH$_2$CH$_2$NH(HN=)CNH$_2$); 1.86 (m, 4H; N(CH$_2$CH$_2$CH$_2$NHC=O)$_2$); 2.09-2.14 (m, 4H; O=CCH$_2$CH$_2$(CH$_2$)$_{16}$CH$_3$×2); 2.21-2.37 (m, 2H; CHCH$_2$CH$_2$CH$_2$NH(HN=)CNH$_2$); 2.92-2.96 (m, 4H; N(CH$_2$CH$_2$CH$_2$NHC=O)$_2$); 3.13-3.52 (5H; N(CH$_2$CH$_2$CH$_2$NHC=O)$_2$, CHCH$_2$CH$_2$CH$_2$NH(HN=)CNH$_2$); 6.54-6.80 (m, 2H; HNCOHC=CHCO, HNCOHC=CHCO); 6.51-6.53 (m, 2H; NH$_2$CO); 8.70-9.01 (br s 2H; CHCH$_2$CH$_2$CH$_2$NH(HN=)CNH$_2$).

MS (ES$^+$): m/z (%): 973.8 (100) [M+H]$^+$. HRMS calcd for C$_{56}$H$_{108}$N$_8$O$_5$ 486.92550 ([M+2H]$^{2+}$), mass found m/z: 486.92347.

27j (A1-Sp4-L).

IR ν: 3309 (N—H), 2916 (C—H), 1637 (C=O); δ: 1553 (N—H) cm$^{-1}$. $^1$H NMR (360 MHz, DMSO) δ: 0.95-1.01 (m, 6H; O=CCH$_2$CH$_2$(CH$_2$)$_{20}$CH$_3$×2); 1.15-1.28 (m, 80H; O=CCCH$_2$CH$_2$(CH$_2$)$_{20}$CH$_3$×2); 1.37-1.39 (m, 4H; O=CCH$_2$CH$_2$(CH$_2$)$_{20}$CH$_3$); 1.94-1.96 (m, 2H; CHCH$_2$CH$_2$CH$_2$NH(HN=)CNH$_2$); 2.06-2.11 (m, 10H; CHCH$_2$CH$_2$CH$_2$NH(HN=)CNH$_2$, N(CH$_2$CH$_2$CH$_2$NHC=O)$_2$, O=CCCH$_2$CH$_2$(CH$_2$)$_{20}$CH$_3$×2); 2.84-2.91 (m, 6H; CHCH$_2$CH$_2$CH$_2$NH(HN=)CNH$_2$, N(CH$_2$CH$_2$CH$_2$NHC=O)$_2$); 3.33-3.43 (5H; N(CH$_2$CH$_2$CH$_2$NHC=O)$_2$, CHCH$_2$CH$_2$CH$_2$NH(HN=)CNH$_2$); 6.92-8.63 (m, 9H; HNCOHC=CHCO, HNCOHC=CHCO, NH$_2$CO, HNCOHC=CHCO, N(CH$_2$CH$_2$NHC=O)$_2$, CHCH$_2$CH$_2$CH$_2$NH(HN=)CNH$_2$).

MS (ES$^+$): m/z (%): 1085.7 (100) [M+H]$^+$.

28a (A2-Sp1-P).

IR ν: 3287, 3193 (N—H), 2922 (C—H), 1630 (C=O); δ: 1542 (N—H) cm$^{-1}$. $^1$H NMR (360 MHz, CDCl$_3$) 0.81-0.99 (m, 6H; O=CCH$_2$CH$_2$(CH$_2$)$_{12}$CH$_3$×2); 1.03-1.41 (m, 48H; O=CCCH$_2$CH$_2$(CH$_2$)$_{12}$CH$_3$×2); 1.43-1.67 (m, 12H; O=CCH$_2$CH$_2$(CH$_2$)$_{12}$CH$_3$×2, CHCH$_2$CH$_2$CH$_2$NH(HN=)CNH$_2$×2, CHCH$_2$CH$_2$CH$_2$NH(HN=)CNH$_2$×2); 2.08-2.30 (m, 8H; O=CCCH$_2$CH$_2$(CH$_2$)$_{12}$CH$_3$×2, NHC=OCH$_2$CH$_2$C=O, NHC=OCH$_2$CH$_2$C=O); 3.03-3.69 (m, 12H; CHCH$_2$CH$_2$CH$_2$NH(HN=)CNH$_2$×2, N(CH$_2$CH$_2$NHC=O)$_2$, N(CH$_2$CH$_2$NHC=O)$_2$); 4.20-4.51 (m, 2H; CHCH$_2$CH$_2$CH$_2$NH(HN=)CNH$_2$×2); 6.36-9.02 (m, 10H; NH$_2$C=O, NHCOCH$_2$CH$_2$C=O, N(CH$_2$CH$_2$NHC=O)$_2$, NHCO, CHCH$_2$CH$_2$CH$_2$NH(HN=)CNH$_2$×2). MS (ES$^+$): m/z (%): 496.5 (100) [M+2H]$^{2+}$. HRMS calcd for C$_{52}$H$_{102}$N$_{12}$O$_6$ 991.81181 ([M+H]$^+$), mass found m/z: 991.8098.

28b (A2-Sp1-S).

IR ν: 3291, 3192 (N—H), 2916 (C—H), 1628 (C=O); δ: 1541 (N—H) cm$^{-1}$. $^1$H NMR (360 MHz, DMSO) 0.82-0.92 (m, 6H; O=CCH$_2$CH$_2$(CH$_2$)$_{14}$CH$_3$×2); 1.20-1.34 (m, 56H; O=CCCH$_2$CH$_2$(CH$_2$)$_{14}$CH$_3$×2); 1.41-1.60 (m, 8H; O=CCH$_2$CH$_2$(CH$_2$)$_{14}$CH$_3$×2, CHCH$_2$CH$_2$CH$_2$NH(HN=)CNH$_2$×2); 1.69-1.81 (m, 10H; CHCH$_2$CH$_2$CH$_2$NH(HN=)CNH$_2$×2, O=CCH$_2$CH$_2$(CH$_2$)$_{14}$CH$_3$×2, NHC=OCH$_2$CH$_2$C=O); 3.02-3.36 (m, 14H; NHC=OCH$_2$CH$_2$C=O, CHCH$_2$CH$_2$CH$_2$NH(HN=)CNH$_2$×2, N(CH$_2$CH$_2$NHC=O)$_2$, N(CH$_2$CH$_2$NHC=O)$_2$); 4.12-4.25 (m, 2H; CHCH$_2$CH$_2$CH$_2$NH(HN=)CNH$_2$×2); 6.47-8.29 (m, 10H; NH$_2$C=O, NHCOCH$_2$CH$_2$C=O, N(CH$_2$CH$_2$NHC=O)$_2$, NHCO, CHCH$_2$CH$_2$CH$_2$NH(HN=)CNH$_2$×2). MS (ES$^+$): m/z (%): 524.5 (100) [M+2H]$^{2+}$. HRMS calcd for C$_{56}$H$_{110}$N$_{12}$O$_6$ 1047.87441 ([M+H]$^+$), mass found m/z: 1047.8740

28c (A2-Sp1-O).

IR ν: 3338, 3197 (N—H), 2925 (C—H), 1628 (C=O); a 1547 (N—H) cm$^{-1}$. $^1$H NMR (360 MHz, CDCl$_3$) δ: 0.79-1.00 (m, 6H; (CH$_2$)$_6$CH$_3$×2); 1.02-1.83 (m, 52H; (CH$_2$)$_6$CH$_3$×2, O=CCH$_2$CH$_2$(CH$_2$)$_4$×2, O=CCH$_2$CH$_2$(CH$_2$)$_4$×2, CHCH$_2$CH$_2$CH$_2$NH(HN=)CNH$_2$×2, CHCH$_2$CH$_2$CH$_2$NH(HN=)CNH$_2$×2); 1.88-2.35 (m, 14H; H$_2$CHC=CHCH$_2$×2, O=CCH$_2$CH$_2$(CH$_2$)$_4$×2, NHC=OCH$_2$CH$_2$C=O); 3.02-3.91 (m, 6H; NHC=OCH$_2$CH$_2$C=O, CHCH$_2$CH$_2$CH$_2$NH(HN=)CNH$_2$×2); 4.18-4.45 (m, 4H; N(CH$_2$CH$_2$NHC=O)$_2$); (4H; N(CH$_2$CH$_2$NHC=O)$_2$); 5.01-5.18 (m, 2H; CHCH$_2$CH$_2$CH$_2$NH(HN=)CNH$_2$×2); 5.31-5.44 (m, 4H; H$_2$CHC=CHCH$_2$×2); 6.22-8.28 (m, 6H; NH$_2$C=O, NHCOCH$_2$CH$_2$C=O, N(CH$_2$CH$_2$NHC=O)$_2$, NHCO); 8.90-9.42 (br s, 4H; CHCH$_2$CH$_2$CH$_2$NH(HN=)CNH$_2$×2).

MS (ES$^+$): m/z (%): 522.5 (100) [M+2H]$^{2+}$. HRMS calcd for C$_{56}$H$_{106}$N$_{12}$O$_6$ 521.92128 ([M+2H]$^{2+}$), mass found m/z: 521.91816

28d (A2-Sp1-A).

IR ν: 3352, 3202 (N—H), 2916 (C—H), 1628 (C=O); δ: 1540 (N—H) cm$^{-1}$. $^1$H NMR (500 MHz, DMSO) 0.76-0.94 (m, 6H; O=CCH$_2$CH$_2$(CH$_2$)$_{16}$CH$_3$×2); 0.95-1.85 (m, 76H; O=CCCH$_2$CH$_2$(CH$_2$)$_{16}$CH$_3$×2, O=CCH$_2$CH$_2$(CH$_2$)$_{16}$CH$_3$×2, CHCH$_2$CH$_2$CH$_2$NH(HN=)CNH$_2$×2, CHCH$_2$CH$_2$CH$_2$NH(HN=)CNH$_2$×2); 1.97-2.10 (m, 2H; CHCH$_2$CH$_2$CH$_2$NH(HN=)CNH$_2$×2) 2.96-3.41 (m, 12H; O=CCCH$_2$CH$_2$(CH$_2$)$_{16}$CH$_3$×2, NHC=OCH$_2$CH$_2$C=O, NHC=OCH$_2$CH$_2$C=O, CHCH$_2$CH$_2$CH$_2$NH(HN=)CNH$_2$×2); 3.87-4.87 (m, 8H; N(CH$_2$CH$_2$NHC=O)$_2$, N(CH$_2$CH$_2$NHC=O)$_2$); 5.73-5.81 (m, 2H; CHCH$_2$CH$_2$CH$_2$NH(HN=)CNH$_2$×2); 6.68-8.35 (m, 10H; NH$_2$C=O, NHCOCH$_2$CH$_2$C=O, N(CH$_2$CH$_2$NHC=O)$_2$, NHCOCHCH$_2$CH$_2$CH$_2$NH(HN=)CNH$_2$×2).

MS (ES$^+$): m/z (%): 552.5 (100) [M+2H]$^{2+}$. HRMS calcd for C$_{60}$H$_{118}$N$_{12}$O$_6$ 1103.93701 ([M+H]$^+$), mass found m/z: 1103.9338.

28e (A2-Sp1-L).

IR ν: 3352, 3206 (N—H), 2916 (C—H), 1628 (C=O); δ: 1545 (N—H) cm$^{-1}$. $^1$H NMR (500 MHz, DMSO) 0.79-0.92 (m, 6H; O=CCCH$_2$CH$_2$(CH$_2$)$_{20}$CH$_3$×2); 1.10-1.36 (m, 80H; O=CCCH$_2$CH$_2$(CH$_2$)$_{20}$CH$_3$×2); 1.33-1.83 (m, 12H; O=CCCH$_2$CH$_2$(CH$_2$)$_{20}$CH$_3$×2, CHCH$_2$CH$_2$CH$_2$NH(HN=)CNH$_2$×2, CHCH$_2$CH$_2$CH$_2$NH(HN=)CNH$_2$×2); 1.96-2.18 (m, 2H; CHCH$_2$CH$_2$CH$_2$NH(HN=)CNH$_2$×2) 2.31-2.45 (m, 4H; O=CCH$_2$CH$_2$(CH$_2$)$_{20}$CH$_3$×2); 3.02-3.16 (m, 2H; NHC=OCH$_2$CH$_2$C=O); 3.23-3.36 (m, 2H; NHC=OCH$_2$CH$_2$C=O); 3.43-3.50 (m, 4H; CHCH$_2$CH$_2$CH$_2$NH(HN=)CNH$_2$×2); 3.67-3.79 (m, 4H; N(CH$_2$CH$_2$NHC=O)$_2$); 3.83-3.97 (4H; N(CH$_2$CH$_2$NHC=O)$_2$); 4.09-4.38 (m, 2H; CHCH$_2$CH$_2$CH$_2$NH(HN=)CNH$_2$×2); 6.92-8.36 (m, 10H; NH$_2$C=O); 8.03 (m, 4H; NHCOCH$_2$CH$_2$C=O, N(CH$_2$CH$_2$NHC=O)$_2$, NHCO); 8.56 (m, 4H; CHCH$_2$CH$_2$CH$_2$NH(HN=)CNH$_2$×2).

MS (ES$^+$): m/z (%): 608.7 (100) [M+2H]$^{2+}$. HRMS calcd for C$_{68}$H$_{134}$N$_{12}$O$_6$ 608.03083 ([M+2H]$^{2+}$), mass found m/z: 608.03084.

29a (A2-Sp2-P).

IR ν: 3293, 3195 (N—H), 2919 (C—H), 1634 (C=O); δ: 1548 (N—H) cm$^{-1}$. $^1$H NMR (360 MHz, DMSO) 0.88 (t, J=7, 6H; O=CCH$_2$CH$_2$(CH$_2$)$_{12}$CH$_3$×2); 1.14-1.33 (m, 48H;

O=CCCH₂CH₂(CH₂)₁₂CH₃×2); 1.37-1.57 (m, 8H; O=CCCH₂CH₂(CH₂)₁₂CH₃, CHCH₂CH₂CH₂NH(HN=)CNH₂×2); 1.63-1.87 (m, 4H; CHCH₂CH₂CH₂NH(HN=)CNH₂×2); 3.00-3.16 (m, 8H; O=CCH₂CH₂(CH₂)₁₂CH₃×2, CHCH₂CH₂CH₂NH(HN=)CNH₂×2); 3.45-3.57 (m, 8H; N(CH₂CH₂NHC=O)₂, N(CH₂CH₂NHC=O)₂); 4.11-4.22 (m, 2H; CHCH₂CH₂CH₂NH(HN=)CNH₂×2); 6.52-8.46 (m, 12H; HNCOHC=CHCO, HNCOHC=CHCO, NH₂CO, N(CH₂CH₂NHC=O)₂, HNCOHC=CHCO, NHCO, CHCH₂CH₂CH₂NH(HN=)CNH₂×2).

MS (ES⁺): m/z (%): 495.5 (100) [M+2H]²⁺. HRMS calcd for C52H100N12O6 989.79616 ([M+H]⁺), mass found m/z: 989.7950.

29b (A2-Sp2-S).

IR ν: 3338, 3197 (N—H), 2917 (C—H), 1633 (C=O); δ: 1546 (N—H) cm⁻¹. ¹H NMR (360 MHz, DMSO) δ: 0.88 (t, J=7, 6H; O=CCH₂CH₂(CH₂)₁₄CH₃×2); 1.11-1.33 (m, 56H; O=CCCH₂CH₂(CH₂)₁₄CH₃×2); 1.36-1.60 (m, 8H; O=CCCH₂CH₂(CH₂)₁₄CH₃, CHCH₂CH₂CH₂NH(HN=)CNH₂×2); 1.66-1.85 (m, 4H; CHCH₂CH₂CH₂NH(HN=)CNH₂×2); 2.25-2.39 (m, 4H; O=CCH₂CH₂(CH₂)₁₄CH₃×2); 2.55-2.77 (m, 4H; CHCH₂CH₂CH₂NH(HN=)CNH₂×2); 2.96-3.34 (m, 4H; N(CH₂CH₂NHC=O)₂); 3.41-3.64 (m, 4H; N(CH₂CH₂NHC=O)₂); 4.11-4.24 (m, 2H; CHCH₂CH₂CH₂NH(HN=)CNH₂×2); 6.58-8.50 (m, 1H; HNCOHC=CHCO); 7.08 (m, 12H; HNCOHC=CHCO, NH₂CO, N(CH₂CH₂NHC=O)₂, HNCOHC=CHCO, NHCO, CHCH₂CH₂CH₂NH(HN=)CNH₂×2).

MS (ES⁺): m/z (%): 523.5 (100) [M+2H]²⁺. HRMS calcd for C56H108N12O6 1045.85876 ([M+H]⁺), mass found m/z: 1045.8577.

29c (A2-Sp2-O).

IR ν: 3340, 3202 (N—H), 2925 (C—H), 1633 (C=O); δ: 1555 (N—H) cm⁻¹. ¹H NMR (360 MHz, CDCl₃) δ: 0.65-0.83 (m, 6H; (CH₂)₆CH₃×2); 0.85-1.65 (m, 48H; (CH₂)₆CH₃×2, O=CCH₂CH₂(CH₂)₄×2, O=CCH₂CH₂(CH₂)₄×2, CHCH₂CH₂CH₂NH(HN=)CNH₂×2); 1.73-2.17 (m, 16H; CHCH₂CH₂CH₂NH(HN=)CNH₂×2, H₂CHC=CHCH₂×2, O=CCH₂CH₂(CH₂)₄×2); 2.90-3.01 (m, 4H; CHCH₂CH₂CH₂NH(HN=)CNH₂×2); 3.45-3.84 (m, 8H; N(CH₂CH₂NHC=O)₂, N(CH₂CH₂NHC=O)₂); 3.99-4.44 (m, 2H; CHCH₂CH₂CH₂NH(HN=)CNH₂×2); 4.83-5.34 (m, 4H; H₂CHC=CHCH₂×2); 6.05-8.12 (m, 8H; HNCOHC=CHCO, HNCOHC=CHCO, NH₂C=O, NHCOCH₂CH₂C=O, N(CH₂CH₂NHC=O)₂, NHCO); 8.65-9.39 (br s, 4H; CHCH₂CH₂CH₂NH(HN=)CNH₂×2).

MS (ES⁺): m/z (%): 1041.7 (100) [M+H]⁺. HRMS calcd for C56H104N12O6 1041.82746 ([M+H]⁺), mass found m/z: 1041.8262

29d (A2-Sp2-A).

IR ν: 3343, 3202 (N—H), 2917 (C—H), 1632 (C=O); δ: 1546 (N—H) cm⁻¹. ¹H NMR (360 MHz, DMSO) δ: 0.88 (t, J=7, 6H; O=CCCH₂CH₂(CH₂)₁₆CH₃×2); 1.13-1.38 (m, 64H; O=CCCH₂CH₂(CH₂)₁₆CH₃×2); 1.40-1.60 (m, 12H; O=CCCH₂CH₂(CH₂)₁₆CH₃, CHCH₂CH₂CH₂NH(HN=)CNH₂×2, CHCH₂CH₂CH₂NH(HN=)CNH₂×2); 2.0-2.13 (m, 4H; O=CCH₂CH₂(CH₂)₁₆CH₃×2); 3.02-3.18 (m, 4H; CHCH₂CH₂CH₂NH(HN=)CNH₂×2); 4.51-5.15 (m, 10H; N(CH₂CH₂NHC=O)₂, N(CH₂CH₂NHC=O)₂, CHCH₂CH₂CH₂NH(HN=)CNH₂×2); 6.65-8.43 (m, 12H; HNCOHC=CHCO, HNCOHC=CHCO, NH₂CO, N(CH₂CH₂NHC=O)₂, HNCOHC=CHCO, NHCO, CHCH₂CH₂CH₂NH(HN=)CNH₂×2).

MS (ES⁺): m/z (%): 551.5 (100) [M+2H]²⁺. HRMS calcd for C60H116N12O6 1101.92136 ([M+H]⁺), mass found m/z: 1101.9230

29e (A2-Sp2-L).

IR ν: 3352, 3209 (N—H), 2918 (C—H), 1636 (C=O); δ: 1550 (N—H) cm⁻¹. ¹H NMR (360 MHz, DMSO) δ: 0.83-0.94 (m, 6H; O=CCCH₂CH₂(CH₂)₂₀CH₃×2); 1.16-1.36 (m, 80H; O=CCCH₂CH₂(CH₂)₂₀CH₃×2); 1.37-1.79 (m, 12H; O=CCCH₂CH₂(CH₂)₂₀CH₃, CHCH₂CH₂CH₂NH(HN=)CNH₂×2, CHCH₂CH₂CH₂NH(HN=)CNH₂×2); 1.95-2.18 (m, 4H; O=CCCH₂CH₂(CH₂)₂₀CH₃×2); 3.00-3.17 (m, 4H; CHCH₂CH₂CH₂NH(HN=)CNH₂×2); 4.10-4.25 (m, 4H; N(CH₂CH₂NHC=O)₂); 5.07-6.18 (m, 6H; N(CH₂CH₂NHC=O)₂); 4.53 (m, 2H; CHCH₂CH₂CH₂NH(HN=)CNH₂×2); 6.75-8.64 (m, 12H; HNCOHC=CHCO, HNCOHC=CHCO, 2H; NH₂CO, N(CH₂CH₂NHC=O)₂, HNCOHC=CHCO, NHCO, CHCH₂CH₂CH₂NH(HN=)CNH₂×2).

MS (ES⁺): m/z (%): 607.7 (100) [M+2H]²⁺. HRMS calcd for C68H132N12O6 607.02300 ([M+2H]²⁺), mass found m/z: 607.02426

28f (A2-Sp3-P).

IR ν: 3310, 3198 (N—H), 2918 (C—H), 1630 (C=O); δ: 1550 (N—H) cm⁻¹. ¹H NMR (360 MHz, CDCl₃) δ: 0.91-1.25 (m, 6H; O=CCCH₂CH₂(CH₂)₁₂CH₃×2); 1.27-1.41 (m, 48H; O=CCCH₂CH₂(CH₂)₁₂CH₃×2); 1.42-1.65 (m, 8H; O=CCCH₂CH₂(CH₂)₁₂CH₃×2, CHCH₂CH₂CH₂NH(HN=)CNH₂×2); 2.92-3.40 (m, 12H; CHCH₂CH₂CH₂NH(HN=)CNH₂×2, CHCH₂CH₂CH₂NH(HN=)CNH₂, O=CCH₂CH₂(CH₂)₁₂CH₃×2); 5.16-5.67 (m, 8H; NHC=OCH₂CH₂C=O, NHC=OCH₂CH₂C=O, CHCH₂CH₂CH₂NH(HN=)CNH₂×2); 6.27-6.48 (m, 10H; CH₂CH₂CH₂NHC=O)₂, CH₂CH₂CH₂NHC=O)₂, CHCH₂CH₂CH₂NH(HN=)CNH₂×2); 7.09-7.27 (m, 2H; NH₂C=O); 7.9-8.03 (m, 8H; NHCOCH₂CH₂C=O, N(CH₂CH₂CH₂NHC=O)₂, NHCO, CHCH₂CH₂CH₂NH(HN=)CNH₂×2).

MS (ES⁺): m/z (%): 510.4 (100) [M+2H]²⁺. HRMS calcd for C54H106N12O6 510.43710 ([M+2H]²⁺), mass found m/z: 510.43625

28g (A2-Sp3-S).

IR ν: 3309, 3201 (N—H), 2916 (C—H), 1637 (C=O); δ: 1548 (N—H) cm⁻¹. ¹H NMR (360 MHz, DMSO) δ: 0.81-0.90 (m, 6H; O=CCCH₂CH₂(CH₂)₁₄CH₃×2); 1.13-1.34 (m, 56H; O=CCH₂CH₂(CH₂)₁₄CH₃×2); 1.40-1.80 (m, 12H; O=CCH₂CH₂(CH₂)₁₄CH₃×2, CHCH₂CH₂CH₂NH(HN=)CNH₂×2, CHCH₂CH₂CH₂NH(HN=)CNH₂×2); 1.98-2.11 (m, 4H; CHCH₂CH₂CH₂NH(HN=)CNH₂); 4.11-4.22 (m, 4H; O=CCH₂CH₂(CH₂)₁₄CH₃×2); 4.33-5.19 (m, 18H; NHC=OCH₂CH₂C=O, NHC=OCH₂CH₂C=O, CHCH₂CH₂CH₂NH(HN=)CNH₂×2, CH₂CH₂CH₂NHC=O)₂, CH₂CH₂CH₂NHC=O)₂, CHCH₂CH₂CH₂NH(HN=)CNH₂×2); 6.51-8.36 (m, 10H; NH₂C=O, NHCOCH₂CH₂C=O, N(CH₂CH₂CH₂NHC=O)₂, NHCOCHCH₂CH₂CH₂NH(HN=)CNH₂×2).

MS (ES⁺): m/z (%): 538.5 (100) [M+2H]²⁺. HRMS calcd for C58H114N12O6 1075.90571 ([M+H]⁺), mass found m/z: 1075.9034

28h (A2-Sp3-O).

IR ν: 3338, 3195 (N—H), 2925 (C—H), 1625 (C=O); δ: 1558 (N—H) cm⁻¹. ¹H NMR (360 MHz, CDCl₃) δ 0.76-1.00 (m, 6H; (CH₂)₆CH₃×2); 1.03-1.85 (m, 56H; (CH₂)₆CH₃×2, O=CCH₂CH₂(CH₂)₄×2, O=CCH₂CH₂(CH₂)₄×2, CHCH₂CH₂CH₂NH(HN=)CNH₂×2, CHCH₂CH₂CH₂NH(HN=)CNH₂×2, N(CH₂CH₂NHC=O)₂); 1.94-2.54 (m, 16H; H₂CHC=CHCH₂×2, O=CCH₂CH₂(CH₂)₄×2,

NHC=OCH₂CH₂C=O, NHC=OCH₂CH₂C=O); 3.00-3.62 (m, 4H; CHCH₂CH₂CH₂NH(HN=)CNH₂×2); 3.64-4.02 (m, 4H; CH₂CH₂CH₂NHC=O)₂); 4.03-4.54 (m, 4H; CH₂CH₂CH₂NHC=O)₂); 4.97-5.15 (m, 2H; CHCH₂CH₂CH₂NH(HN=)CNH₂×2); 5.28-5.48 (m, 4H; H₂CHC=CHCH₂×2); 6.35-9.29 (m, 10H; NH₂C=O, NHCOCH₂CH₂C=O, N(CH₂CH₂NHC=O)₂, NHCO, CHCH₂CH₂CH₂NH(HN=)CNH₂×2).

MS (ES⁺): m/z (%): 1071.6 (100) [M+H]⁺. HRMS calcd for C58H110N12O6 1071.87441 ([M+H]⁺), mass found m/z: 1071.8743

28i (A2-Sp3-A).

IR ν: 3311, 3209 (N—H), 2916 (C—H), 1637 (C=O); δ: 1549 (N—H) cm⁻¹. ¹H NMR (500 MHz, DMSO) δ: 0.94-1.02 (m, 6H; O=CCH₂CH₂(CH₂)₁₆CH₃×2); 1.10-1.31 (m, 64H; O=CCCH₂CH₂(CH₂)₁₆CH₃×2); 1.41-1.59 (m, 8H; O=CCCH₂CH₂(CH₂)₁₆CH₃×2, CHCH₂CH₂CH₂NH(HN=)CNH₂×2); 1.57-1.86 (m, 8H; CHCH₂CH₂CH₂NH(HN=)CNH₂×2, CHCH₂CH₂CH₂NH(HN=)CNH₂); 1.98-2.14 (m, 6H; CHCH₂CH₂CH₂NH(HN=)CNH₂×2); O=CCCH₂CH₂(CH₂)₁₆CH₃×2); 2.94-3.28 (m, 2H; NHC=OCH₂CH₂C=O);); 4.41-5.64 (m, 16H; NHC=OCH₂CH₂C=O, CHCH₂CH₂CH₂NH(HN=)CNH₂×2, CH₂CH₂CH₂NHC=O)₂, CH₂CH₂CH₂NHC=O)₂, CHCH₂CH₂CH₂NH(HN=)CNH₂×2); 6.51-8.35 (m, 10H; NH₂C=O, NHCOCH₂CH₂C=O, N(CH₂CH₂CH₂NHC=O)₂, NHCO, CHCH₂CH₂CH₂NH(HN=)CNH₂×2).

MS (ES⁺): m/z (%): 566.8 (100) [M+2H]²⁺. HRMS calcd for C62H122N12O6 1131.9662 ([M+H]⁺), mass found m/z: 1131.9683

28j (A2-Sp3-L).

IR ν: 3308, 3218 (N—H), 2916 (C—H), 1638 (C=O); δ: 1553 (N—H) cm⁻¹. ¹H NMR (500 MHz, DMSO) δ 0.77-1.35 (m, 6H; O=CCH₂CH₂(CH₂)₁₂CH₃×2, 86H; O=CCCH₂CH₂(CH₂)₂₀CH₃×2); 1.40-1.57 (m, 8H; O=CCCH₂CH₂(CH₂)₂₀CH₃×2, CHCH₂CH₂CH₂NH(HN=)CNH₂×2); 1.61-1.85 (m, 8H; CHCH₂CH₂CH₂NH(HN=)CNH₂×2, CHCH₂CH₂CH₂NH(HN=)CNH₂); 2.05-2.14 (m, 6H; O=CCH₂CH₂(CH₂)₂₀CH₃×2, NHC=OCH₂CH₂C=O); 3.01-3.16 (m, 6H; NHC=OCH₂CH₂C=O, CHCH₂CH₂CH₂NH(HN=)CNH₂×2); 4.10-4.18 (m, 8H; CH₂CH₂CH₂NHC=O)₂, CH₂CH₂CH₂NHC=O)₂); 5.76-8.44 (m, 12H; CHCH₂CH₂CH₂NH(HN=)CNH₂×2, NH₂C=O, NHCOCH₂CH₂C=O, N(CH₂CH₂CH₂NHC=O)₂, NHCO, CHCH₂CH₂CH₂NH(HN=)CNH₂×2).

MS (ES⁺): m/z (%): 415.2 (100) [M+3H]³⁺. HRMS calcd for C70H138N12O6 414.69747 ([M+3H]³⁺), mass found m/z: 414.69746

29f (A2-Sp4-P).

IR ν: 3349, 3203 (N—H), 2922 (C—H), 1657 (C=O); δ: 1550 (N—H) cm⁻¹. ¹H NMR (360 MHz, CDCl₃) δ: 0.79-0.98 (m, 6H; O=CCH₂CH₂(CH₂)₁₂CH₃×2); 1.03-1.56 (m, 56H; O=CCH₂CH₂(CH₂)₁₂CH₃×2, O=CCH₂CH₂(CH₂)₁₂CH₃, CHCH₂CH₂CH₂NH(HN=)CNH₂×2); 1.57-1.68 (m, 8H; CHCH₂CH₂CH₂NH(HN=)CNH₂×2, N(CH₂CH₂CH₂NHC=O)₂); 2.26-2.36 (m, 4H; O=CCCH₂CH₂(CH₂)₁₂CH₃×2); 2.87-3.02 (m, 8H; CHCH₂CH₂CH₂NH(HN=)CNH₂×2, N(CH₂CH₂CH₂NHC=O)₂); 3.10-3.57 (m, 4H; N(CH₂CH₂CH₂NHC=O)₂); 4.28-4.48 (m, 2H; CHCH₂CH₂CH₂NH(HN=)CNH₂×2); 5.71-8.40 (m, 12H; HNCOHC=CHCO, HNCOHC=CHCO, NH₂CO, HNCOHC=CHCO, N(CH₂CH₂NHC=O)₂, NHCO, CHCH₂CH₂CH₂NH(HN=)CNH₂×2).

MS (ES⁺): m/z (%): 1017.7 (100) [M+H]⁺.

29g (A2-Sp4-S).

IR ν: 3343, 3206 (N—H), 2919 (C—H), 1655 (C=O); δ: 1551 (N—H) cm⁻¹. ¹H NMR (360 MHz, CDCl₃) δ: 0.82-0.98 (m, 6H; O=CCH₂CH₂(CH₂)₁₄CH₃×2); 1.05-1.38 (m, 56H; O=CCCH₂CH₂(CH₂)₁₄CH₃×2); 1.46-1.55 (m, 8H; O=CCCH₂CH₂(CH₂)₁₄CH₃, CHCH₂CH₂CH₂NH(HN=)CNH₂×2); 1.58-1.66 (m, 8H; CHCH₂CH₂CH₂NH(HN=)CNH₂×2); N(CH₂CH₂CH₂NHC=O)₂); 2.04-2.46 (m, 2H; CHCH₂CH₂CH₂NH(HN=)CNH₂×2); 2.90-3.15 (m, 4H; O=CCH₂CH₂(CH₂)₁₄CH₃×2); 3.16-3.42 (m, 8H; CHCH₂CH₂CH₂NH(HN=)CNH₂×2, N(CH₂CH₂CH₂NHC=O)₂); 3.80-3.88 (m, 4H; N(CH₂CH₂CH₂NHC=O)₂); 4.26-4.46 (m, 2H; CHCH₂CH₂CH₂NH(HN=)CNH₂×2); 6.27-9.95 (m, 12H; HNCOHC=CHCO, HNCOHC=CHCO, NH₂CO, HNCOHC=CHCO, N(CH₂CH₂NHC=O)₂, NHCO, CHCH₂CH₂CH₂NH(HN=)CNH₂×2).

MS (ES⁺): m/z (%): 536.4 (100) [M+2H]²⁺. HRMS calcd for C58H112N12O6 536.94475 ([M+2H]²⁺), mass found m/z: 536.94692

29h (A2-Sp4-O).

IR ν: 3292, 3196 (N—H), 2916 (C—H), 1626 (C=O); δ: 1551 (N—H) cm⁻¹. ¹H NMR (360 MHz, CDCl₃) δ: 0.60-0.86 (m, 6H; O=CCH₂CH₂(CH₂)₁₂CH₃×2); 0.89-1.72 (m, 48H; (CH₂)₆CH₃×2, O=CCH₂CH₂(CH₂)₄×2, O=CCH₂CH₂(CH₂)₁₂CH₃, CHCH₂CH₂CH₂NH(HN=)CNH₂×2); 1.76-2.30 (m, 22H; CHCH₂CH₂CH₂NH(HN=)CNH₂×2, N(CH₂CH₂CH₂NHC=O)₂, CHCH₂CH₂CH₂NH(HN=)CNH₂×2, H₂CHC=CHCH₂×2, O=CCH₂CH₂(CH₂)₄×2); 2.90-3.37 (m, 8H; CHCH₂CH₂CH₂NH(HN=)CNH₂×2, N(CH₂CH₂CH₂NHC=O)₂); 4.06-4.37 (4H; N(CH₂CH₂CH₂NHC=O)₂); 4.81-5.05 (m, 2H; CHCH₂CH₂CH₂NH(HN=)CNH₂×2); 5.14-5.39 (m, 4H; H₂CHC=CHCH₂×2); 5.74-8.79 (m, 11H; HNCOHC=CHCO, NH₂CO, HNCOHC=CHCO, N(CH₂CH₂NHC=O)₂, NHCO×2, CHCH₂CH₂CH₂NH(HN=)CNH₂×2).

MS (ES⁺): m/z (%): 1069.7 (100) [M+H]⁺.

29i (A2-Sp4-A).

IR ν: 3294, 3205 (N—H), 2918 (C—H), 1628 (C=O); δ: 1548 (N—H) cm⁻¹. ¹H NMR (500 MHz, DMSO) δ: 0.78-0.91 (m, 6H; O=CCH₂CH₂(CH₂)₁₆CH₃×2); 1.02-1.38 (m, 64H; O=CCCH₂CH₂(CH₂)₁₆CH₃×2); 1.39-1.79 (m, 12H; O=CCCH₂CH₂(CH₂)₁₆CH₃, CHCH₂CH₂CH₂NH(HN=)CNH₂×2, CHCH₂CH₂CH₂NH(HN=)CNH₂×2, N(CH₂CH₂CH₂NHC=O)₂); 1.97-2.11 (m, 4H; O=CCCH₂CH₂(CH₂)₁₆CH₃×2); 2.85-3.29 (m, 12H; CHCH₂CH₂CH₂NH(HN=)CNH₂×2, N(CH₂CH₂CH₂NHC=O)₂, N(CH₂CH₂CH₂NHC=O)₂); 4.11-4.23 (m, 2H; CHCH₂CH₂CH₂NH(HN=)CNH₂×2); 5.12-6.40 (m, 4H; HNCOHC=CHCO, HNCOHC=CHCO, NH₂CO); 6.62-8.48 (m, 8H; HNCOHC=CHCO, N(CH₂CH₂NHC=O)₂, NHCO, CHCH₂CH₂CH₂NH(HN=)CNH₂×2).

MS (ES⁺): m/z (%): 1129.8 (100) [M+H]⁺. HRMS calcd for C62H120N12O6 564.97605 ([M+2H]²⁺), mass found m/z: 564.97606

29j (A2-Sp4-L).

IR ν: 3347, 3201 (N—H), 2915 (C—H), 1653 (C=O); δ: 1547 (N—H) cm⁻¹. ¹H NMR (500 MHz, DMSO) δ. 0.79-1.58 (m, 94H; O=CCCH₂CH₂(CH₂)₂₀CH₃×2, O=CCCH₂CH₂(CH₂)₂₀CH₃×2, O=CCH₂CH₂(CH₂)₂₀CH₃, CHCH₂CH₂CH₂NH(HN=)CNH₂×2); 1.63-1.77 (m, 4H; CHCH₂CH₂CH₂NH(HN=)CNH₂×2); 3.02-3.14 (m, 4H;

N(CH₂CH₂CH₂NHC=O)₂); 4.12-4.24 (m, 4H; O=CCH₂CH₂(CH₂)₂₀CH₃×2); 4.54-5.91 (m, 14H; CHCH₂CH₂CH₂NH(HN=)CNH₂×2, N(CH₂CH₂CH₂NHC=O)₂, N(CH₂CH₂CH₂NHC=O)₂, CHCH₂CH₂CH₂NH(HN=)CNH₂×2); 6.53-8.34 (m, 12H; HNCOHC=CHCO, HNCOHC=CHCO, NH₂CO, HNCOHC=CHCO, N(CH₂CH₂NHC=O)₂, NHCO, CHCH₂CH₂CH₂NH(HN=)CNH₂×2).

MS (ES⁺): m/z (%): 1241.2 (100) [M+H]⁺. HRMS calcd for C70H136N12O6 414.02559 ([M+3H]³⁺), mass found m/z: 414.02353

30a (A3-Sp1-P).

IR ν: 3345, 3194 (N—H), 2920 (C—H), 1633 (C=O); δ: 1545 (N—H) cm⁻¹. ¹H NMR (360 MHz, DMSO) δ: 0.85-0.98 (m, 6H; O=CCH₂CH₂(CH₂)₁₂CH₃×2); 1.18-1.36 (m, 48H; O=CCH₂CH₂(CH₂)₁₂CH₃×2); 1.43-1.65 (m, 8H; O=CCH₂CH₂(CH₂)₁₂CH₃×2, CHCH₂CH₂CH₂NH(HN=)CNH₂×3); 1.71-1.85 (m, 6H; CHCH₂CH₂CH₂NH(HN=)CNH₂×3); 2.03-2.16 (m, 6H; O=CCH₂CH₂(CH₂)₁₂CH₃×2, NHC=OCH₂CH₂C=O); 3.00-3.43 (m, 12H; NHC=OCH₂CH₂C=O, CHCH₂CH₂CH₂NH(HN=)CNH₂×3, N(CH₂CH₂NHC=O)₂); 4.11-4.39 (m, 7H; N(CH₂CH₂NHC=O)₂); CHCH₂CH₂CH₂NH(HN=)CNH₂×3); 6.54-8.35 (m, 13H; NH₂C=O, NHCOCH₂CH₂C=O, N(CH₂CH₂NHC=O)₂, NHCO×2, CHCH₂CH₂CH₂NH(HN=)CNH₂×3).

MS (ES⁺): m/z (%): 574.5 (100) [M+2H]²⁺. HRMS calcd for C58H114N16O7 1147.91292 ([M+H]⁺), mass found m/z: 1147.9105

30b (A3-Sp1-S).

IR ν: 3285, 3196 (N—H), 2916 (C—H), 1627 (C=O); δ: 1540 (N—H) cm⁻¹. ¹H NMR (360 MHz, DMSO) δ: 0.81-0.92 (m, 6H; O=CCH₂CH₂(CH₂)₁₄CH₃×2); 1.16-1.33 (m, 56H; O=CCCH₂CH₂(CH₂)₁₄CH₃×2); 1.38-1.64 (m, 10H; O=CCCH₂CH₂(CH₂)₁₄CH₃×2, CHCH₂CH₂CH₂NH(HN=)CNH₂×3); 1.68-1.80 (m, 6H; CHCH₂CH₂CH₂NH(HN=)CNH₂×3); 1.97-2.15 (m, 4H; O=CCCH₂CH₂(CH₂)₁₄CH₃×2); 3.02-3.42 (m, 14H; NHC=OCH₂CH₂C=O, NHC=OCH₂CH₂C=O, CHCH₂CH₂CH₂NH(HN=)CNH₂×3, N(CH₂CH₂NHC=O)₂); 4.09-4.29 (7H; N(CH₂CH₂NHC=O)₂, CHCH₂CH₂CH₂NH(HN=)CNH₂×3); 6.64-8.18 (m, 13H; NH₂C=O, NHCOCH₂CH₂C=O, N(CH₂CH₂NHC=O)₂, NHCO×2, CHCH₂CH₂CH₂NH(HN=)CNH₂×3).

MS (ES⁺): m/z (%): 402.0 (100) [M+3H]³⁺. HRMS calcd for C62H122N16O7 1203.97552 ([M+2H]²⁺), mass found m/z: 1203.9718

30c (A3-Sp1-O).

IR ν: 3290, 3194 (N—H), 2925 (C—H), 1625 (C=O); δ: 1543 (N—H) cm⁻¹. ¹H NMR (360 MHz, DMSO) δ: 0.77-0.91 (m, 6H; (CH₂)₆CH₃×2); 1.07-1.81 (m, 54H; (CH₂)₆CH₃×2, O=CCH₂CH₂(CH₂)₄×2, O=CCH₂CH₂(CH₂)₄×2, CHCH₂CH₂CH₂NH(HN=)CNH₂×3, CHCH₂CH₂CH₂NH(HN=)CNH₂×3); 1.90-2.16 (m, 12H; H₂CHC=CHCH₂×2, O=CCH₂CH₂(CH₂)₄×2); 2.95-3.44 (m, 10H; NHC=OCH₂CH₂C=O, NHC=OCH₂CH₂C=O, CHCH₂CH₂CH₂NH(HN=)CNH₂×3); 4.05-4.33 (m, 8H; N(CH₂CH₂NHC=O)₂, N(CH₂CH₂NHC=O)₂); 4.98-5.11 (m, 3H; CHCH₂CH₂CH₂NH(HN=)CNH₂×3); 5.27-5.43 (m, 4H; H₂CHC=CHCH₂×2); 6.54-8.30 (m, 7H; NH₂C=O, NHCOCH₂CH₂C=O, N(CH₂CH₂NHC=O)₂, NHCO×2).

MS (ES⁺): m/z (%): 1199.7 (100)[M+H]⁺.

30d (A3-Sp1-A).

IR ν: 3284, 3193 (N—H), 2916 (C—H), 1628 (C=O); δ: 1541 (N—H) cm⁻¹. ¹H NMR (360 MHz, DMSO) δ: 0.88 (t, J=7, 6H; O=CCH₂CH₂(CH₂)₁₆CH₃×2); 1.15-1.32 (m, 64H; O=CCCH₂CH₂(CH₂)₁₆CH₃×2); 1.39-1.60 (m, 10H; O=CCCH₂CH₂(CH₂)₁₆CH₃×2, CHCH₂CH₂CH₂NH(HN=)CNH₂×3); 1.66-1.80 (m, 6H; CHCH₂CH₂CH₂NH(HN=)CNH₂×3); 3.02-3.37 (m, 14H; O=CCCH₂CH₂(CH₂)₁₆CH₃×2, NHC=OCH₂CH₂C=O, NHC=OCH₂CH₂C=O, CHCH₂CH₂CH₂NH(HN=)CNH₂×3); 4.13-4.28 (m, 8H; N(CH₂CH₂NHC=O)₂, N(CH₂CH₂NHC=O)₂); 6.52-8.26 (m, 3H; CHCH₂CH₂CH₂NH(HN=)CNH₂×3, NH₂C=O, NHCOCH₂CH₂C=O, N(CH₂CH₂NHC=O)₂, NHCO×2, CHCH₂CH₂CH₂NH(HN=)CNH₂×3).

MS (ES⁺): m/z (%): 420.8 (100) [M+3H]³⁺. HRMS calcd for C66H130N16O7 420.01234 ([M+3H]³⁺), mass found m/z: 420.01235

30e (A3-Sp1-L).

IR ν: 3354, 3206 (N—H), 2918 (C—H), 1654 (C=O); δ: 1545 (N—H) cm⁻¹. ¹H NMR (500 MHz, DMSO) δ 0.86 (t, J=7, 6H; O=CCCH₂CH₂(CH₂)₂₀CH₃×2); 0.91-1.30 (m, 80H; O=CCCH₂CH₂(CH₂)₂₀CH₃×2); 1.34-1.56 (m, 10H; O=CCCH₂CH₂(CH₂)₂₀CH₃×2, CHCH₂CH₂CH₂NH(HN=)CNH₂×3); 1.62-1.72 (m, 6H; CHCH₂CH₂CH₂NH(HN=)CNH₂×3); 1.72-2.60 (m, 8H; O=CCCH₂CH₂(CH₂)₂₀CH₃×2, NHC=OCH₂CH₂C=O, NHC=OCH₂CH₂C=O); 2.61-2.68 (m, 6H; CHCH₂CH₂CH₂NH(HN=)CNH₂×3); 3.42-3.49 (m, 4H; N(CH₂CH₂NHC=O)₂); 3.67-3.75 (4H; N(CH₂CH₂NHC=O)₂); 4.11-4.33 (m, 3H; CHCH₂CH₂CH₂NH(HN=)CNH₂×3); 6.60-8.35 (m, 13H; NH₂C=O, NHCOCH₂CH₂C=O, N(CH₂CH₂NHC=O)₂, NHCO×2, CHCH₂CH₂CH₂NH(HN=)CNH₂×3).

MS (ES⁺): m/z (%): 1372.7 (100) [M+H]⁺.

31a (A3-Sp2-P).

IR ν: 3352, 3203 (N—H), 2921 (C—H), 1634 (C=O); δ: 1547 (N—H) cm⁻¹. ¹H NMR (360 MHz, DMSO) δ: 0.88 (t, J=7, 6H; O=CCH₂CH₂(CH₂)₁₂CH₃×2);); 1.12-1.33 (m, 48H; O=CCH₂CH₂(CH₂)₁₂CH₃×2); 1.40-1.83 (m, 16H; O=CCH₂CH₂(CH₂)₁₂CH₃, CHCH₂CH₂CH₂NH(HN=)CNH₂×3, CHCH₂CH₂CH₂NH(HN=)CNH₂×3); 3.02-3.44 (m, 10H; O=CCCH₂CH₂(CH₂)₁₂CH₃×2, CHCH₂CH₂CH₂NH(HN=)CNH₂×3); 3.93-5.12 (m, 11H; N(CH₂CH₂NHC=O)₂, N(CH₂CH₂NHC=O)₂, CHCH₂CH₂CH₂NH(HN=)CNH₂×3); 6.43-8.66 (m, 15H; HNCOHC=CHCO, HNCOHC=CHCO, NH₂CO, N(CH₂CH₂NHC=O)₂, HNCOHC=CHCO, NHCO×2, CHCH₂CH₂CH₂NH(HN=)CNH₂×3).

MS (ES⁺): m/z (%): 573.5 (100) [M+2H]²⁺. HRMS calcd for C58H112N16O7 1145.89727 ([M+H]⁺), mass found m/z: 1145.8917

31b (A3-Sp2-S).

IR ν: 3283, 3198 (N—H), 2917 (C—H), 1628 (C=O); δ: 1544 (N—H) cm⁻¹. ¹H NMR (360 MHz, DMSO) δ: 0.88 (t, J=7, 6H; O=CCCH₂CH₂(CH₂)₁₄CH₃×2);); 1.12-1.34 (m, 56H; O=CCH₂CH₂(CH₂)₁₄CH₃×2); 1.35-1.84 (m, 16H; O=CCCH₂CH₂(CH₂)₁₄CH₃, CHCH₂CH₂CH₂NH(HN=)CNH₂×3, CHCH₂CH₂CH₂NH(HN=)CNH₂×3); 1.95-2.12 (m, 4H; O=CCCH₂CH₂(CH₂)₁₄CH₃×2); 3.04-3.37 (m, 6H; CHCH₂CH₂CH₂NH(HN=)CNH₂×3); 3.94-5.02 (m, 11H; N(CH₂CH₂NHC=O)₂, N(CH₂CH₂NHC=O)₂, CHCH₂CH₂CH₂NH(HN=)CNH₂×3); 6.61-8.47 (m, 15H; HNCOHC=CHCO, HNCOHC=CHCO, NH₂CO, N(CH₂CH₂NHC=O)₂, HNCOHC=CHCO, NHCO×2, CHCH₂CH₂CH₂NH(HN=)CNH₂×3).

MS (ES⁺): m/z (%): 401.4 (100) [M+3H]³⁺. HRMS calcd for C62H120N16O7 400.65292 ([M+3H]³⁺), mass found m/z: 444.87965

31c (A3-Sp2-O).

IR ν: 3283, 3195 (N—H), 2925 (C—H), 1633 (C=O); δ: 1548 (N—H) cm⁻¹. ¹H NMR (360 MHz, CDCl₃) δ: 0.64-0.83

(m, 6H; (CH$_2$)$_6$CH$_3$×2); 0.90-1.46 (m, 40H; (CH$_2$)$_6$CH$_3$×2, O=CCH$_2$CH$_2$(CH$_2$)$_4$×2); 1.47-1.63 (m, 10H; O=CCCH$_2$CH$_2$(CH$_2$)$_4$×2, CHCH$_2$CH$_2$CH$_2$NH(HN=)CNH$_2$×3); 1.74-2.17 (m, 21H; CHCH$_2$CH$_2$CH$_2$NH(HN=)CNH$_2$×3, CHCH$_2$CH$_2$CH$_2$NH(HN=)CNH$_2$×3, H$_2$CHC=CHCH$_2$×2, O=CCH$_2$CH$_2$(CH$_2$)$_4$×2); 3.54-3.62 (m, 14H; CHCH$_2$CH$_2$CH$_2$NH(HN=)CNH$_2$×3, N(CH$_2$CH$_2$NHC=O)$_2$, N(CH$_2$CH$_2$NHC=O)$_2$); 4.87-5.02 (m, 7H; CHCH$_2$CH$_2$CH$_2$NH(HN=)CNH$_2$×3, H$_2$CHC=CHCH$_2$×2); 6.27-6.54 (m, 1H; HNCOHC=CHCO); 6.99-7.26 (m, 1H; HNCOHC=CHCO); 7.83-8.07 (m, 7H; NH$_2$C=O, NHCOCH$_2$CH$_2$C=O, N(CH$_2$CH$_2$NHC=O)$_2$, NHCO×2).

MS (ES$^+$): m/z (%): 1197.7 (100) [M+H]$^+$.

31d (A3-Sp2-A).

IR ν: 3292, 3197 (N—H), 2916 (C—H), 1632 (C=O); δ: 1545 (N—H) cm$^{-1}$. $^1$H NMR (360 MHz, DMSO) δ: 0.87 (t, J=7, 6H; O=CCH$_2$CH$_2$(CH$_2$)$_{16}$CH$_3$×2);); 1.14-1.35 (m, 64H; O=CCCH$_2$CH$_2$(CH$_2$)$_{16}$CH$_3$×2); 1.37-1.85 (m, 16H; O=CCCH$_2$CH$_2$(CH$_2$)$_{16}$CH$_3$, CHCH$_2$CH$_2$CH$_2$NH(HN=)CNH$_2$×3, CHCH$_2$CH$_2$CH$_2$NH(HN=)CNH$_2$×3); 3.04-3.16 (m, 4H; O=CCH$_2$CH$_2$(CH$_2$)$_{16}$CH$_3$×2); 3.46-5.01 (m, 17H; CHCH$_2$CH$_2$CH$_2$NH(HN=)CNH$_2$×3, N(CH$_2$CH$_2$NHC=O)$_2$, N(CH$_2$CH$_2$NHC=O)$_2$, CHCH$_2$CH$_2$CH$_2$NH(HN=)CNH$_2$×3); 6.56-8.50 (m, 15H; HNCOHC=CHCO, HNCOHC=CHCO, NH$_2$CO, N(CH$_2$CH$_2$NHC=O)$_2$, HNCOHC=CHCO, NHCO×2, CHCH$_2$CH$_2$CH$_2$NH(HN=)CNH$_2$×3).

MS (ES$^+$): m/z (%): 420.1 (100) [M+3H]$^{3+}$. HRMS calcd for C66H128N16O7 1258.0188 ([M+H]$^+$), mass found m/z: 1258.02247

31e (A3-Sp2-L).

IR ν: 3352, 3208 (N—H), 2916 (C—H), 1655 (C=O); δ: 1548 (N—H) cm$^{-1}$. $^1$H NMR (500 MHz, DMSO) δ: 0.86 (t, J=7, 6H; O=CCCH$_2$CH$_2$(CH$_2$)$_{20}$CH$_3$×2); 1.05-1.39; (m, 80H; O=CCCH$_2$CH$_2$(CH$_2$)$_{20}$CH$_3$×2); 1.40-1.79 (m, 14H; O=CCCH$_2$CH$_2$(CH$_2$)$_{20}$CH$_3$, CHCH$_2$CH$_2$CH$_2$NH(HN=)CNH$_2$×3, CHCH$_2$CH$_2$CH$_2$NH(HN=)CNH$_2$×3); 3.00-3.15 (m, 4H; O=CCH$_2$CH$_2$(CH$_2$)$_{20}$CH$_3$×2); 4.11-4.34 (m, 6H; CHCH$_2$CH$_2$CH$_2$NH(HN=)CNH$_2$×3); 4.92-6.32 (m, 12H; N(CH$_2$CH$_2$NHC=O)$_2$, N(CH$_2$CH$_2$NHC=O)$_2$, CHCH$_2$CH$_2$CH$_2$NH(HN=)CNH$_2$×3, HNCOHC=CHCO); 6.63-8.28 (m, 13H; HNCOHC=CHCO, 2H; NH$_2$CO, N(CH$_2$CH$_2$NHC=O)$_2$, HNCOHC=CHCO, NHCO×2, CHCH$_2$CH$_2$CH$_2$NH(HN=)CNH$_2$×3).

MS (ES$^+$): m/z (%): 1370.7 (100) [M+H]$^+$.

30f (A3-Sp3-P).

IR ν: 3293, 3200 (N—H), 2916 (C—H), 1638 (C=O); δ: 1548 (N—H) cm$^{-1}$. $^1$H NMR (360 MHz, DMSO) δ: 0.85 (, 6H; O=CCCH$_2$CH$_2$(CH$_2$)$_{12}$CH$_3$×2); 1.01-1.31 (m, 48H; O=CCCH$_2$CH$_2$(CH$_2$)$_{12}$CH$_3$×2); 1.34-1.78 (m, 10H; O=CCH$_2$CH$_2$(CH$_2$)$_{12}$CH$_3$×2, CHCH$_2$CH$_2$CH$_2$NH(HN=)CNH$_2$×3); 2.88-3.26 (m, 14H; CHCH$_2$CH$_2$CH$_2$NH(HN=)CNH$_2$×3, CHCH$_2$CH$_2$CH$_2$NH(HN=)CNH$_2$, O=CCH$_2$CH$_2$(CH$_2$)$_{12}$CH$_3$×2); 3.97-4.34 (m, 4H; NHC=OCH$_2$CH$_2$C=O), NHC=OCH$_2$CH$_2$C=O); 4.99-5.98 (m, 17H; CHCH$_2$CH$_2$CH$_2$NH(HN=)CNH$_2$×3, CH$_2$CH$_2$CH$_2$NHC=O)$_2$, CH$_2$CH$_2$CH$_2$NHC=O)$_2$, CHCH$_2$CH$_2$CH$_2$NH(HN=)CNH$_2$×3); 6.70-8.33 (m, 13H; NH$_2$C=O, NHCOCH$_2$CH$_2$C=O, N(CH$_2$CH$_2$CH$_2$NHC=O)$_2$, NHCO×2, CHCH$_2$CH$_2$CH$_2$NH(HN=)CNH$_2$×3).

MS (ES$^+$): m/z (%): 1175.7 (100) [M+H]$^+$. HRMS calcd for C60H118N16O7 391.98104 ([M+3H]$^{3+}$), mass found m/z: 391.98085

30g (A3-Sp3-S).

IR ν: 3277, 3198 (N—H), 2921 (C—H), 1634 (C=O); δ: 1555 (N—H) cm$^{-1}$. $^1$H NMR (360 MHz, DMSO) δ: 0.88 (t, J=7, 6H; O=CCH$_2$CH$_2$(CH$_2$)$_{14}$CH$_3$×2); 1.14-1.34 (m, 56H; O=CCH$_2$CH$_2$(CH$_2$)$_{14}$CH$_3$×2); 2.35-2.44 (m, 10H; O=CCH$_2$CH$_2$(CH$_2$)$_{14}$CH$_3$×2, CHCH$_2$CH$_2$CH$_2$NH(HN=)CNH$_2$×3); 2.90-3.33 (m, 10H; CHCH$_2$CH$_2$CH$_2$NH(HN=)CNH$_2$×3, CHCH$_2$CH$_2$CH$_2$NH(HN=)CNH$_2$); 4.08-4.28 (m, 8H; O=CCH$_2$CH$_2$(CH$_2$)$_{14}$CH$_3$×2, NHC=OCH$_2$CH$_2$C=O, NHC=OCH$_2$CH$_2$C=O); 4.72-5.56 (m, 17H; CHCH$_2$CH$_2$CH$_2$NH(HN=)CNH$_2$×3, CH$_2$CH$_2$CH$_2$NHC=O)$_2$, CH$_2$CH$_2$CH$_2$NHC=O)$_2$, CHCH$_2$CH$_2$CH$_2$NH(HN=)CNH$_2$×3); 6.53-8.30 (m, 13H; NH$_2$C=O, NHCOCH$_2$CH$_2$C=O, N(CH$_2$CH$_2$CH$_2$NHC=O)$_2$, NHCO×2, CHCH$_2$CH$_2$CH$_2$NH(HN=)CNH$_2$×3).

MS (ES$^+$): m/z (%): 411.5 (100) [M+3H]$^{3+}$. HRMS calcd for C64H126N16O7 410.66857 ([M+3H]$^{3+}$), mass found m/z: 410.66962

30h (A3-Sp3-O).

IR ν: 3349, 3196 (N—H), 2925 (C—H), 1627 (C=O); δ: 1548 (N—H) cm$^{-1}$. $^1$H NMR (360 MHz, CDCl$_3$) δ: 0.54-1.67 (m, 56H; (CH$_2$)$_6$CH$_3$×2, (CH$_2$)$_6$CH$_3$×2, O=CCH$_2$CH$_2$(CH$_2$)$_4$×2, O=CCH$_2$CH$_2$(CH$_2$)$_4$×2, CHCH$_2$CH$_2$CH$_2$NH(HN=)CNH$_2$×3); 1.77-2.27 (m, 6H; CHCH$_2$CH$_2$CH$_2$NH(HN=)CNH$_2$×3); 1.86 (m, 16H; N(CH$_2$CH$_2$CH$_2$NHC=O)$_2$, H$_2$CHC=CHCH$_2$×2, O=CCH$_2$CH$_2$(CH$_2$)$_4$×2); 3.54-3.77 (m, 10H; NHC=OCH$_2$CH$_2$C=O, NHC=OCH$_2$CH$_2$C=O, CHCH$_2$CH$_2$CH$_2$NH(HN=)CNH$_2$×3); 4.84-5.01 (m, 11H; CH$_2$CH$_2$CH$_2$NHC=O)$_2$, CH$_2$CH$_2$CH$_2$NHC=O)$_2$, CHCH$_2$CH$_2$CH$_2$NH(HN=)CNH$_2$×3); 5.16-5.32 (m, 4H; H$_2$CHC=CHCH$_2$×2); 7.83-10.24 (m, 13H; NH$_2$C=O, NHCOCH$_2$CH$_2$C=O, N(CH$_2$CH$_2$NHC=O)$_2$, NHCO×2, CHCH$_2$CH$_2$CH$_2$NH(HN=)CNH$_2$×3).

MS (ES$^+$): m/z (%): 409.5 (100) [M+3H]$^{3+}$. HRMS calcd for C64H122N16O7 409.32481 ([M+3H]$^{3+}$), mass found m/z: 409.32610

30i (A3-Sp3-A).

IR ν: 3296, 3199 (N—H), 2918 (C—H), 1639 (C=O); δ: 1548 (N—H) cm$^{-1}$. $^1$H NMR (500 MHz, DMSO) δ: 0.77-0.93 (m, 6H; O=CCCH$_2$CH$_2$(CH$_2$)$_{16}$CH$_3$×2); 1.10-1.34 (m, 64H; O=CCCH$_2$CH$_2$(CH$_2$)$_{16}$CH$_3$×2); 1.40-1.79 (m, 16H; O=CCH$_2$CH$_2$(CH$_2$)$_{16}$CH$_3$×2, CHCH$_2$CH$_2$CH$_2$NH(HN=)CNH$_2$×3, CHCH$_2$CH$_2$CH$_2$NH(HN=)CNH$_2$×3); 2.89-3.31 (m, 4H; CHCH$_2$CH$_2$CH$_2$NH(HN=)CNH$_2$); 4.05-4.31 (m, 4H; O=CCCH$_2$CH$_2$(CH$_2$)$_{16}$CH$_3$×2); 4.39-5.65 (m, 21H; NHC=OCH$_2$CH$_2$C=O, NHC=OCH$_2$CH$_2$C=O, CHCH$_2$CH$_2$CH$_2$NH(HN=)CNH$_2$×3, CH$_2$CH$_2$CH$_2$NHC=O)$_2$, CH$_2$CH$_2$CH$_2$NHC=O)$_2$, CHCH$_2$CH$_2$CH$_2$NH(HN=)CNH$_2$×3); 6.60-8.25 (m, 13H; NH$_2$C=O, NHCOCH$_2$CH$_2$C=O, N(CH$_2$CH$_2$CH$_2$NHC=O)$_2$, NHCO×2, CHCH$_2$CH$_2$CH$_2$NH(HN=)CNH$_2$×3).

MS (ES$^+$): m/z (%): 430.0 (100) [M+3H]$^{3+}$. HRMS calcd for C68H134N16O7 429.35611 ([M+3H]$^{3+}$), mass found m/z: 429.35569

30j (A3-Sp3-L).

IR ν: 3305, 3207 (N—H), 2916 (C—H), 1638 (C=O); δ:1550 (N—H) cm$^{-1}$. $^1$H NMR (500 MHz, DMSO) δ: 0.80-0.90 (m, 6H; O=CCCH$_2$CH$_2$(CH$_2$)$_{20}$CH$_3$×2); 1.12-1.33 (m, 80H; O=CCCH$_2$CH$_2$(CH$_2$)$_{20}$CH$_3$×2); 1.39-1.60 (m, 10H; O=CCCH$_2$CH$_2$(CH$_2$)$_{20}$CH$_3$×2, CHCH$_2$CH$_2$CH$_2$NH(HN=)CNH$_2$×3); 1.61-1.80 (m, 6H; CHCH$_2$CH$_2$CH$_2$NH (HN=)CNH$_2$×3); 2.99-3.17 (m, 8H; CHCH$_2$CH$_2$CH$_2$NH(HN=)CNH$_2$, O=CCH$_2$CH$_2$(CH$_2$)$_{20}$CH$_3$×2); 4.03-4.32 (m, 2H; NHC=OCH$_2$CH$_2$C=O); 4.71-6.10 (m, 19H; NHC=OCH$_2$CH$_2$C=O, CHCH$_2$CH$_2$CH$_2$NH(HN=)CNH$_2$×3, CH$_2$CH$_2$CH$_2$NHC=O)$_2$, CH$_2$CH$_2$CH$_2$NHC=O)$_2$, CHCH$_2$CH$_2$CH$_2$NH(HN=)CNH$_2$×3); 6.60-8.28 (m, 13H; NH$_2$C=O, NHCOCH$_2$CH$_2$C=O, N(CH$_2$CH$_2$CH$_2$NHC=O)$_2$, NHCO×2, CHCH$_2$CH$_2$CH$_2$NH(HN=)CNH$_2$×3).

MS (ES$^+$): m/z (%): 700.5 (100) [M+2H]$^{2+}$.

31f (A3-Sp4-P).

IR v: 3338, 3194 (N—H), 2917 (C—H), 1627 (C=O); δ: 1544 (N—H) cm$^{-1}$. $^1$H NMR (360 MHz, DMSO) δ: 0.85 (t, J=7, 6H; O=CCH$_2$CH$_2$(CH$_2$)$_{12}$CH$_3$×2); 1.05-1.34 (m, 48H; O=CCCH$_2$CH$_2$(CH$_2$)$_{12}$CH$_3$×2);); 1.31-1.82 (m, 16H; O=CCCH$_2$CH$_2$(CH$_2$)$_{12}$CH$_3$, CHCH$_2$CH$_2$CH$_2$NH(HN=)CNH$_2$×3, CHCH$_2$CH$_2$CH$_2$NH(HN=)CNH$_2$×3); 2.58-2.71 (m, 8H; N(CH$_2$CH$_2$CH$_2$NHC=O)$_2$, O=CCH$_2$CH$_2$(CH$_2$)$_{12}$CH$_3$×2); 2.89-3.30 (m, 6H; CHCH$_2$CH$_2$CH$_2$NH(HN=)CNH$_2$×3); 4.04-4.29 (m, 4H; N(CH$_2$CH$_2$CH$_2$NHC=O)$_2$); 4.34-5.44 (m, 7H; N(CH$_2$CH$_2$CH$_2$NHC=O)$_2$, CHCH$_2$CH$_2$CH$_2$NH(HN=)CNH$_2$×3); 6.52-8.57 (m, 9H; HNCOHC=CHCO, HNCOHC=CHCO, NH$_2$CO, N(CH$_2$CH$_2$NHC=O)$_2$, NHCO×2); 9.27-9.39 (br s, 6H; CHCH$_2$CH$_2$CH$_2$NH(HN=)CNH$_2$×3).

MS (ES$^+$): m/z (%): 588.7 (100) [M+2H]$^{2+}$.

31g (A3-Sp4-S).

IR v: 3286, 3198 (N—H), 2916 (C—H), 1627 (C=O); δ: 1541 (N—H) cm$^{-1}$. $^1$H NMR (360 MHz, DMSO) δ: 0.85 (t, J=7, 6H; O=CCCH$_2$CH$_2$(CH$_2$)$_{14}$CH$_3$×2); 1.12-1.31 (m, 56H; O=CCCH$_2$CH$_2$(CH$_2$)$_{14}$CH$_3$×2);); 1.35-1.84 (m, 16H; O=CCCH$_2$CH$_2$(CH$_2$)$_{14}$CH$_3$, CHCH$_2$CH$_2$CH$_2$NH(HN=)CNH$_2$×3, CHCH$_2$CH$_2$CH$_2$NH(HN=)CNH$_2$×3); 1.96-2.07 (m, 4H; N(CH$_2$CH$_2$CH$_2$NHC=O)$_2$); 2.91-3.22 (m, 10H; O=CCH$_2$CH$_2$(CH$_2$)$_{14}$CH$_3$×2); 4.34-5.28 (m, 11H; N(CH$_2$CH$_2$CH$_2$NHC=O)$_2$, N(CH$_2$CH$_2$CH$_2$NHC=O)$_2$, CHCH$_2$CH$_2$CH$_2$NH(HN=)CNH$_2$×3); 6.577-8.47 (m, 9H; HNCOHC=CHCO, HNCOHC=CHCO); 7, NH$_2$CO, HNCOHC=CHCO, N(CH$_2$CH$_2$NHC=O)$_2$, NHCO×2); 9.29-9.37 (br s, 6H; CHCH$_2$CH$_2$CH$_2$NH(HN=)CNH$_2$×3).

MS (ES$^+$): m/z (%): 616.6 (100) [M+2H]$^{2+}$. HRMS calcd for C64H124N16O7 409.99669 ([M+3H]$^{3+}$), mass found m/z: 409.99861

31h (A3-Sp4-O).

IR v: 3292, 3194 (N—H), 2925 (C—H), 1626 (C=O); δ: 1548 (N—H) cm$^{-1}$. $^1$H NMR (360 MHz, CDCl$_3$) δ 0.85-0.98 (m, 6H; O=CCCH$_2$CH$_2$(CH$_2$)$_{12}$CH$_3$×2); 1.03-1.74 (m, 56H; (CH$_2$)$_6$CH$_3$×2, O=CCH$_2$CH$_2$(CH$_2$)$_4$×2, O=CCH$_2$CH$_2$(CH$_2$)$_{12}$CH$_3$, CHCH$_2$CH$_2$CH$_2$NH(HN=)CNH$_2$×3, CHCH$_2$CH$_2$CH$_2$NH(HN=)CNH$_2$×3); 1.87-2.07 (m, 4H; N(CH$_2$CH$_2$CH$_2$NHC=O)$_2$); 2.09-2.32 (m, 12H; H$_2$CHC=CHCH$_2$×2, O=CCH$_2$CH$_2$(CH$_2$)$_4$×2); 3.68-3.92 (m, 17H; CHCH$_2$CH$_2$CH$_2$NH(HN=)CNH$_2$×3, N(CH$_2$CH$_2$CH$_2$NHC=O)$_2$, N(CH$_2$CH$_2$CH$_2$NHC=O)$_2$, CHCH$_2$CH$_2$CH$_2$NH(HN=)CNH$_2$×3); 5.32-5.46 (m, 4H; H$_2$CHC=CHCH$_2$×2); 5.93-9.09 (m, 14H; HNCOHC=CHCO, NH$_2$CO, HNCOHC=CHCO, N(CH$_2$CH$_2$NHC=O)$_2$, NHCO×3, CHCH$_2$CH$_2$CH$_2$NH(HN=)CNH$_2$×3).

MS (ES$^+$): m/z (%): 612.5 (100) [M+H]$^+$.

31i (A3-Sp4-A).

IR v: 3339, 3198 (N—H), 2916 (C—H), 1651 (C=O); δ: 1546 (N—H) cm$^{-1}$. $^1$H NMR (360 MHz, DMSO) δ: 0.77-0.92 (m, 6H; O=CCH$_2$CH$_2$(CH$_2$)$_{16}$CH$_3$×2); 1.04-1.34 (m, 64H; O=CCCH$_2$CH$_2$(CH$_2$)$_{16}$CH$_3$×2);); 1.97-2.10 (m, 10H; O=CCCH$_2$CH$_2$(CH$_2$)$_{16}$CH$_3$, CHCH$_2$CH$_2$CH$_2$NH(HN=)CNH$_2$×3); 2.87-3.35 (m, 10H; CHCH$_2$CH$_2$CH$_2$NH(HN=)CNH$_2$×3, N(CH$_2$CH$_2$CH$_2$NHC=O)$_2$); 4.07-4.33 (m, 10H; O=CCH$_2$CH$_2$(CH$_2$)$_{16}$CH$_3$×2, CHCH$_2$CH$_2$CH$_2$NH(HN=)CNH$_2$×3); 4.43-5.57 (m, 11H; N(CH$_2$CH$_2$CH$_2$NHC=O)$_2$, N(CH$_2$CH$_2$CH$_2$NHC=O)$_2$, CHCH$_2$CH$_2$CH$_2$NH(HN=)CNH$_2$×3); 6.58-8.15 (m, 15H; HNCOHC=CHCO, NH$_2$CO, HNCOHC=CHCO, N(CH$_2$CH$_2$NHC=O)$_2$, NHCO×2, CHCH$_2$CH$_2$CH$_2$NH(HN=)CNH$_2$×3).

MS (ES$^+$): m/z (%): 428.7 (100) [M+3H]$^{3+}$. HRMS calcd for C68H132N16O7 428.68422 ([M+3H]$^{3+}$), mass found m/z: 428.68637

31j (A3-Sp4-L).

IR v: 3350, 3198 (N—H), 2916 (C—H), 1634 (C=O); δ: 1546 (N—H) cm$^{-1}$. $^1$H NMR (360 MHz, DMSO) δ: 0.74-0.91 (m, 6H; O=CCH$_2$CH$_2$(CH$_2$)$_{20}$CH$_3$×2); 1.06-1.30 (m, 80H; O=CCH$_2$CH$_2$(CH$_2$)$_{20}$CH$_3$×2);); 1.34-1.77 (m, 10H; O=CCH$_2$CH$_2$(CH$_2$)$_{20}$CH$_3$, CHCH$_2$CH$_2$CH$_2$NH(HN=)CNH$_2$×3); 1.90-2.10 (m, 6H; CHCH$_2$CH$_2$CH$_2$NH(HN=)CNH$_2$×3); 2.97-3.53 (m, 14H; N(CH$_2$CH$_2$CH$_2$NHC=O)$_2$, O=CCCH$_2$CH$_2$(CH$_2$)$_{20}$CH$_3$×2, CHCH$_2$CH$_2$CH$_2$NH(HN=)CNH$_2$×3); 4.46-5.62 (m, 11H; N(CH$_2$CH$_2$CH$_2$NHC=O)$_2$, N(CH$_2$CH$_2$CH$_2$NHC=O)$_2$, CHCH$_2$CH$_2$CH$_2$NH(HN=)CNH$_2$×3); 6.71-8.61 (m, 15H; HNCOHC=CHCO, HNCOHC=CHCO, NH$_2$CO, HNCOHC=CHCO, N(CH$_2$CH$_2$NHC=O)$_2$, NHCO×2, CHCH$_2$CH$_2$CH$_2$NH(HN=)CNH$_2$×3).

MS (ES$^+$): m/z (%): 699.5 (100) [M+2H]$^{2+}$.

4. Evaluation of Transfection Properties 4.1. General Lipoplex Preparation Protocol The corresponding cationic lipid (1 mM in methanol) were mixed in different proportions with DOPE (10 mg/mL in chloroform) and the organic solvent removed by evaporation in an oven (37° C.) overnight. The resultant thin films were then hydrated with PBS. The solutions were vortexed (10-20 s) and incubated at ambient temperature for 20 min. Plasmid DNA or siRNA solution (0.04 mg/mL in PBS or another isotonic solution) was subsequently added and the solution vortexed (10-20 s). The lipoplexes were incubated at room temperature for 20 min before being used.

4.2. Transfection of pEGFP-C1 into Cell Lines

Human HeLa cells were grown in RPMI supplemented with 4 mM glutamine, 10% FCS and 100 units/ml penicillin/streptomycin (RPMI-CM) until 80% confluence. HEK293 and B16F10 cells were grown in DMEM supplemented with 4 mM glutamine, 10% FCS and 100 units/ml penicillin/streptomycin (DMEM-CM) until 80% confluence. Cells were then suspended using trypsin/EDTA and counted. 2×10$^4$ cells in 150 μL of media per well were seeded in 96 well plates and incubated overnight. The day afterwards, the different lipoplex formulations were added. Each experiment was performed in quadruplicate, using Effectene® Transfection Reagent (Qiagen), Lipofectamine™ 2000 (Invitrogen) and Fugene (Roche) as positive controls and untreated cells as negative controls. After two days incubation at 37° C. and 5% CO$_2$ (the change of media after transfection was not necessary), the green fluorescent protein (GFP) expression, as a consequence of transfecting the pEGFP-C1, was evidenced using a fluorescent microscope (Leica) and measured by flow cytometry. For the flow cytometry analysis, cells were washed twice with PBS, detached with trypsin/EDTA, harvested with 2% ferum bovine serum (FBS) in PBS, centrifuged and resuspended with 2% FBS in PBS and analyzed using a BD FACSaria flow cytometer. Transfection efficiency was measured as percentage of transfected cells. As shown in Table 2, derivatives 28a and 29a (N/P ratio 3, 1:1 mol mixture with DOPE) transfected cells more effectively than the positive controls.

Table 2 immediately below shows flow cytometry analysis of HeLa cells 48 h after transfection with a reporter plasmid for all the library members. Reagents that obtained greater than 50% transfection were also analyzed against HEK293 and B16F10 cell lines. Transfection results (+ percentages of transfection between 5-25%; ++ percentages of transfection between 25-50%; N.D. not determined). MTT toxicity assay results are indicated between brackets with 100% being cell viability of untreated cells.

| Compound | HeLa | HEK293 | B16F10 |
|---|---|---|---|
| A1-Sp1-P | + | N.D. | N.D. |
| A1-Sp1-S | + | N.D. | N.D. |
| A1-Sp1-O | + | N.D. | N.D. |
| A1-Sp1-A | + | N.D. | N.D. |
| A1-Sp1-L | + | N.D. | N.D. |
| A1-Sp2-P | ++ | N.D. | N.D. |
| A1-Sp2-S | + | N.D. | N.D. |
| A1-Sp2-O | + | N.D. | N.D. |
| A1-Sp2-A | + | N.D. | N.D. |
| A1-Sp2-L | + | N.D. | N.D. |
| A1-Sp3-P | + | N.D. | N.D. |
| A1-Sp3-S | + | N.D. | N.D. |
| A1-Sp3-O | ++ | N.D. | N.D. |
| A1-Sp3-A | + | N.D. | N.D. |
| A1-Sp3-L | + | N.D. | N.D. |
| A1-Sp4-P | + | N.D. | N.D. |
| A1-Sp4-S | + | N.D. | N.D. |
| A1-Sp4-O | + | N.D. | N.D. |
| A1-Sp4-A | + | N.D. | N.D. |
| A1-Sp4-L | + | N.D. | N.D. |
| Effectene | 72% (79%) | 80% (66%) | 49% (57%) |
| A2-Sp1-P | 85% (99%) | 89% (97%) | 74% (98%) |
| A2-Sp1-S | + | N.D. | N.D. |
| A2-Sp1-O | ++ | N.D. | N.D. |
| A2-Sp1-A | + | N.D. | N.D. |
| A2-Sp1-L | + | N.D. | N.D. |
| A2-Sp2-P | 86% (99%) | 90% (98%) | 78% (99%) |
| A2-Sp2-S | ++ | N.D. | N.D. |
| A2-Sp2-O | + | N.D. | N.D. |
| A2-Sp2-A | ++ | N.D. | N.D. |
| A2-Sp2-L | + | N.D. | N.D. |
| A2-Sp3-P | + | N.D. | N.D. |
| A2-Sp3-S | + | N.D. | N.D. |
| A2-Sp3-O | ++ | N.D. | N.D. |
| A2-Sp3-A | + | N.D. | N.D. |
| A2-Sp3-L | + | N.D. | N.D. |
| A2-Sp4-P | + | N.D. | N.D. |
| A2-Sp4-S | + | N.D. | N.D. |
| A2-Sp4-O | ++ | N.D. | N.D. |
| A2-Sp4-A | + | N.D. | N.D. |
| A2-Sp4-L | + | N.D. | N.D. |
| Lipo2000 | 79% (88%) | 83% (75%) | 65% (78%) |
| A3-Sp1-P | 75% (93%) | 84% (95%) | 56% (89%) |
| A3-Sp1-S | ++ | N.D. | N.D. |
| A3-Sp1-O | + | N.D. | N.D. |
| A3-Sp1-A | + | N.D. | N.D. |
| A3-Sp1-L | + | N.D. | N.D. |
| A3-Sp2-P | 70% (92%) | 80% (96%) | 69% (93%) |
| A3-Sp2-S | ++ | N.D. | N.D. |
| A3-Sp2-O | ++ | N.D. | N.D. |
| A3-Sp2-A | + | N.D. | N.D. |
| A3-Sp2-L | + | N.D. | N.D. |
| A3-Sp3-P | ++ | N.D. | N.D. |
| A3-Sp3-S | + | N.D. | N.D. |
| A3-Sp3-O | ++ | N.D. | N.D. |
| A3-Sp3-A | + | N.D. | N.D. |
| A3-Sp3-L | + | N.D. | N.D. |
| A3-Sp4-P | + | N.D. | N.D. |
| A3-Sp4-S | + | N.D. | N.D. |
| A3-Sp4-O | + | N.D. | N.D. |
| A3-Sp4-A | + | N.D. | N.D. |
| A3-Sp4-L | ++ | N.D. | N.D. |
| Fugene | 71% (91%) | 92% (89%) | 47% (76%) |

4.3. Cell Viability Assay of Transfected Cells

Twenty-four hours after the addition of transfection agents, cell viability was measured using an MTT cell proliferation assay (LGC Promochem, Middlesex, UK), which was performed according to the manufacturer's instructions. Absorbance was read at 570 nm. The results indicated that none of the compounds were toxic at the concentration used for transfection (N/P ratios 1.5/1, 3/1, 6/1 and 12/1). The comparative data obtained with lipids 28a, 29a, 30a and 31a of the invention, Lipofectamine™ 2000, Fugene and Effectene® Transfection Reagent are shown between brackets in Table 2.

4.4. Transfection of siRNA into HeLa Cells

Cells were suspended using trypsin/EDTA and counted. $2 \times 10^4$ cells in 150 μL of RPMI-CM per well were seeded in 96-well plates and incubated overnight. The day afterwards, the different lipoplex formulations formulated with siGLO (fluorescein-labeled siRNA that localizes within cell nuclei (Dharmacon)) and added to the cells. Each experiment was performed in quadruplicate, using Lipofectamine™ 2000 (Invitrogen) as a positive control and untreated cells as a negative control. After 24 h incubation at 37° C. and 5% $CO_2$ (change of media after transfection was not necessary), the green fluorescence emitted by intracellular siGLO was imaged under microscope. Nuclear co-localisation was studied using Hoechst 33324. For the flow cytometry analysis, cells were washed twice with PBS, detached with trypsin/EDTA, harvested with 2% FBS in PBS, centrifuged and resuspended with 2% FBS in PBS and analyzed using a BD FACSaria flow cytometer. As shown in FIG. 1 assays using derivative 29a for transfecting siRNA resulted in over 96% of cells fluorescently labelled (Lipofectamine 2000 obtained 56%).

FIG. 1(a) shows cells imaged under FITC excitation filter and FIG. 1(b) shows cell nuclei imaged under DAPI excitation filter.

4.5. In Vivo Transfection

Experiments were performed to transfect a luciferase-expressing plasmid (pLux) by intravenous injection via the vein tail of mice: three transfected with pLux complexed with compound 29a and three (control) with naked pLux. Two days after instillation, firefly luciferin was administrated intraperitoneally and the mice imaged using an IVIS Spectrum.

FIG. 2 shows representative luminescence imaging of the anaesthetised mice 48 hours after transfection. The mouse depicted on the left was transfected with naked plasmid; the mouse the right was transfected with plasmid complexed with compound 29a. Mice (n=3, per experiment) were anaesthetised and intubated following standard protocols. 16 μg of a luciferase-reporter plasmid were used per mouse. Mice were monitored and analysed on a daily basis, and all of them behaved normally during the study. Firefly luciferin (15 mg/kg) was administered intraperitoneally to the anesthetized mice 15 min before scanning for luminescence. Imaging was performed on the IVIS Spectrum (Caliper LS) with large binning, open filter for 10 min.

Positive luminescence was detected in mice transfected with pLux complexed with compound 29a (right mouse) while no luminescence was observed in the control of naked pLux (left mouse).

Notably, the highest luminescence signal was observed at the point of injection, indicating that the high ability of this reagent for local delivery of DNA.

The invention claimed is:
1. A cationic lipid of formula (10):

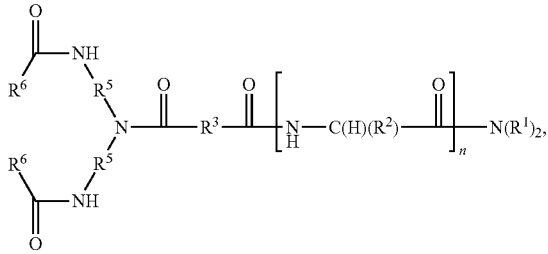

wherein:
- each $R^1$ is independently hydrogen or a $C_{1-5}$ alkyl;
- n is from 1 to 10;
- each $R^2$ is independently the side chain of an α-amino acid, at least one $R^2$ group comprising a cationic moiety or a cationic precursor;
- each $R^5$ is independently an optionally substituted $C_{1-4}$ alkylene moiety;
- $R^3$ is an optionally substituted alkylene or alkenylene moiety; and
- $R^6$ represents a saturated or unsaturated fatty alkyl chain, optionally comprising fused cyclic regions whereby to form a polycyclic hydrocarbyl moiety.

2. The cationic lipid of claim 1 wherein at least one $R^2$ group comprises an optionally substituted alkylene chain.

3. The cationic lipid of claim 1 wherein the cationic moiety or cationic precursor is or comprises an amine, amidine or guanidine group, or a protonated amine, amidine or guanidine group.

4. The cationic lipid of claim 1 wherein the at least one $R^2$ group is the side chain of a basic amino acid.

5. The cationic lipid of claim 4 wherein the basic amino acid is arginine, lysine, histidine or ornithine.

6. The cationic lipid of claim 4 wherein the basic amino acid is arginine.

7. The cationic lipid of claim 1 wherein n is from 2 to 10.

8. The cationic lipid of claim 7 wherein n is from 2 to 4.

9. The cationic lipid of claim 7 wherein each $R^2$ is the same.

10. The cationic lipid of claim 1, wherein $R^6$—C(O)— is represented as $CH_3(CH_2)_qC(=O)$— wherein q is from 5 to 100, optionally wherein one or more non-adjacent pairs of methylene groups (i.e. $CH_2CH_2$ units) are each replaced with CH=CH units whereby to define an unsaturated fatty acyl chain.

11. The cationic lipid of claim 10, wherein $R^6$—C(O)— is represented as $CH_3(CH_2)_qC(=O)$— wherein q is from 10 to 30, optionally wherein one or more non-adjacent pairs of methylene groups (i.e. $CH_2CH_2$ units) are each replaced with CH=CH units whereby to define an unsaturated fatty acyl chain.

12. The cationic lipid of claim 10, wherein $R^6$—C(O)— is represented as $CH_3(CH_2)_qC(=O)$— wherein q is from 12 to 24, optionally wherein one or more non-adjacent pairs of methylene groups (i.e. $CH_2CH_2$ units) are each replaced with CH=CH units whereby to define an unsaturated fatty acyl chain.

13. The cationic lipid of claim 1 wherein $R^3$ is an unsubstituted $C_{2-4}$ alkylene or alkenylene moiety.

14. The cationic lipid of claim 1 wherein each $R^5$ is an unsubstituted $C_{1-4}$ alkylene moiety.

15. The cationic lipid of claim 14 wherein each $R^5$ is ethylene or propylene.

16. A composition comprising a cationic lipid as defined in claim 1 in combination with an additional lipid and/or a biologically active molecule.

17. The composition of claim 16, wherein the biologically active molecule is a polynucleotide molecule.

18. The composition of claim 17 wherein the polynucleotide is a DNA or an RNA.

19. A method for transfecting a polynucleotide into a cell comprising contacting a cell with a composition according to claim 17.

20. The composition of claim 17, wherein the polynucleotide is a siRNA.

* * * * *